(12) United States Patent
Garst et al.

(10) Patent No.: US 6,559,167 B1
(45) Date of Patent: May 6, 2003

(54) PRODRUGS OF PROTON PUMP INHIBITORS

(75) Inventors: Michael E. Garst, Newport Beach, CA (US); George Sachs, Encino, CA (US); Jai Moo Shin, Northridge, CA (US)

(73) Assignees: Regents of the University of California, Oakland, CA (US); The United States of America as represented by the Department of Veteran Affairs, Washington, DC (US); Winston Pharmaceuticals, LLC, Newport Beach, CA (US)

(*) Notice: Subject to any disclaimer, the term of this patent is extended or adjusted under 35 U.S.C. 154(b) by 0 days.

(21) Appl. No.: 09/783,807

(22) Filed: Feb. 14, 2001

Related U.S. Application Data

(63) Continuation-in-part of application No. 09/364,381, filed on Jul. 29, 1999, now abandoned, which is a continuation-in-part of application No. 09/131,481, filed on Aug. 10, 1998, now Pat. No. 6,093,734.

(51) Int. Cl.$^7$ ................. A61K 31/445; A61K 31/4439; C07D 401/12; C07D 401/14

(52) U.S. Cl. ................ 514/338; 514/276; 514/300; 514/303; 514/338; 514/336; 514/387; 546/114; 546/118; 546/194; 546/268.1; 546/280.4; 546/281.1

(58) Field of Search ................ 546/113, 114, 546/115, 118, 280.4, 281.1, 271, 272.7, 256, 268.1, 273.7; 514/276, 338, 318, 235.2

(56) References Cited

U.S. PATENT DOCUMENTS

| | | | |
|---|---|---|---|
| 4,045,563 A | 8/1977 | Berntsson et al. | 424/263 |
| 4,255,431 A | 3/1981 | Junggren et al. | 424/263 |
| 4,628,098 A | 12/1986 | Nohara et al. | 546/271 |
| 4,686,230 A | 8/1987 | Rainer et al. | 514/338 |
| 4,758,579 A | 7/1988 | Kohl et al. | 514/338 |
| 4,965,269 A | 10/1990 | Brändström et al. | 514/253 |
| 5,021,433 A | 6/1991 | Alminger et al. | 514/338 |
| 5,045,552 A | 9/1991 | Souda et al. | 514/338 |
| 5,430,042 A | 7/1995 | Lindberg et al. | 514/338 |
| 5,693,818 A | 12/1997 | Von Uge | 546/273.7 |
| 5,708,017 A | 1/1998 | Dave et al. | 514/393 |
| 5,945,425 A * | 8/1999 | Moorman et al. | 514/269 |

FOREIGN PATENT DOCUMENTS

| | | | |
|---|---|---|---|
| WO | WO 97/48380 | 12/1997 | A61K/9/00 |

OTHER PUBLICATIONS

Design of prodrugs: Bioreversible derivatives for various functional groups and chemical entities, *Design of Prodrugs* (Bundgaard, H., ed.) 1985 Elsevier Science Publishers Publishers B. V. (*Biomedical Division*), Chapter 1, H. Bundgaard et al.

Formation of Prodrugs of Amines, Amides, Ureides, and Imides, by H. Bundgaard, *Methods in Enzimology*, vol. 112, pp. 347–359.

International Journal of Pharmaceuticals, vol. 22, 1984, pp. 45–56 (Elsevier, H. Bundgaard et al.

International Journal of Pharmaceuticals, vol. 29, 1986, pp. 19–28 (Elsevier), H. Bundgaard et al.

Journal of Medicinal Chemistry, vol. 32, No. 12, Dec. 1989, pp. 2503–2507, H. Bundgaard et al.

Chemical Abstracts, vol. 93, 1980, abstract No. 137935y, Bundgaard et al.

Chemical Abstracts, vol. 95, 1981, abstract No. 138493f, Bundgaard et al.

Chemical Abstracts, vol. 95, 1981, abstract No. 138592n, Bundgaard et al.

Chemical Abstracts, vol. 110, 1989, abstract No. 57664, Alminger et al.

Chemical Abstracts, vol. 115, 1991, abstract No. 64029s, Buur et al.

Chemical Abstracts, vol. 115, 1991, abstract No. 189582y, Hansen et al.

Chemical Abstracts, vol. 117, 1992, abstract No. 14347q, Bundgaard et al.

Chemical Abstracts, vol. 117, 1992, abstract No. 55790x, Jensen et al.

Chemical Abstracts, vol. 123, 1995, abstract No. 17593b, Thomsen et al.

Chemical Abstracts, vol. 58, (1962), abstract No. 20823d, Boehme et al.

Journal of Medicinal Chemistry, 32, 1970–1977 (1989).

Chem. Pharm. Bull., 38, 2853–2858 (1990).

J. Med. Chem., 34, 1049–1062 (1991).

Journal of Medicinal Chemistry, 35, 1049–1057 (1992).

Journal of Medicinal Chemistry, 35, 438–450 (1992).

Böhme et al., (Chemische Berichte, vol., 93, pp. 1305–1309 (1960).

(List continued on next page.)

*Primary Examiner*—D. Margaret Seaman
*Assistant Examiner*—Janet Coppins
(74) *Attorney, Agent, or Firm*—Gabor L. Szekeres

(57) ABSTRACT

Prodrugs of the pyridyl methyl sulfinyl benzimidazole type proton pump inhibitor drugs have a hydrolyzable arylsulfonyl or heteroarylsulfonyl group attached to the benzimidazole nitrogen. The prodrugs of the invention hydrolyze under physiological conditions to provide the proton pump inhibitors with a half life measurable in hours, and are capable of providing sustained plasma concentrations of the proton pump inhibitor drugs for longer time than presently used drugs. The generation of the proton pump inhibitor drugs from the prodrugs of the invention under physiological conditions allows for more effective treatment of several diseases and conditions caused by gastric acid secretion.

20 Claims, No Drawings

OTHER PUBLICATIONS

Grail et al., (Journal of American Chemical Society, 1952, 74, 1313–1315).
Böhme et al., (Chemische Berichte, vol. 95, pp. 1849–1858 (1962).
Cremlyn et al., J. Chem. Soc., Perkin I 500–503 (1973).
Cremlyn et al., Phosphorus, Sulfur, and Silicon, vol. 73, pp. 107–120 (1992).
Alo et al., Journal of Hetercyclic Chemistry, vol. 29, pp. 61–64 (1992).
J. Clin. Pharm., 1998, 38 (7) 593–602.
J. Pharm. Sci., 1997, 86(3) 335–339.
J. Pharm. Sci., 1992, 81, 524–528.
J. Pharm. Sci., 1999, 88, 1016–1020.
J. Pharm. Sci., 1999, 88. 1107–1111.
Larsson et al., Scand. J. Gastroenterology, vol. 20 (suppl. 108), 23–35, 1985.
Cremlyn et al., Indian Journal of Chemistry (1986) vol. 25B, 559–561.
Hurtley et al., (1926) J. Chem. Soc., 1821–1828.

* cited by examiner

PRODRUGS OF PROTON PUMP INHIBITORS

CROSS-REFERENCE TO RELATED APPLICATION

The present application is a continuation-in-part of application Ser. No. 09/364,381 filed on Jul. 29, 1999, now abandoned, which is a continuation-in-part of application Ser. No. 09/131,481, filed on Aug. 10, 1998, now U.S. Pat. No. 6,093,734.

The Government of the United States of America through the Department of Veteran Affairs has an interest in this application.

BACKGROUND OF THE INVENTION

Field of the Invention

The present invention is directed to prodrugs of proton pump inhibitors which are useful as anti-ulcer agents. More particularly, the present invention is directed to prodrugs that slowly hydrolyze to provide benzimidazole-type proton pump inhibitors which inhibit exogenously or endogenously gastric acid secretion and thus can be used in the prevention and treatment of gastrointestinal inflammatory diseases in mammals, including humans.

Brief Description of the Prior Art

Benzimidazole derivatives intended for inhibiting gastric acid secretion are disclosed in the U.S. Pat. Nos. 4,045,563; 4,255,431; 4,628,098; 4,686,230; 4,758,579; 4,965,269; 5,021,433; 5,430,042 and 5,708,017. Generally speaking, the benzimidazole-type inhibitors of gastric acid secretion work by undergoing a rearrangement to form a thiophilic species which then covalently binds to gastric H,K-ATPase, the enzyme involved in the final step of proton production in the parietal cells, and thereby inhibits the enzyme. Compounds which inhibit the gastric H,K-ATPase enzyme are generally known in the field as "proton pump inhibitors" (PPI).

Some of the benzimidazole compounds capable of inhibiting the gastric H,K-ATPase enzyme have found substantial use as drugs in human medicine and are known under such names as LANSOPRAZOLE (U.S. Pat. No. 4,628,098), OMEPRAZOLE (U.S. Pat. Nos. 4,255,431 and 5,693,818), PANTOPRAZOLE (U.S. Pat. No. 4,758,579), and RABEPRAZOLE (U.S. Pat. No. 5,045,552). The diseases treated by proton pump inhibitors and specifically by the four above-mentioned drugs include peptic ulcer, heart burn, reflux esophagitis errosive esophagitis, non-ulcer dispepsia, infection by *Helicobacter pylori,* alrynitis and asthma among others.

Whereas the proton pump inhibitor type drugs represent substantial advance in the field of human and veterinary medicine, they are not totally without shortcomings or disadvantages. The shortcomings of the presently used proton pump inhibitor (PPI) type drugs can be best explained by a more detailed description of the mode of their action, the diseases or condition against which they are employed and the circumstances of their application. Thus, acid related diseases include but are not limited to erosive esophagitis, esophageal reflux, gastric and duodenal ulcer, non-ulcer dyspepsia and infection by *Helicobacter pylori.* Current therapy of all but the infection by *H. pylori* bacteria involves treatment with drugs designed to suppress acid secretion, one type of which are the above-mentioned proton pump inhibitors.

The presently used proton pump inhibitors are pyridyl methyl sulfinyl benzimidazoles (or compounds of closely related structure) with a $pK_a$ of 4.0 to 5.0. Their mechanism of action requires accumulation in the acidic space of the parietal cell (secretory canaliculus, pH ca. 1.0) and subsequently hydrogen ion catalyzed conversion to the reactive thiophilic species that is capable of inhibiting the gastric ATPase, enzyme resulting in effective inhibition of gastric secretion. Because of this mechanism the presently used PPI type drugs require specialized gastro protection to remain active for duodenal absorption. For this reason, and due to sensitivity to degradation in the acid milieu of the stomach, oral formulations of the PPI drugs are usually enteric coated. The need for enteric coating is a shortcoming because enteric coating is expensive and moisture sensitive.

Because of the requirement for accumulation in the acid space of the parietal cell, acid secretion is necessary for the efficacy of the PPI type drugs. It was found that the plasma half life of these drugs is between 60 to 90 minutes. All acid pumps are not active at any one time, rather only about 75% are active on the average during the time the drug is present in the blood following oral administration. It was also found in medical experience that on a currently used once-a-day oral administration therapy the maximal inhibition of stimulated acid output is approximately 66%. This is due to a combination of the short plasma half life of the drug, to the limited number of acid pumps active during presentation of the drug and to the turn-over of acid pumps. In present practice it is not possible to control night time acid secretion by evening therapy of oral administration because the drug is dissipated from the plasma by the time acid secretion is established after midnight. The ideal target for healing in acid related diseases and for treatment of *H. pylori* infection (in conjunction with antibiotics), as well as for relief of symptoms of non-ulcer dyspepsia would be full inhibition of acid secretion. With the currently used PPI type drugs this is achieved only by intravenous infusion; in case of the drug OMEPRAZOLE this requires intravenous infusion of 8 mg per hour. Clearly, there is a need in the art for a drug or drugs acting through the mechanism of PPI-type drugs which can attain or approach full inhibition of acid secretion through oral therapy.

Because of the less than full inhibition of acid secretion and less than 24 hour inhibition through oral administration that is attained by the current dosage forms of currently used PPI-type drugs, therapy for healing of gastric and duodenal ulcerations is 4 to 8 weeks. This is in spite of the fact that the generation time of surface cells of the esophagus, stomach and duodenum is approximately 72 hours. Undoubtedly the presently observed prolonged healing times with these drugs is due to inadequate acid suppression and acid related damage. The foregoing underscores the need in the art for a drug or drugs acting through the mechanism of PPI-type drugs which can attain or approach full inhibition of acid secretion through oral therapy.

As further pertinent background to the present invention, applicants note the concept of prodrugs which is well known in the art. Generally speaking, prodrugs are derivatives of per se drugs, which after administration undergo conversion to the physiologically active species. The conversion may be spontaneous, such as hydrolysis in the physiological environment, or may be enzyme catalyzed. From among the voluminous scientific literature devoted to prodrugs in general, the foregoing examples are cited: Design of Prodrugs (Bundgaard H. ed.) 1985 Elsevier Science Publishers B. V. (Biomedical Division), Chapter 1; Design of Prodrugs: Bioreversible derivatives for various functional groups and chemical entities (Hans Bundgaard); Bundgaard et al. Int. J. of Pharmaceutics 22 (1984) 45–56 (Elsevier); Bundgaard et al. Int. J. of Pharmaceutics 29 (1986) 19–28 (Elsevier); Bundgaard et al. J. Med. Chem. 32 (1989) 2503–2507 Chem. Abstracts 93, 137935y (Bundgaard et al.); Chem. Abstracts 95, 138493f (Bundgaard et al.); Chem. Abstracts 95, 138592n (Bundgaard et al.); Chem. Abstracts 110, 57664p (Alminger et al.); Chem. Abstracts 115, 64029s (Buur et al.); Chem. Abstracts 115, 189582y (Hansen et al.); Chem. Abstracts 117, 14347q (Bundgaard et al.); Chem. Abstracts 117, 55790x (Jensen et al.); and Chem. Abstracts 123, 17593b (Thomsen et al.).

As far as the present inventors are aware, there are no prodrugs of the proton pump inhibitors presently in use. However, several U.S. patents describe compounds which can act as prodrugs of certain proton pump inhibitors. Specifically, U.S. Pat. No. 4,686,230 (Rainer et al.) describes derivatives of pyridyl methyl sulfinyl benzimidazoles which include a group designated "$R_5$" on one of the benzimidazole nitrogens. The "$R_5$" group is expected to cleave under physiological condition, or under the influence of an enzyme to provide the corresponding compound with a free N-H bond (see column 3 of U.S. Pat. No. 4,686,230). U.S. Pat. Nos. 5,021,433 (Alminger et al.), 4,045,563 (Berntsson et al.), 4,965,269 and (Brändström et al.) also describe pyridyl methyl sulfinyl benzimidazoles where one of the nitrogens of the benzimidazole moiety bears a substituent that cleaves under physiological or enzymatic conditions. U.S. Pat. No. 4,045,563 (Berntsson et al.) describes N-alkoxycarbonyl benzimidazole derivates.

A publication by Sih., et al. Journal of Medicinal Chemistry, 1991, vol. 34, pp 1049–1062, describes N-acyloxyalkyl, N-alkoxycarbonyl, N-(aminoethyl), and N-alkoxyalkyl derivatives of benzimidazole sulfoxide as prodrugs of proton-pump inhibitors. According to this article these prodrugs exhibited improved chemical stability in the solid state and in aqueous solutions, but had similar activity or less activity than the corresponding parent compounds having a free imidazole N-H group. This publication does not provide data regarding the duration of the inhibitory activity of these prodrugs.

The present invention represents further advance in the art in that it provides prodrugs of improved structure of the proton pump inhibitor type drugs and provides proof of the suitability of the prodrugs of the invention for use as prodrug of proton pump inhibitors, with improved efficacy in therapy of acid related diseases due to prolongation of the presence of the proton pump inhibitors in the body.

SUMMARY OF THE INVENTION

The present invention relates to compounds of Formula 1

wherein $Het_1$ is selected from the formulas shown below

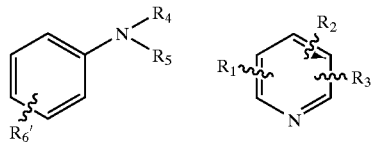

X is selected from the formulas

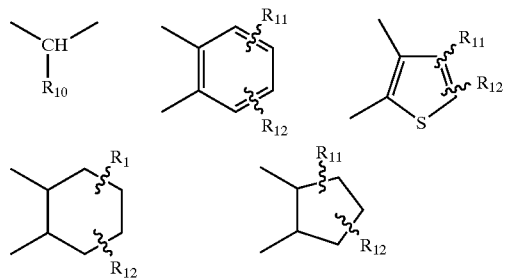

and $Het_2$ is selected from the formulas

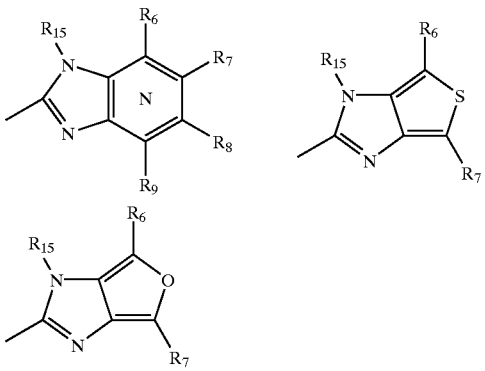

where N in the benzimidazole moiety means that one of the ring carbons may be exchanged for an unsubstituted N atom; $R_1$, $R_2$ and $R_3$ are independently selected from hydrogen, alkyl of 1 to 10 carbons, fluoro substituted alkyl of 1 to 10 carbons, alkoxy of 1 to 10 carbons, fluoro substituted alkoxy of 1 to 10 carbons, alkylthio of 1 to 10 carbons, fluoro substituted alkylthio of 1 to 10 carbons, alkoxyalkoxy of 2 to 10 carbons, amino, alkylamino and dialkylamino each of the alkyl groups in said alkylamino and dialkyl amino groups having 1 to 10 carbons, halogen, phenyl, alkyl substituted phenyl, alkoxy substituted phenyl, phenylalkoxy, each of the alkyl groups in said alkyl substituted phenyl, alkoxy substituted phenyl and phenylalkoxy having 1 to 10 carbons, piperidino, morpholino or two of the $R_1$, $R_2$ and $R_3$ groups jointly forming a 5 or 6 membered ring having 0 or 1 heteroatom selected from N, S and O;

$R_4$ and $R_5$ are independently selected from hydrogen, alkyl of 1 to 10 carbons, fluoro substituted alkyl of 1 to 10 carbons, phenylalkyl, naphthylalkyl and heteroarylalkyl, alkyl in said phenylalkyl, naphthylalkyl and heteroarylalkyl groups having 1 to 10 carbons;

$R_6$ is hydrogen, halogen, alkyl of 1 to 10 carbons, fluoro substituted alkyl of 1 to 10 carbons, alkoxy having 1 to 10 carbons or fluoro substituted alkoxy having 1 to 10 carbons;

$R_6$ through $R_9$ are independently selected from hydrogen, halogen, alkyl of 1 to 10 carbons, halogen substituted alkyl of 1 to 10 carbons, alkoxy of 1 to 10 carbons, halogen substituted alkoxy of 1 to 10 carbons, alkylcarbonyl, alkoxycarbonyl the alkyl group in said alkylcarbonyl and alkoxycarbonyl having 1 to 10 carbons, oxazolyl, imidazolyl, thiazolyl, morpholinyl, piperazinyl, pyrazinyl, pyrazolyl, or any two adjacent ones of the $R_6$ through $R_9$ groups may form a ring that may optionally include a heteroatom selected from N, O and S and said ring may be further substituted;

$R_{10}$ is hydrogen, alkyl of 1 to 10 carbons, or $R_{10}$ may form an alkylene chain together with $R_3$, $R_{11}$ and $R_{12}$ are independently selected from hydrogen, halogen, alkyl of 1 to 10 carbons and halogen substituted alkyl of 1 to 10 carbons;

$R_{15}$ has the formula below

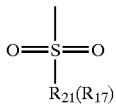

where $R_{17}$ is alkyl of 1 to 10 carbons, halogen substituted alkyl of 1 to 10 carbons, alkoxy having 1 to 10 carbons, halogen substituted alkoxy of 1 to 10 carbons, alkylthio having 1 to 10 carbons, halogen substituted alkylthio of 1 to 10 carbons, alkoxy carbonyl having 1 to 10 carbons, halogen substituted alkoxy carbonyl having 1 to 10 carbons, F, Cl, Br, I, $NO_2$, CN, OCOalkyl, $NH_2$, alkylamino and dialkylamino where in said OCOalkyl, alkylamino and dialkylamino groups each of said alkyl group has 1 to 10 carbons, further $R_{17}$ is carbamoyl, N- lower alkyl carbamoyl having 1 to 6 carbons, alkylcarbonyl having 1 to 10 carbons, (alkoxycarbonyl) alkoxy groups of each of said alkoxy group has 1 to 10 carbons, (alkoxycarbonyl)alkyl groups of each of said alkoxy or alkyl group has 1 to 10 carbons, (carbamoyl) alkoxy having 1 to 10 carbons, (N-alkylcarbamoyl)alkoxy where each of said alkoxy or alkyl groups has 1 to 6 carbons, (N,N-dialkylcarbamoyl)alkoxy where each of said alkoxy or alkyl groups has 1 to 6 carbons, (N-alkyl substituted or unsubstituted carbamoyl)poly(alkoxy)$_n$ where each of said alkoxy or alkyl groups has 1 to 6 carbons and where n represents an integer selected from 2 to 5, (N-alkyl substituted or unsubstituted carbamoyl)alkyl where each of said alkyl groups has 1 to 5 carbons, (carbamoyl)alkenyl having 2 to 5 carbons, (dialkylcarbamoyl)alkenyl where each of said alkyl groups has 1 to 5 carbons and where the alkenyl group has 2 to 5 carbons, [N-(heteroaryl)carbamoyl]alkyl having 1 to 10 carbons wherein heteroaryl has 1 to 3 heteroatoms independently selected from N, O, and S, [N-(heteroaryl)carbamoyl]alkoxy having 1 to 10 carbons wherein heteroaryl has 1 to 3 heteroatoms independently selected from N, O, and S, poly(alkoxy)$_n$ where each of said alkoxy groups has 2 to 10 carbons and wherein n represents an integer selected from 2 to 5, 2-[(2-oxy-ethoxy)-ethoxyl-(ethoxy)$_n$-ethanoxy wherein n represents an integer selected from 1 to 3, guanidinyl group, ureido group, (dialkylamino) alkyl where each of said alkyl groups has 1 to 5 carbons, (dialkylamino)alkoxy where each of said alkyl or alkoxy groups has 1 to 5 carbons, dialkylamino-poly(alkoxy)$_n$ where each of said alkyl or alkoxy groups has 1 to 5 carbons and wherein n represents an integer selected from 2 to 5, [N-(carbamoylalkyl)carbamoyl]alkoxy where each of said alkoxy or alkyl groups has 1 to 5 carbons, (N-peptidyl carbamoyl)alkoxy where the alkoxy group has 1 to 5 carbons and wherein said peptidyl consists of two or three amino acids, N-peptidyl amido wherein said peptidyl consists of two or three amino acids, [N-(carbamoylalkyl) carbamoyl]alkyl where each of said alkyl groups has 1 to 5 carbons, [N-[(dicarbamoyl)alkyl]carbamoyl]alkoxy where each of said alkoxy or alkyl groups has 1 to 5 carbons, [N-(di(alkoxycarbonyl))alkyl]carbamoyl]alkoxy where each of said alkoxy or alkyl groups has 1 to 5 carbons, [N-[(dicarbamoyl)alkyl]amido where alkyl groups has 1 to 5 carbons, [N-[di(alkoxycarbonyl)alkyl]amido where each of said alkoxy or alkyl groups has 1 to 5 carbons, [N-[(carbamoyl)alkyl]amido where alkyl groups has 1 to 5 carbons, [N-[(alkoxycarbonyl)alkyl]amido where each of said alkoxy or alkyl groups has 1 to 5 carbons, [N-[[N-(heteroaryl) carbamoyl]alkyl]carbamoyl]alkoxy where each of said alkoxy or alkyl groups has 1 to 5 carbons and wherein said heteroaryl has 1 to 3 heteroatoms independently selected from N, O, and S, [(tri-alkyl)ammonium]-alkoxy where each of said alkoxy or alkyl groups has 1 to 5 carbons, $SO_3^-$, aminosulfonyl, (sulfonato)alkyl having 2 to 5 carbons, (sulfonato)alkoxy having 2 to 5 carbons, N-[(sulfonato)alkyl]amido having 2 to 5 carbons, maleimido- and succinimido, and $R_{21}$ is (aryl)alkyl, (heteroaryl)alkyl where alkyl has 1 to 10 carbons, phenyl, naphthyl or heteroaryl having 1 to 3 heteroatoms independently selected from N, O and S, said phenyl, naphthyl or heteroaryl groups being unsubstituted or substituted with 1 to 5 $R_{17}$ groups, or to a pharmaceutically acceptable salt of said compounds.

The compounds of the invention are sulfoxides and have an asymmetric center in the sulfur atom. Both the pure enatiomers, racemic mixtures and unequal mixtures of the two are within the scope of the present invention. Some of the compounds of the invention may have one or more asymmetric carbon atoms (for example in a branch-chained alkyl group). All optical isomers, racemates, diastereomers and their mixtures are within the scope of the invention.

The compounds of the invention act as prodrugs of proton pump inhibitor type drugs which are useful for inhibiting gastric acid secretion. The compounds of the invention have excellent stability in tablet or capsule form, are acid stable, have excellent bioavailability and plasma half life which is significantly longer than the plasma half life of the presently used proton pump inhibitors.

DETAILED DESCRIPTION OF THE INVENTION

The chemical structure of the compounds of the invention is shown and described in broad terms in the Summary of the Invention in connection with Formula 1. As it can be seen in the formula, the compounds of the invention are pyridyl methyl sulfinyl benzimidazoles, or compounds of closely related structure, wherein one of the benzimidazole nitrogens is substituted with a group (designated $R_{15}$ in Formula 1) that gradually cleaves under physiological conditions and thereby provides the pyridyl methyl sulfinyl benzimidazole compound (or compound of closely related structure) which has a free N-H function in the benzimidazole (or related) moiety. The compound thus obtained by cleavage of the $R_{15}$ group then undergoes the acid catalyzed rearrangement and provides the thiophilic species which inhibits the H,K-ATPase enzyme involved in gastric acid production. Thus, the novel compounds of the present invention bearing the $R_{15}$ group are prodrugs of the proton pump inhibitor compounds which could also be depicted by Formula 1, where, however the $R_{15}$ group would be designated hydrogen.

Generally speaking, among the prodrugs compounds of the present invention those are preferred wherein the structure of the pyridyl methyl sulfinyl benzimidazole or structurally related moiety is also preferred in the prior art. In other words, preferably prodrugs are provided in accordance with the present invention for those proton pump inhibitor drugs which are themselves preferred.

Referring now to the specific designation of symbols in connection with Formula 1, compounds are preferred in accordance with the present invention wherein the moiety designated $Het_1$ is pyridyl substituted with alkyl, O-alkyl, O-alkoxyalkyl and/or O-fluoroalkyl groups. Most preferred substituents for the pyridine moiety, designated $R_1$, $R_2$ and $R_3$ in Formula 1, are $CH_3O$—, $CH_3$—, $CF_3CH_2O$—, and $CH_3O(CH_2)_3O$—.

The moiety designated X in Formula 1 is preferably a methylene (—$CH_2$—) group, or a —$CHR_{10}$ group and the methylene or —$CHR_{10}$ group is preferably attached in α position to the nitrogen in the pyridine moiety. Compounds where the X is ortho phenylene or substituted ortho phenylene are also preferred; in the most preferred compounds X is methylene.

Referring now to the group designated $Het_2$ in Formula 1, this moiety is preferably a substituted benzimidazole. The $R_6$ through $R_9$ groups preferably are selected from hydrogen, chlorine and fluoro-substituted alkoxy groups, with hydrogen, chlorine, $CF_2HO$— and $CH_3O$— being even more preferred.

Referring now to the group designated $R_{15}$ in connection with Formula 1 it will be apparent to those skilled in the art that this group represents the principal novel structural feature of the present invention. Among the $R_{15}$ groups shown in connection with Formula 1 the phenylsulfonyl and heteroarylsulfonyl groups (designated $R_{21}(R_{17})SO_2$—) are preferred. Even more preferably the aryl portion ($R_{21}$) is phenyl or pyridyl unsubstituted or substituted with 1 to 3 $R_{17}$ groups. When the $R_{21}$ group is substituted, then the substituent ($R_{17}$) is preferably selected from Cl, Br, F, alkyl, alkoxy, trifluoromethyl, trifluoromethoxy, di-(alkyl)amino, alkoxycarbonyl, (alkoxycarbonyl)alkoxy, ureido, guanidinyl, carbamoyl, N-alkyl carbamoyl, carbamoylalkyl, (N-alkyl carbamoyl)alkyl, (carbamoyl)alkenyl, (dialkylcarbamoyl)alkenyl, di-(alkylamino)alkoxy, morpholinyl, (morpholin-4-yl)alkoxy, (morpholin-4-yl)poly(alkoxy)$_n$ where n is an integer having the value of 2 to 5, di-(alkylamino)alkyl, poly(alkoxy)$_n$ alkoxy where n is an integer having the value of 1 to 5, 2-[(2-oxy-ethoxy)-ethoxy]-(ethoxy)$_n$-ethanoxy wherein n represents an integer selected from 1 to 3, (carbamoyl)alkoxy, [(N-(alkyl)carbamoyl]alkoxy, [N,N-(dialkyl)carbamoyl)alkoxy, (N,N-dialkylcarbamoyl)alkyl, [N-(heteroaryl)carbamoyl]alkyl, [N-(heteroaryl)carbamoyl]alkoxy, [N-(aryl)carbamoyl]alkoxy, [N-[(dicarbamoyl)alkyl]carbamoyl]alkoxy, [N-[(carbamoyl)alkyl]carbamoyl]alkoxy, [N-[(N-alkyl carbamoyl)alkyl]carbamoyl]alkoxy, [N-[di(alkoxycarbonyl)alkyl]carbamoyl]alkoxy, [N-[(dicarbamoyl)alkyl]amido, [N-[di(alkoxycarbonyl)alkyl]amido, [N-[(carbamoyl)alkyl]amido, [N-[(alkoxycarbonyl)alkyl]amido, $SO_3^-$, aminosulfonyl, (sulfonato)alkyl, (sulfonato)alkoxy, N-[(sulfonato)alkyl]amido, maleimido-, succinimido and [(tri-alkyl)ammonium]-alkoxy groups, wherein the terms alkyl and alkoxy, define groups having 1 to 6 carbons, and alkenyl defines groups having 2 to 5 carbons, and heteroaryl has 1 to 3 heteroatoms independently selected from N, O, and S.

Even more preferably the $R_{21}$ group is unsubstituted ($R_{17}$ is H) or the substituent of the $R_{21}$ group is selected from Cl, Br, F, methyl, methoxy, trifluoromethyl, trifluoromethoxy, dimethylamino, ethoxycarbonyl, (methoxycarbonyl)methoxy, carbamoyl, guanidinyl, ureido, 2-carbamoyl vinyl, 2-(N,N-dimethylcarbamoyl)vinyl, (carbamoyl)methoxy, [N-(pyridyl)carbamoyl]methoxy, morpholinyl, (morpholin-4-yl)alkoxy, [(morpholin-4-yl)alkoxy]alkoxy, 2-(dimethylamino)ethoxy, [N-[(carbamoyl)methyl]carbamoyl]methoxy, (N-(1,3-dicarbamoyl-propyl)carbamoyl)methoxy, (dimethylamino)methyl, $SO_3^-$, aminosulfonyl, sodium(sufonato)alkoxy having 2 to 4 carbons, (trimethylammonium) alkoxy having 2 to 4 carbons, poly(alkoxy)$_n$, wherein the alkoxy groups have 1 to 3 carbons and n is an integer having the values of 2 to 5, and —$(OCH_2CH_2)_{n'}$—O— where n' is 4 or 5. Still more preferably there are one or two $R_{17}$ substituents (other than hydrogen) in the phenyl ($R_{21}$) moiety, and preferably the $R_{17}$ substituent is in a position para (1,4) and/or meta (1,3) to the sulfonyl ($SO_2$) group.

The most preferred compounds of the invention are those wherein the proton pump inhibitor portion is the same as in the widely used proton pump inhibitor drugs known under the names LANSOPRAZOLE, OMEPRAZOLE, PANTOPRAZOLE and RABEPRAZOLE and wherein the $R_{15}$ group is a benzenesulfonyl group or pyridyl group substituted in the 4 (para) and/or in the 3 (meta) position with a Cl, Br, F, $CH_3$, $CH_3O$, $CF_3$, $CF_3O$—, $(CH_3)_2N$, $NH_2CO$, $NH_2CONH$, $NH_2C(=NH)NH$, 4-morpholino, 2-(4-morpholinyl)ethoxy, 2-[2-(4-morpholinyl)ethoxy]ethoxy, 3-(4-morpholinyl)propoxy, poly(alkoxy)$_n$-alkoxy where n is an integer having the value of 1 to 3, $^-O_3S$—, $Na^{+-}O_3S$—$CH_2CH_2CH_2$—O, $X^-$ $(CH_3)_3NCH_2CH_2O$— (X is an anion, such as a halogen ion), $NH_2COCH_2O$, (pyridyl)$NHCOCH_2O$, $NH_2COCH_2NH_2COCH_2O$, $(CH_3)_2NCH_2$ or EtOCO group. These compounds are shown by Formulas 2, 3, 4 and 5, respectively, where $R_{17}*$ represents said Cl, Br, F, $CH_3$, $CH_3O$, $CF_3$, $CF_3O$—, $(CH_3)_2N$, $NH_2CO$, $NH_2CONH$, $NH_2C(=NH)NH$, 4-morpholino, 2-(4-morpholinyl)ethoxy, 2-[2-(4-morpholinyl)ethoxy]ethoxy, 3-(4-morpholinyl)propoxy, poly(alkoxy)$_n$-alkoxy where n is an integer having the value of 1 to 3, $^-O_3S$—, $NH_2COCH_2O$, (pyridyl)$NHCOCH_2O$, $NH_2COCH_2NHCOCH_2O$, $(CH_3)_2NCH_2$, $Na^+$ $^-O_3S$— $CH_2CH_2CH_2$—O, $(CH_3)_3N^+CH_2CH_2O$—, $MeOCOCH_2CH(COOMe)NHCO$ or EtOCO groups in the 4 (para) or in the 3 (meta) position of the phenyl ring, or in the 3 and 4 positions of the phenyl ring and where the numbering of the benzimidazole ring is shown in the formulas. In Formula 3 the $CH_3O$— group can occupy the 5 or the 6 position of the benzimidazole moiety, and in Formula 4 the $CF_2HO$— group can occupy the 5 or the 6 position of the benzimidazole moiety.

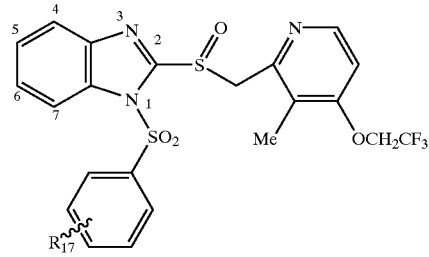

Formula 2

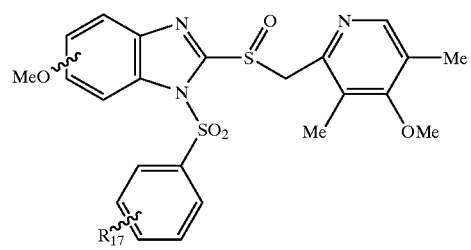

Formula 3

Formula 4

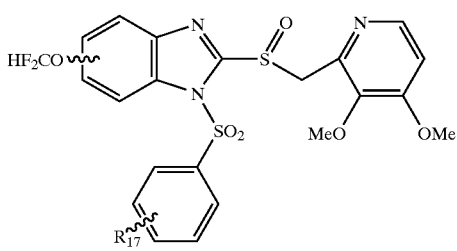

Formula 5

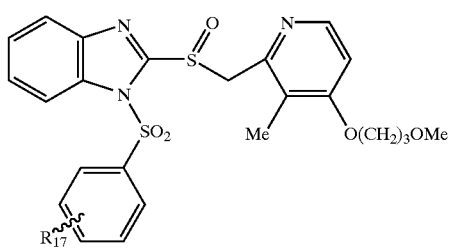

The compounds of the invention include
2-[[(3-chloro-4-morpholino-2-pyridyl)methyl]sulfinyl]-5-methoxy-(1H)-benzimidazole,
2-[[[4-(2,2,3,3,4,4,4-heptafluorobutyl)oxy]-2-pyridyl]methyl]sulfinyl]-1H-thieno[3,4-d]imidazole,
2-[[(4-ethythio-3-methyl-2-pyridyl)methyl]sulfinyl]-1h-benzimidazole
2-[(3-methoxyphenyl)methylsulfinyl]-1H-benzimidazole,
2-[(3-methoxyphenyl)methylsulfinyl]imidazolo[5,4-c]pyridine,
2-[(3-methoxyphenyl)methylsulfinyl]imidazolo[4,5-c]pyridine,
and 2-[(3-methoxyphenyl)methylsulfinyl]-5-nitro-benzimidazole, of which 1-position have $R_{15}$ group. $R_{15}$ group of these compounds is a benzenesulfonyl group mono-substituted either in the 4 (para) or in the 3 (meta) position with a Cl, Br, F, $CH_3$, $CH_3O$, $CF_3$, $CF_3O$, $(CH_3)_2N$, $NH_2CO$, $NH_2CONH$, $NH_2C(=NH)NH$, 4-morpholino, 2-(4-morpholinyl)ethoxy, 2-[2-(4-morpholinyl)ethoxy]ethoxy, 3-(4-morpholinyl)propoxy, $NH_2COCH_2O$, (pyridyl)$NHCOCH_2O$, $NH_2COCH_2NH_2COCH_2O$, $(CH_3)_2NCH_2$, $Na^+$ $^{-O}_3S-CH_2CH_2CH_2-O$, $(CH_3)_3N^+CH_2CH_2O-$, or EtOCO group.

Examples of the presently most preferred compounds of the invention are as follows:
1-benzenesulfonyl-5-methoxy-2-[(3,5-dimethyl-4-methoxy-2-pyridyl)methylsulfinyl]-1H-benzimidazole,
1-benzenesulfonyl-6-methoxy-2-[(3,5-dimethyl-4-methoxy-2-pyridyl)methylsulfinyl]-1H-benzimidazole,
1-benzenesulfonyl-5-difluoromethoxy-2-[(3,4-dimethoxy-2-pyridyl)methylsulfinyl]-1H-benzimidazole,
1-benzenesulfonyl-6-difluoromethoxy-2-[(3,4-dimethoxy-2-pyridyl)methylsulfinyl]-1H-benzimidazole,
1-benzenesulfonyl-2-[(3-methyl-4-(2',2',2'-trifluoroethoxy)-2-pyridyl)methylsulfinyl]-1H-benzimidazole,
1-(p-chlorobenzenesulfonyl)-5-methoxy-2-[(3,5-dimethyl-4-methoxy-2-pyridyl)methylsulfinyl]-1H-benzimidazole,
1-(p-chlorobenzenesulfonyl)-6-methoxy-2-[(3,5-dimethyl-4-methoxy-2-pyridyl)methylsulfinyl]-1H-benzimidazole,
1-(p-chlorobenzenesulfonyl)-5-difluoromethoxy-2-[(3,4-dimethoxy-2-pyridyl)methylsulfinyl]-1H-benzimidazole,
1-(p-chlorobenzenesulfonyl)-6-difluoromethoxy-2-[(3,4-dimethoxy-2-pyridyl)methylsulfinyl]-1H-benzimidazole,
1-(p-chlorobenzenesulfonyl)-2-[(3-methyl-4-(2',2',2'-trifluoroethoxy)-2-pyridyl)methylsulfinyl]-1H-benzimidazole,
1-(p-bromobenzenesulfonyl)-5-methoxy-2-[(3,5-dimethyl-4-methoxy-2-pyridyl)methylsulfinyl]-1H-benzimidazole,
1-(p-bromobenzenesulfonyl)-6-methoxy-2-[(3,5-dimethyl-4-methoxy-2-pyridyl)methylsulfinyl]-1H-benzimidazole,
1-(p-bromobenzenesulfonyl)-5-difluoromethoxy-2-[(3,4-dimethoxy-2-pyridyl)methylsulfinyl]-1H-benzimidazole,
1-(p-bromobenzenesulfonyl)-6-difluoromethoxy-2-[(3,4-dimethoxy-2-pyridyl)methylsulfinyl]-1H-benzimidazole,
1-(p-bromobenzenesulfonyl)-2-[(3-methyl-4-(2',2',2'-trifluoroethoxy)-2-pyridyl)methylsulfinyl]-1H-benzimidazole,
1-(p-fluorobenzenesulfonyl)-5-methoxy-2-[(3,5-dimethyl-4-methoxy-2-pyridyl)methylsulfinyl]-1H-benzimidazole,
1-(p-fluorobenzenesulfonyl)-6-methoxy-2-[(3,5-dimethyl-4-methoxy-2-pyridyl)methylsulfinyl]-1H-benzimidazole,
1-(p-fluorobenzenesulfonyl)-5-difluoromethoxy-2-[(3,4-dimethoxy-2-pyridyl)methylsulfinyl]-1H-benzimidazole,
1-(p-fluorobenzenesulfonyl)-6-difluoromethoxy-2-[(3,4-dimethoxy-2-pyridyl)methylsulfinyl]-1H-benzimidazole,
1-(p-fluorobenzenesulfonyl)-2-[(3-methyl-4-(2',2',2'-trifluoroethoxy)-2-pyridyl)methylsulfinyl]-1H-benzimidazole,
1-(p-methylbenzenesulfonyl)-5-methoxy-2-[(3,5-dimethyl-4-methoxy-2-pyridyl)methylsulfinyl]-1H-benzimidazole,
1-(p-methylbenzenesulfonyl)-6-methoxy-2-[(3,5-dimethyl-4-methoxy-2-pyridyl)methylsulfinyl]-1H-benzimidazole,
1-(p-methylbenzenesulfonyl)-5-difluoromethoxy-2-[(3,4-dimethoxy-2-pyridyl)methylsulfinyl]-1H-benzimidazole,
1-(p-methylbenzenesulfonyl)-6-difluoromethoxy-2-[(3,4-dimethoxy-2-pyridyl)methylsulfinyl]-1H-benzimidazole,
1-(p-methylbenzenesulfonyl)-2-[(3-methyl-4-(2',2',2'-trifluoroethoxy)-2-pyridyl)methylsulfinyl]-1H-benzimidazole,
1-(p-methoxybenzenesulfonyl)-5-methoxy-2-[(3,5-dimethyl-4-methoxy-2-pyridyl)methylsulfinyl]-1H-benzimidazole,
1-(p-methoxybenzenesulfonyl)-6-methoxy-2-[(3,5-dimethyl-4-methoxy-2-pyridyl)methylsulfinyl]-1H-benzimidazole,
1-(p-methoxybenzenesulfonyl)-5-difluoromethoxy-2-[(3,4-dimethoxy-2-pyridyl)methylsulfinyl]-1H-benzimidazole,
1-(p-methoxybenzenesulfonyl)-6-difluoromethoxy-2-[(3,4-dimethoxy-2-pyridyl)methylsulfinyl]-1H-benzimidazole,
1-(p-methoxybenzenesulfonyl)-2-[(3-methyl-4-(2',2',2'-trifluoroethoxy)-2-pyridyl)methylsulfinyl]-1H-benzimidazole,
1-(3-trifluoromethylbenzenesulfonyl)-5-methoxy-2-[(3,5-dimethyl-4-methoxy-2-pyridyl)methylsulfinyl]-1H-benzimidazole,
1-(3-trifluoromethylbenzenesulfonyl)-6-methoxy-2-[(3,5-dimethyl-4-methoxy-2-pyridyl)methylsulfinyl]-1H-benzimidazole,
1-(3-trifluoromethylbenzenesulfonyl)-5-difluoromethoxy-2-[(3,4-dimethoxy-2-pyridyl)methylsulfinyl]-1H-benzimidazole,
1-(3-trifluoromethylbenzenesulfonyl)-6-difluoromethoxy-2-[(3,4-dimethoxy-2-pyridyl)methylsulfinyl]-1H-benzimidazole,
1-(3 -trifluoromethylbenzenesulfonyl)-2-[(3-methyl-4-(2',2',2'-trifluoroethoxy)-2-pyridyl)methylsulfinyl]-1H-benzimidazole,
1-(p-trifluoromethoxybenzenesulfonyl)-5-methoxy-2-[(3,5-dimethyl-4-methoxy-2-pyridyl)methylsulfinyl]-1H-benzimidazole,
1-(p-trifluoromethoxybenzenesulfonyl)-6-methoxy-2-[(3,5-dimethyl-4-methoxy-2-pyridyl)methylsulfinyl]-1H-benzimidazole, 1-(p-trifluoromethoxybenzenesulfonyl)-5-difluoromethoxy-2-[(3,4-dimethoxy-2-pyridyl)methylsulfinyl]-1H-benzimidazole, 1-(p-trifluoromethoxybenzenesulfonyl)-6-difluoromethoxy-2-[(3,4-dimethoxy-2-pyridyl)methylsulfinyl]-1H-benzimidazole, 1-(p-trifluoromethoxybenzenesulfonyl)-2-[(3-methyl-4-(2',2',2'-trifluoroethoxy)-2-pyridyl)methylsulfinyl]-1H-benzimidazole, 1-(p-dimethylaminobenzenesulfonyl)-5-methoxy-2-[(3,5-dimethyl-4-methoxy-2-pyridyl)methylsulfinyl]-1H-benzimidazole, 1-(p-dimethylaminobenzenesulfonyl)-5-difluoromethoxy-2-[(3,4-dimethoxy-2-pyridyl)methylsulfinyl]-1H-benzimidazole, 1-(p-dimethylaminobenzenesulfonyl)-2-[(3-methyl-4-(2',2',2'-trifluoroethoxy)-2-pyridyl)methylsulfinyl]-1H-benzimidazole, 1-(p-ethoxycarbonylbenzenesulfonyl)-5-methoxy-2-[(3,5-dimethyl-4-methoxy-2-pyridyl)methylsulfinyl]-1H-benzimidazole, 1-(p-ethoxycarbonylbenzenesulfonyl)-2-[(3-methyl-4-(2',2',2'-trifluoroethoxy)-2-pyridyl)methylsulfinyl]-1H-benzimidazole, 1-(pyridine-3-sulfonyl)-5-methoxy-2-[[(3,5-dimethyl-4-methoxy-2-pyridyl)methyl]sulfinyl]-1H-benzimidazole, 1-(pyridine-3-sulfonyl)-6-methoxy-2-[[(3,5-dimethyl-4-methoxy-2-pyridyl)methyl]sulfinyl]-1H-benzimidazole, 1-(pyridine-3-sulfonyl)-2-[[[3-methyl-4-(2,2,2-trifluoroethoxy)-2-pyridyl]methyl]sulfinyl]-1H-benzimidazole, 1-(pyridine-3-sulfonyl)-5-(difluoromethoxy)-2-[[(3,4-dimethoxy-2-pyridyl)methyl]sulfinyl]-1H-benzimidazole, 1-(pyridine-3-sulfonyl)-6-(difluoromethoxy)-2-[[(3,4-dimethoxy-2-pyridyl)methyl]sulfinyl]-1H-benzimidazole, 1-[4-[(morpholin-4-yl)phenyl]sulfonyl]-5-methoxy-2-[[(3,5-dimethyl-4-methoxy-2-pyridyl)methyl]sulfinyl]-1H-benzimidazole, 1-[4-[(morpholin-4-yl)phenyl]sulfonyl]-6-methoxy-2-[[(3,5-dimethyl-4-methoxy-2-pyridyl)methyl]sulfinyl]-1H-benzimidazole, N-[4-[[5-methoxy-2-[[(3,5-dimethyl-4-methoxy-2-pyridyl)methyl]sulfinyl]benzimidazol-1-yl]sulfonyl]phenyl]urea, N-[4-[[6-methoxy-2-[[(3,5-dimethyl-4-methoxy-2-pyridyl)methyl]sulfinyl]benzimidazol-1-yl]sulfonyl]phenyl]urea, N-(4-{[2-({[3-methyl-4-(2,2,2-trifluoroethoxy)-2-pyridyl]methyl}sulfinyl)benzimidazol-1-yl]sulfonyl}phenyl)urea, N-(4-{[2-({[4-(3-methoxypropoxy)-3-methyl-2-pyridyl]methyl}sulfinyl)benzimidazol-1-yl]sulfonyl}phenyl)urea, N-(4-{[2-{[(3,4-di(methoxy)-2-pyridyl)methyl]sulfinyl}-5-(difluoromethoxy)-benzimidazol-1-yl]sulfonyl}phenyl)urea, N-(4-{[2-{[(3,4-di(methoxy)-2-pyridyl)methyl]sulfinyl}-6-(difluoromethoxy)-benzimidazol-1-yl]sulfonyl}phenyl)urea, 2-[4-(3-Methoxy-propoxy)-3-methyl-pyridin-2-ylmethanesulfinyl]-1-(6,7,9,10,12,13,15,16-octahydro-5,8,11,14,17-pentaoxa-benzocyclopentadecene-2-sulfonyl)-1H-benzimidazole, 2-[3-Methyl-4-(2,2,2-trifluoro-ethoxy)-pyridin-2-ylmethanesulfinyl]-1-(6,7,9,10,12,13,15,16-octahydro-5,8,11,14,17-pentaoxa-benzocyclopentadecene-2-sulfonyl)-1H-benzimidazole, 5-Methoxy-2-(4-methoxy-3,5-dimethyl-pyridin-2-ylmethanesulfinyl)-1-(6,7,9,10,12,13,15,16-octahydro-5,8,11,14,17-pentaoxa-benzocyclopentadecene-2-sulfonyl)-1H-benzimidazole, 6-Methoxy-2-(4-methoxy-3,5-dimethyl-pyridin-2-ylmethanesulfinyl)-1-(6,7,9,10,12,13,15,16-octahydro-5,8,11,14,17-pentaoxa-benzocyclopentadecene-2-sulfonyl)-1H-benzimidazole, 5-Difluoromethoxy-2-(3,4-dimethoxy-pyridin-2-ylmethanesulfinyl)-1-(6,7,9,10,12,13,15,16-octahydro-5,8,11,14,17-pentaoxa-benzocyclopentadecene-2-sulfonyl)-1H-benzimidazole, 6-Difluoromethoxy-2-(3,4-dimethoxy-pyridin-2-ylmethanesulfinyl)-1-(6,7,9,10,12,13,15,16-octahydro-5,8,11,14,17-pentaoxa-benzocyclopentadecene-2-sulfonyl)-1H-benzimidazole, 2-{4-[(5-methoxy-2-{[(3,5-dimethyl-4-methoxy-2-pyridyl)methyl]sulfinyl}benzimidazol-1-yl)sulfonyl]phenoxy}acetamide, 2-{4-[(5-methoxy-2-{[(3,5-dimethyl-4-methoxy-2-pyridyl)methyl]sulfinyl}benzimidazol-1-yl)sulfonyl]phenoxy}-N-(2-pyridyl)acetamide, N-(carbamoylmethyl)-2-{4-[(5-methoxy-2-{[(3,5-dimethyl-4-methoxy-2-pyridyl)methyl]sulfinyl}benzimidazol-1-yl)sulfonyl]phenoxy}acetamide, 2-{4-[(6-methoxy-2-{[(3,5-dimethyl-4-methoxy-2-pyridyl)methyl]sulfinyl}benzimidazol-1-yl)sulfonyl]phenoxy}acetamide, 2-{4-[(6-methoxy-2-{[(3,5-dimethyl-4-methoxy-2-pyridyl)methyl]sulfinyl}benzimidazol-1-yl)sulfonyl]phenoxy}-N-(2-pyridyl)acetamide, N-(carbamoylmethyl)-2-{4-[(6-methoxy-2-{[(3,5-dimethyl-4-methoxy-2-pyridyl)methyl]sulfinyl}benzimidazol-1-yl)sulfonyl]phenoxy}acetamide, 2-(4-{[2-({[3-methyl-4-(2,2,2-trifluoroethoxy)-2-pyridyl]methyl}sulfinyl)benzimidazol-1-yl]sulfonyl}phenoxy)acetamide, 2-(4-{[2-({[3-methyl-4-(2,2,2-trifluoroethoxy)-2-pyridyl]methyl}sulfinyl)benzimidazol-1-yl]sulfonyl}phenoxy)-N-(2-pyridyl)acetamide, N-(carbamoylmethyl)-2-(4-{[2-({[3-methyl-4-(2,2,2-trifluoroethoxy)-2-pyridyl]methyl}sulfinyl)benzimidazol-1-yl]sulfonyl}phenoxy)acetamide, 2-{4-[(5-(difluoromethoxy)-2-{[(3,4-dimethoxy-2-pyridyl)methyl]sulfinyl}benzimidazol-1-yl)sulfonyl]phenoxy}acetamide, 2-{4-[(5-(difluoromethoxy)-2-{[(3,4-dimethoxy-2-pyridyl)methyl]sulfinyl}benzimidazol-1-yl)sulfonyl]phenoxy}-N-(2-pyridyl)acetamide, 6N-(carbamoylmethyl)-2-{4-[(5-(difluoromethoxy)-2-{[(3,4-dimethoxy-2-pyridyl)methyl]sulfinyl}benzimidazol-1-yl)sulfonyl]phenoxy}acetamide, 2-{4-[(6-(difluoromethoxy)-2-{[(3,4-dimethoxy-2-pyridyl)methyl]sulfinyl}benzimidazol-1-yl)sulfonyl]phenoxy}acetamide, 2-{4-[(6-(difluoromethoxy)-2-{[(3,4-dimethoxy-2-pyridyl)methyl]sulfinyl}benzimidazol-1-yl)sulfonyl]phenoxy}-N-(2-pyridyl)acetamide, N-(carbamoylmethyl)-2-{4-[(6-(difluoromethoxy)-2-{[(3,4-dimethoxy-2-pyridyl)methyl]sulfinyl}benzimidazol-1-yl)sulfonyl]phenoxy}acetamide, 2-(4-{[2-({[4-(3-methoxypropoxy)-3-methyl-2-pyridyl]methyl}sulfinyl)benzimidazol-1-yl]sulfonyl}phenoxy)acetamide, 2-(4-{[2-({[4-(3-methoxypropoxy)-3-methyl-2-pyridyl]methyl}sulfinyl)benzimidazol-1-yl]sulfonyl}phenoxy)-N-(2-pyridyl)acetamide, N-(carbamoylmethyl)-2-(4-{[2-({[4-(3-methoxypropoxy)-3-methyl-2-pyridyl]methyl}sulfinyl)benzimidazol-1-yl]sulfonyl}phenoxy)acetamide, 1-[[4-{3-(morpholin-4-yl)propoxy}phenyl)sulfonyl]-5-(difluoromethoxy)-2-[[(3,4-dimethoxy-2-pyridyl)methyl]sulfinyl]-1H-benzimidazole, 1-[[4-{3-(morpholin-4-yl)propoxy}phenyl]sulfonyl]-6-(difluoromethoxy)-2-[[(3,4-dimethoxy-2-pyridyl)methyl]sulfinyl]-1H-benzimidazole, 1-[[4-{3-(morpholin-4-yl) propoxy}phenyl]sulfonyl]-5-methoxy-2-[[(3,5-dimethyl-4-methoxy-2-pyridyl)methyl]sulfinyl]-1H-benzimidazole, 1-[[4-{3-(morpholin-4-yl) propoxy}phenyl]sulfonyl]-6-methoxy-2-[[(3,5-dimethyl-4-methoxy-2-pyridyl)methyl]sulfinyl]-1H-benzimidazole, 1-[[4-{3-(morpholin-4-yl)propoxy}phenyl]sulfonyl]-2-[(3-methyl-4-methoxypropoxy-2-pyridyl)methylsulfinyl]-1H-benzimidazole, 1-[[4-{3-(morpholin-4-yl) propoxy}phenyl]sulfonyl]-2-[(3-methyl-4-(2,2,2-trifluoroethoxy)-2-pyridyl)methylsulfinyl]-1H-benzimidazole, 1-[4-[2-(morpholin-4-yl)ethoxy]phenylsulfonyl]-2-[[[(4-(3-methoxypropoxy)-3-methyl-2-pyridyl]methyl]sulfinyl]-1H-benzimidazole, 1-[4-[2-(morpholin-4-yl)ethoxy]phenylsulfonyl]-5-(difluoromethoxy)-2-[[(3,4-dimethoxy-2-pyridyl)methyl]sulfinyl]-1H-benzimidazole, 1-[4-[2-(morpholin-4-yl)ethoxy]phenylsulfonyl]-5-methoxy-2-[[(3,5-dimethyl-4-methoxy-2-pyridyl)methylsulfinyl]]-1H-benzimidazole, 1-[4-[2-(morpholin-4-yl)ethoxy]phenylsulfonyl]-6-(difluoromethoxy)-2-[[(3,4-dimethoxy-2-pyridyl)methyl]sulfinyl]-1H-benzimidazole, 1-[4-[2-(morpholin-4-yl)ethoxy]phenylsulfonyl]-6-methoxy-2-[[(3,5-dimethyl-4-methoxy-2-pyridyl)methylsulfinyl]]-1H-benzimidazole, 1-[4-[2-(morpholin-4-yl)ethoxy]phenylsulfonyl]-2-[[[3-methyl-4-(2,2,2-trifluoroethoxy)-2-pyridyl]methyl]sulfinyl]-1H-benzimidazole, 1-[{(N,N-dimethylamino)methyl}benzene-4-sulfonyl]-5-methoxy-2-[[(3,5-dimethyl-4-methoxy-2-pyridyl)methyl]sulfinyl]-1H-benzimidazole, 1-[2-acetamido-4-methyl-5-thiazolylsulfonyl]-5-methoxy-2-[[(3,5-dimethyl-4-methoxy-2-pyridyl)methyl]sulfinyl]-1H-benzimidazole, 1-(thiophene-2-sulfonyl)-5-methoxy-2-[[(3,5-dimethyl-4-methoxy-2-pyridyl)methyl]sulfinyl]-1H-benzimidazole, 1-[{(N,N-dimethylamino)methyl}benzene-4-sulfonyl]-6-methoxy-2-[[(3,5-dimethyl-4-methoxy-2-pyridyl)methyl]sulfinyl]-1H-benzimidazole, 1-[2-acetamido-4-methyl-5-thiazolylsulfonyl]-6-methoxy-2-[[(3,5-dimethyl-4-methoxy-2-pyridyl)methyl]sulfinyl]-1H-benzimidazole, 1-(thiophene-2-sulfonyl)-6-methoxy-2-[[(3,5-dimethyl-4-methoxy-2-pyridyl)methyl]sulfinyl]-1H-benzimidazole, 1-(thiophene-2-sulfonyl)-2-[[[(4-(3-methoxypropoxy)-3-methyl-2-pyridyl]methyl]sulfinyl]-1H-benzimidazole, 1-(thiophene-2-sulfonyl)-5-(difluoromethoxy)-2-[[(3,4-dimethoxy-2-pyridyl)methyl]sulfinyl]-1H-benzimidazole, 1-(thiophene-2-sulfonyl)-6-(difluoromethoxy)-2-[[(3,4-dimethoxy-2-pyridyl)methyl]sulfinyl]-1H-benzimidazole, 1-(thiophene-2-sulfonyl)-]-2-[[[3-methyl-4-(2,2,2-trifluoroethoxy)-2-pyridyl]methyl]sulfinyl]-1H-benzimidazole, 1-(phenylmethylsulfonyl)-5-methoxy-2-[[(3,5-dimethyl-4-methoxy-2-pyridyl)methyl]sulfinyl]-1H-benzimidazole, 1-[(N,N-dimethylamino)benzene-4-sulfonyl]-5-methoxy-2-[[(3,5-dimethyl-4-methoxy-2-pyridyl)methyl]sulfinyl]-1H-benzimidazole, 1-(phenylmethylsulfonyl)-6-methoxy-2-[[(3,5-dimethyl-4-methoxy-2-pyridyl)methyl]sulfinyl]-1H-benzimidazole, 1-[(N,N-dimethylamino)benzene-4-sulfonyl]-6-methoxy-2-[[(3,5-dimethyl-4-methoxy-2-pyridyl)methyl]sulfinyl]-1H-benzimidazole, 1-(pyridine-3-sulfonyl)-2-[[(3-methyl-4-methoxypropoxy-2-pyridyl)methyl]sulfinyl]-1H-benzimidazole, 1-[4-(morpholin-4-yl)phenylsulfonyl]-2-[[[(4-(3-methoxypropoxy)-3-methyl-2-pyridyl]methyl]sulfinyl]-1H-benzimidazole, 1-benzenesulfonyl-2-[[(3-chloro-4-morpholino-2-pyridyl)methyl]sulfinyl]-5-methoxy-(1H)-benzimidazole, 1-benzenesulfonyl-2-[[[(4-(3-methoxypropoxy)-3-methyl-2-pyridyl]methyl]sulfinyl]-1H-benzimidazole, 1-benzenesulfonyl-2-[(3-methoxyphenyl)methylsulfinyl]-1H-benzimidazole, 1-benzenesulfonyl-2-[(3-methoxyphenyl)methylsulfinyl]imidazolo[5,4-c]pyridine, 1-benzenesulfonyl-2-[(3-methoxyphenyl)methylsulfinyl]imidazolo[4,5-c]pyridine, 1-benzenesulfonyl-2-[(3-methoxyphenyl)methylsulfinyl]-5-nitro-benzimidazole, 1-benzenesulfonyl-2-[{2-(dimethylamino)phenyl}methylsulfinyl]-1H-benzimidazole, 1-benzenesulfonyl-2-[[[4-(2,2,3,3,4,4,4-heptafluorobutyl)oxy]-2-pyridyl]methyl]sulfinyl]-1H-thieno[3,4-d]imidazole, 1-[4-[2-(morpholin-4-yl)ethoxy]phenylsulfonyl]-2-[(3-methoxyphenyl)methylsulfinyl]imidazolo{5,4-c}pyridine, 1-[4-[2-(morpholin-4-yl)ethoxy]phenylsulfonyl]-2-[{2-(dimethylamino)phenyl}methylsulfinyl]-1H-benzimidazole, 1-[[2-{2-(morpholin-4-yl)ethoxy}ethoxy]phenyl-4-sulfonyl]-5-methoxy-2-[[(3,5-dimethyl-4-methoxy-2-pyridyl)methyl]sulfinyl]-1H-benzimidazole, 1-[[2-{2-(morpholin-4-yl)ethoxy}ethoxy]phenyl-4-sulfonyl]-6-methoxy-2-[[(3,5-dimethyl-4-methoxy-2-pyridyl)methyl]sulfinyl]-1H-benzimidazole, 1-[[2-{2-(morpholin-4-yl)ethoxy}ethoxy]phenyl-4-sulfonyl]-2-[[[(4-(3-methoxypropoxy)-3-methyl-2-pyridyl]methyl]sulfinyl]-1H-benzimidazole, 1-[[2-{2-(morpholin-4-yl)ethoxy}ethoxy]phenyl-4-sulfonyl]-5-(difluoromethoxy)-2-[[(3,4-dimethoxy-2-pyridyl)methyl]sulfinyl]-1H-benzimidazole, 1-[[2-{2-(morpholin-4-yl)ethoxy}ethoxy]phenyl-4-sulfonyl]-6-(difluoromethoxy)-2-[[(3,4-dimethoxy-2-pyridyl)methyl]sulfinyl]-1H-benzimidazole, 1-[[2-{2-(morpholin-4-yl)ethoxy}ethoxy]phenyl-4-sulfonyl]-2-[[[3-methyl-4-(2,2,2-trifluoroethoxy)-2-pyridyl]methyl]sulfinyl]-1H-benzimidazole, 1-(4-acetaminobenzenesulfonyl)-5-methoxy-2-[[(3,5-dimethyl-4-methoxy-2-pyridyl)methyl]sulfinyl]-1H-benzimidazole, 1-(4-acetaminobenzenesulfonyl)-6-methoxy-2-[[(3,5-dimethyl-4-methoxy-2-pyridyl)methyl]sulfinyl]-1H-benzimidazole, 1-[(2-dimethylcarbamoyl-vinyl)benzene-4-sulfonyl]-5-methoxy-2-[(3,5-dimethyl-4-methoxy-2-pyridyl)methylsulfinyl]-1H-benzimidazole, -[(2-dimethylcarbamoyl-vinyl)benzene-4-sulfonyl]-6-methoxy-2-[(3,5-dimethyl-4-methoxy-2-pyridyl)methylsulfinyl]-1H-benzimidazole, 1-[(2-carbamoyl-vinyl)benzene-4-sulfonyl]-5-methoxy-2-[(3,5-dimethyl-4-methoxy-2-pyridyl)methylsulfinyl]-1H-benzimidazole, 1-[(2-carbamoyl-vinyl)benzene-4-sulfonyl]-6-methoxy-2-[(3,5-dimethyl-4-methoxy-2-pyridyl)methylsulfinyl]-1H-benzimidazole, sodium 2-[5-methoxy-2-(4-methoxy-3,5-dimethyl pyridin-2-yl methanesulfinyl)benzimidazole-1-sulfonyl]benzene sulfonate, sodium 2-[6-methoxy-2-(4-methoxy-3,5-dimethyl pyridin-2-yl methanesulfinyl)benzimidazole-1-sulfonyl]benzene sulfonate, {4-[5-methoxy-2-(4-methoxy-3,5-dimethyl-2-pyridinyl) methanesulfinyl benzimidazole-1-sulfonyl] phenoxy}acetic acid methyl ester, {4-[6-methoxy-2-(4-methoxy-3,5-dimethyl-2-pyridinyl) methanesulfinyl benzimidazole-1-sulfonyl] phenoxy}acetic acid methyl ester, 1-[(4-(2-dimethylaminoethoxy))benzenesulfonyl]-5-methoxy-2-[(3,5-dimethyl-4-methoxy-2-pyridyl) methylsulfinyl]-1H-benzimidazole, 1-[(4-(2-dimethylamino ethoxy))benzenesulfonyl]-6-methoxy-2-[(3,5-dimethyl-4-methoxy-2-pyridyl) methylsulfinyl]-1H-benzimidazole, N-(2-{4-[5-methoxy-2-(4-methoxy-3,5-dimethyl pyridin-2-yl methanesulfinyl)benzimidazole-1-sulfonyl]-phenoxy}ethyl)-N,N,N-trimethyl ammonium trifluoromethanesulfonate, N-(2-{4-[6-methoxy-2-(4-methoxy-3,5-dimethyl pyridin-2-yl methanesulfinyl)benzimidazole-1-sulfonyl]-phenoxy}ethyl)-N,N,N-trimethyl ammonium trifluoromethanesulfonate,.

2-{2-carbamoylmethoxy-4-[5-methoxy-2-((4-methoxy-3,5-dimethyl pyridin-2yl)methanesulfinyl)benzimidazole-1-sulfonyl]phenoxy}acetamide, 2-{2-carbamoylmethoxy-4-[6-methoxy-2-((4-methoxy-3,5-dimethyl pyridin-2-yl)methanesulfinyl)benzimidazole-1-sulfonyl]phenoxy}acetamide, 1,3-bis[5-methoxy-2-[((4-methoxy-3,5-dimethyl) pyridin-2-yl) methanesulfinyl]benzimidazole-1-sulfonyl]-benzene, 1,3-bis[6-methoxy-2-[((4-methoxy-3,5-dimethyl) pyridin-2-yl) methanesulfinyl]benzimidazole-1-sulfonyl]-benzene, 1-[5- methoxy-2-[((4-methoxy-3,5-dimethyl) pyridin-2-yl) methanesulfinyl]benzimidazole-1-sulfonyl]-3-[6-methoxy-2-[((4-methoxy-3,5-dimethyl) pyridin-2-yl) methanesulfinyl]benzimidazole-1-sulfonyl]-benzene, 1-[6-methoxy-2-[((4-methoxy-3,5-dimethyl) pyridin-2-yl) methanesulfinyl]benzimidazole-1-sulfonyl]-3-[5-methoxy-2-[((4-methoxy-3,5-dimethyl) pyridin-2-yl) methanesulfinyl]benzimidazole-1-sulfonyl]-benzene, sodium 2-[2-[[(4-methoxypropoxy-3-methyl) pyridin-2-yl]methanesulfinyl]benzimidazole-1-sulfonyl] benzenesulfonate, 2-(2-carbamoylmethoxy-4-{2-[4-(3-methoxypropoxy)-3-methyl pyridin-2-yl methylsulfinyl]benzimidazole-1-sulfonyl}phenoxy)acetamide, 2-{2-carbamoylmethoxy-4-[6-difluoromethoxy-2-(3,4-dimethoxy-pyridin-2-ylmethanesulfinyl)-benzimidazole-1-sulfonyl]-phenoxy}-acetamide, 2-{2-carbamoylmethoxy-4-[5-difluoromethoxy-2-(3,4-dimethoxy-pyridin-2-ylmethanesulfinyl)-benzimidazole-1-sulfonyl]-phenoxy}-acetamide, 2-(2-carbamoylmethoxy-4-{2-[3-methyl-4-(2,2,2-trifluoro-ethoxy)-pyridin-2-ylmethanesulfinyl)-benzimidazole-1-sulfonyl}-phenoxy)-acetamide, and 2-{2-[3-methyl-4-(2,2,2-trifluoro-ethoxy)-pyridin-2-ylmethanesulfinyl]-benzoimidazole-1-sulfonyl}-benzenesulfonic acid sodium salt.

The compounds of the invention can be prepared by the reacting the 2-pyridylmethylsulfinyl-1H-benzimidazole derivatives (or structurally related compounds) having a free NH group within the imidazole moiety, with an arylsulfonyl chloride. In the broad sense the benzimidazole or structurally related compound which is the starting material having the free NH group, can be described by Formula 1 wherein the $R_{15}$ group would be H. Similarly, in the broad sense the arylsulfonyl chloride reagent is described by the formula $R_{21}(R_{17})SO_2Cl$ where the $R_{21}$ and $R_{17}$ groups are defined as in connection with Formula 1. Reaction Scheme 1 discloses a process for preparing examplary preferred compounds of the invention by reacting the 2-pyridylmethylsulfinyl-1H-benzimidazole derivative of Formula 6 with a benzenesulfonyl chloride derivative of Formula 7 in the presence of a suitable base. The reaction is typically conducted in an inert organic solvent, such as dichloromethane in the presence of an organic base, such as triethylamine. For compounds of Formula 6 and Formula 7 the $R_1$–$R_3$, $R_6$–$R_9$ and $R_{17}$ groups are defined as in connection with Formula 1. As it can be seen in Reaction Scheme 1, the benzenesulphonylation reaction may give rise to two isomeric or tautomeric products depending on the nature and positions of the $R_6$–$R_9$ substituents on the benzimidazole ring. The two isomeric products (which may be merely tautomers) are shown in Formulas 8 and 9.

The benzenesulfonyl chloride derivatives of Formula 7 can be obtained in accordance with procedures well known in the art.

Those skilled in the art will recognize the 2-pyridylmethylsulfinyl-1H-benzimidazole derivatives of Formula 6 as the proton pump inhibitors generally known in the art and described for example in U.S. Pat. No. 4,686,230 (Rainer et. al.) and in published international application WO 97/48380 (Astra Aktiobiolag). Starting materials within the scope of Formula 13 include the known drugs LANSOPRAZOLE (U.S. Pat. No. 4,628,098), OMEPRAZOLE (U.S. Pat. Nos. 4,255,431 and 4,255,431), PANTOPRAZOLE (U.S. Pat. No. 4,758,579) and RABEPRAZOLE (U.S. Pat. No. 5,045,552) Thus, the starting-compounds of Formula 6 can be prepared in accordance with the state-of-the-art, for example as described in U.S. Pat. Nos. 4,686, 230, 4,628,098, 4,255,431, 4,758,579, 5,045,552, international application WO 97/48380, Journal of Medicinal Chemistry, 32, 1970–1977 (1989), Chem. Pharm. Bull. 38, 2853–2858 (1990), J. Med. Chem., 34, 1049–1062 (1991), Journal of Medicinal Chemistry, 35, 1049–1057 (1992), and Journal of Medicinal Chemistry, 35, 438–450 (1992), all of which are specifically incorporated herein by reference.

2-pyridylmethyl sulfide compounds of Formulas 10 and 11 to the corresponding sulfoxides. Those skilled in the art will recognize that Formulas 10 and 11 represent isomeric compounds which may be different or identical (tautomeric) with one another depending on the nature and position of the $R_6$–$R_9$ substituents. The oxidation reaction can be performed with oxidizing agents known in the art for forming

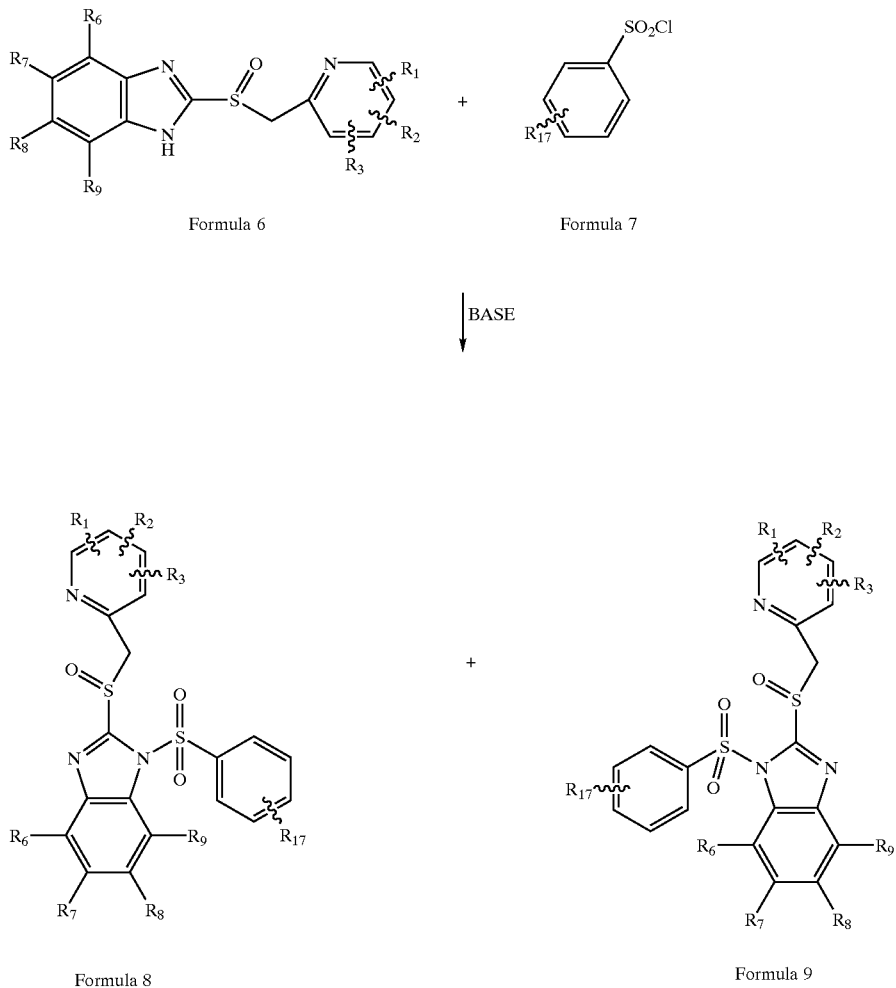

sulfoxides, for example hydrogen peroxide, m-chloroperoxybenzoic acid and iodosobenzene may serve for this purpose. The oxidation reaction is normally conducted in an aprotic neutral solvent, such as dichloromethane. The sulfide compounds of Formulas 10 and 11 can be obtained by performing a benzenesulphonylation reaction (in analogy to the reaction of Scheme 1) on the sulfide compounds having a free benzimidazole NH group, or their suitable salt. The latter sulfides having the free benzimidazole NH group can be obtained in accordance with the state-of-the-art.

Instead of using the free benzimidazole compounds of Formula 6, their suitable salts such as the sodium, potassium, magnesium (and other) salts can be reacted with the benzenesulfonyl chloride derivative of Formula 7, to also provide the exemplary compounds of the invention in accordance with Formulas 8 and 9.

Reaction Scheme 2 discloses an alternative method for preparing the exemplary compounds of the invention, shown in Formulas 8 and 9. This reaction involves the oxidation of the corresponding 1-(N)-benzenesulfonyl-benzimidazolyl, Reaction Scheme 2

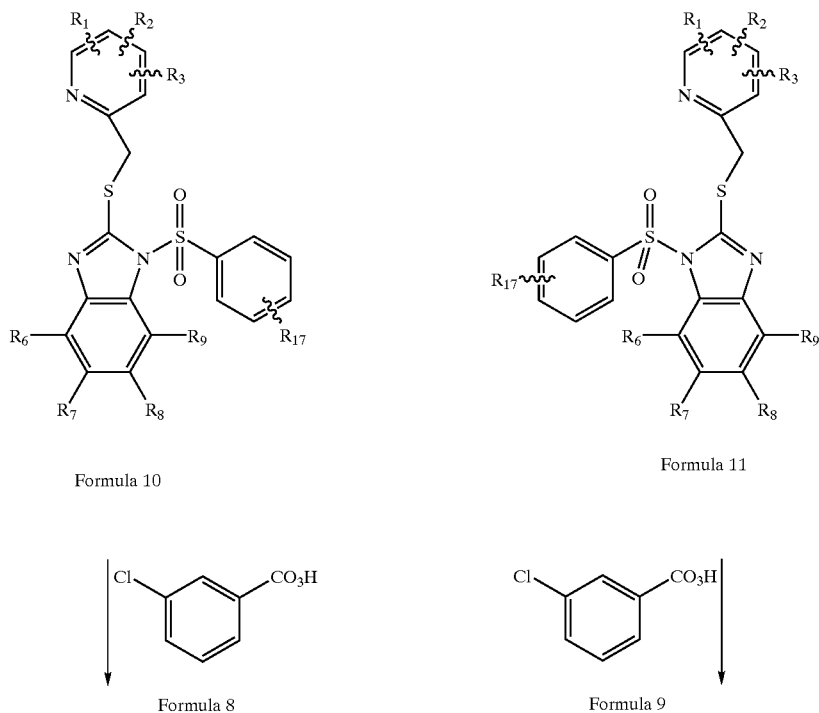

Formula 10

Formula 11

Formula 8

Formula 9

A significant advantage of the compounds of the present invention is that they can release the active forms of the proton pump inhibitors spontaneously by hydrolysis in the mammalian (including human) body. Hydrolysis can occur chemically or enzymatically. Because the compounds of this invention spontaneously release the active form of the proton pump inhibitor drugs by in vivo hydrolysis, they can attain longer duration of effective drug concentration in the body. Thus, the compounds of the present invention are prodrugs which are converted to active drugs by hydrolysis in the body, providing long duration of effective concentration. The long duration of inhibitory activity by spontaneous hydrolysis of the compounds of this invention allows more effective inhibition of gastric acid secretion, which enables better therapy of acid related disease as defined on pages 1 and 2. Compounds of this invention can be administered for inhibiting gastric acid secretion orally. The typical daily dose of the compounds will depend on various factors such as the individual requirement of each patient. In general, oral and parenteral dosages will be in the range of 5 to 100 mg per day.

Those skilled in the art will readily understand that for oral administration the compounds of the invention are admixed with pharmaceutically acceptable excipients which per se are well known in the art. Specifically, a drug to be administered systemically, it may be confected as a powder, pill, tablet or the like or as a syrup or elixir suitable for oral administration. Description of the subtances normally used to prepare tablets, powders, pills, syrups and elixirs can be found in several books and treatise well known in the art, for example in Remington's Pharmaceutical Science, Edition 17, Mack Publishing Company, Easton, Pa.

Compounds of the present invention can be combined with certain amounts of known proton pump inhibitors, e. g. LANSOPRAZOLE, OMEPRAZOLE, PANTOPRAZOLE, or RABEPRAZOLE, to provide a drug-prodrug combination, and the combination administered for inhibition of gastric acid secretion. Thus, initially the proton pump inhibitor (drug) inhibits gastric acid secretion of the patient. The aforesaid known and widely used proton pump inhibitors have 60–90 minutes of plasma half-life. As the effective concentration of the proton pump inhibitor (drug) is decreased by metabolism, the compound of the present invention (prodrug) continuosly undergoes hydrolysis and provides and maintains new active inhibitor concentration in the mammalian, including human body.

A disadvantage of the presently used proton pump inhibitors is that for therapy by injection in a liquid form they must be reconstituted from a lyophilized powder in a medium having the high pH of approximately 9.5. The prodrugs of the present invention overcome the disadvantage of requiring a reconstituting medium having such high pH, because the compounds of the present invention can be reconstituted to form an injectable liquid in a medium of approximately pH 6.0 to 8.5. It will be readily appreciated by those skilled in the art that for administration in liquid form by injection the liquid that reconstitutes the drug is a pharmaceutically acceptable aqueous solution that per se is known in the art. Such pharmaceutically acceptable solutions utilized for administration of drugs in injectable form are described for example in the treatise PHARMACEUTICAL DOSAGE FORMS (Parenteral Medications, Volume 1, Edited by K. E. Avis, H. A. Lieberman and L. Lachman (1992).

For example, an exemplary compound of the invention, such as 2-(2-carbamoylmethoxy-4-{2-[4-(3-methoxypropoxy)-3-methyl pyridin-2-yl methylsulfinyl]benzimidazole-1-sulfonyl}phenoxy)acetamide is dissolved in aqueous 40% 2-hydroxypropyl-beta-cyclodextrin solution buffered at pH 7.4, to provide a concentration of 8 mg per ml of the compound of the invention, The latter formulation is injectable intravenously at pH 7.4 and 2-hydroxypropyl-beta-cyclodextrin is known to be safe and non-toxic excreted unchanged in urine within 12 hours. If necessary to dissolve a compound of the invention 20% sulfobutyl ether-beta-cyclodextrin and 20% hydroxypropyl-beta-cyclodextrin can be used for increasing solubility, as suggested (for other drugs) by the publications (J. Clin. Pharm., 1998, 38 (7) 593–602, J. Pharm. Sci., 1997, 86(3) 335–339, J. Pharm. Sci., 1992, 81, 524–548, J. Pharm. Sci., 1999, 88, 1016–1020, and J. Pharm. Sci., 1999, 88, 1107–1111.).

Among the benefits of the pre-proton pump inhibitor (P-PPI) type of drugs of the present invention is their ability to provide more effective treatment of erosive esophagitis and of less severe reflux diseases as well. This is because effective treatment of erosive esophagitis (and to a lesser extent of lesser reflux diseases) requires prevention of the reflux of gastric contents at pH 3.0 or still lower pH. The current PPI drugs allow several acidic excursions to pH <2.0 per day, resulting in a moderate to weak amelioration of symptoms. However, healing would require elevation to pH >4.0 for about 16 hours per day or longer. When, as in current usual treatment by PPIs, the other 8 hours contain episodic acidity to pH 3.0 or less, the patients tend to continue to complain of pain. The more effective and more continues acid suppression by the drugs of the present invention is likely to result in substantially better treatment of this disease, as well as faster healing of all acid related erosions or ulcers.

The pre-proton pump inhibitor (P-PPI) type of drugs of the present invention provide improved dual therapy for *H. pylori* eradication. This is because the PPI's synergize with cell division dependent antibiotics such as amoxicillin (cell wall biosynthesis) and clarithromycin (protein synthesis) by elevating gastric surface pH to enable a larger fraction of the bacterial population to be in dividing phase during presentation of the antibiotic to the gastric lumen. However, their effect on intragastric pH is limited by their dwell time in the plasma. The pre-proton pump inhibitor (P-PPI) type of drugs of the present invention can continuously elevate intra gastric pH close to neutrality on current once a day therapy. Therefore, 100% eradication of the bacteria is expected in dual therapy with the prodrugs of the invention (for example a pro-drug of OMEPRAZOLE in accordance with the invention) plus an effective antibiotic, such as amoxicillin.

Even monotherapy for *H. pylori* eradication is likely to be successful with the pre-proton pump inhibitor (P-PPI) type of drugs of the present invention. This is because in the absence of acid, the enzyme *H. pylori* urease elevates environmental pH to >8.3, which is toxic to the organism. PPI's in current formulation inhibit growth or present of the organism in the antrum, due to elevation of antral pH to close to neutrality. Elevation of 24 hour pH to neutrality, as it can be accomplished with the drugs of the present invention, is likely to result in "self eradication" of the bacteria.

Approximately 30% of patients with gastrointestinal distress appear with symptoms without quantitative underlying disease (non-ulcer dyspepsia). The most likely cause for these symptoms is upper gastrointestinal afferent nerve sensitivity to gastric acid. Only acid ablation ameliorates these symptoms and this can be attained with the drugs of the present invention.

By way of concrete examples, the following tests and results are described. Certain compounds of the invention have been tested in one or more standard laboratory tests that demonstrate gastric antisecretory activity. The compounds of the invention did not directly inhibit the $K^+$-dependent ATP hydrolysis of gastric H,K-ATPase. However, after hydrolysis the compounds of this invention showed strong inhibition of gastric H,K-ATPase activity. This is consistent with the knowledge that the compounds obtained by hydrolysis e. g. LANSOPRAZOLE, OMEPRAZOLE, PANTOPRAZOLE and RABEPRAZOLE are well known H,K-ATPase inhibitors. For example, 1-benzenesulfonyl-5-methoxy-2-[(3,5-dimethyl-4-methoxy-2-pyridyl)methylsulfinyl]-1H-benzimidazole was tested for inhibitory activity of gastric H,K-ATPase. Initially this compound did not inhibit gastric H,K-ATPase. However, gastric H,K-ATPase activity was spontaneously inhibited as hydrolysis of this compound in aqueous solution at pH 7.4 proceeded. After 5.75 hr -hydrolysis at pH 7.4, this compound inhibited 91% of gastric H,K-ATPase activity, same as 5-methoxy-2-[(3,5-dimethyl-4-methoxy-2-pyridyl)methylsulfinyl]-1H-benzimidazole (OMEPRAZOLE) which was the product of the hydrolysis. It was determined that 1-benzenesulfonyl-5-methoxy-2-[(3,5-dimethyl-4-methoxy-2-pyridyl) methylsulfinyl]-H-benzimidazole was hydrolyzed to 5-methoxy-2-[(3,5-dimethyl-4-methoxy-2-pyridyl) methylsulfinyl]-1H-benzimidazole (OMEPRAZOLE) with a half-life ($t_{1/2}$) 3±0.5 hr at 37° C. at pH 7.4 in the presence of the plasma proteins. Another good example is 2-(2-carbamoylmethoxy-4-{2-[4-(3-methoxypropoxy)-3-methyl pyridin-2-yl methylsulfinyl]benzimidazole-1-sulfonyl}phenoxy)acetamide. The half life of this compound dependes on pH. At pH 2 the half-life of this compound is about 1.8 hr (which mimics in vivo gastric juice pH), at pH 7.4 in the presence of bovine serum albumin it is about 3.7 hr (which mimics blood plasma serum), at pH 8 it is about 10.7 hr (which mimics similar pH of duodenum), and at pH 7.4 without bovine serum albumin it is about 22.2 hr. This data show that this pro-drug compound of the invention is reasonably stable in the stomach compared to the parent RABEPRAZOLE, which has a half-life of a few minutes at pH 2. Based on these measured characteristics the compound 2-(2-carbamoylmethoxy-4-{2-[4-(3-methoxypropoxy)-3-methyl pyridin-2-yl methylsulfinyl] benzimidazole-1-sulfonyl}phenoxy)acetamide is expected to be well absorbed, and slowly release the parent RABEPRAZOLE in the blood, resulting in long-lasting in vivo activity. This compound can also be administered intravenously in an aqueous solution at pH 7.4 which solution may include 2-hydroxypropyl-β-cyclodextrin.

When a mixture of 2-{4-[(5-methoxy-2-{[(3,5-dimethyl-4-methoxy-2-pyridyl)methyl]sulfinyl}benzimidazol-1-yl) sulfonyl]phenoxy}-N-(2-pyridyl)acetamide and 2-{4-[(6-methoxy-2-{[(3,5-dimethyl-4-methoxy-2-pyridyl)methyl] sulfinyl}benzimidazol-1-yl)sulfonyl]phenoxy}-N-(2-pyridyl)acetamide was orally administrated to male rat, 5-methoxy-2-[[(3,5-dimethyl-4-methoxy-2-pyridyl)methyl] sulfinyl]-1H-benzimidazole (OMEPRAZOLE) was continuously released to the plasma for more than 4 hours as a result of the hydrolysis of 2-{4-[(5-methoxy-2-{[(3,5-dimethyl-4-methoxy-2-pyridyl)methyl]sulfinyl }benzimidazol-1-yl) sulfonyl]phenoxy}-N-(2-pyridyl)acetamide and 2-{4-[(6-methoxy-2-{[(3,5-dimethyl-4-methoxy-2-pyridyl)methyl] sulfinyl}benzimidazol-1-yl)sulfonyl]phenoxy}-N-(2-pyridyl)acetamide. As a control experiment, when OMEPRAZOLE was administrated to male rat, OMEPRAZOLE has completely disappeared from the plasma within 1.5 hr. Bioavailability of2-{4-[(5-methoxy-2-{[(3,5-dimethyl-4-methoxy-2-pyridyl)methyl]sulfinyl] benzimidazol-1-yl)sulfonyl]phenoxy}-N-(2-pyridyl) acetamide was much higher than that of OMEPRAZOLE after oral administration.

Additional experiments, described below, with further compounds of the invention showed good inhibition of gastric acid secretion. For example, when a mixture of 2-{2-carbamoylmethoxy-4-[5-methoxy-2-((4-methoxy-3,5-dimethyl pyridin-2-yl)methanesulfinyl)benzimidazole-1-sulfonyl]phenoxy}acetamide and 2-{2-carbamoylmethoxy-4-[6-methoxy-2-((4-methoxy-3,5-dimethyl pyridin-2-yl)methanesulfinyl)benzimidazole-1-sulfonyl]phenoxy}acetamide (1:1 mixture of isomers) was administrated to male rat, gastric acid secretion was observed to be significantly and continuously inhibited. Using pylorus-ligated male rats, when acid-output stimulated by histamine was measured, intraduodenal administration of 10 μmole of 2-{2-carbamoylmethoxy-4-[5-methoxy-2-((4-methoxy-3,5-dimethyl pyridin-2-yl)methanesulfinyl)benzimidazole-1-sulfonyl]phenoxy}acetamide and 2-{2-carbamoylmethoxy-4-[6-methoxy-2-((4-methoxy-3,5-dimethyl pyridin-2-yl)methanesulfinyl)benzimidazole-1-sulfonyl]phenoxy}acetamide (1:1 mixture of isomers) provided 64.2% inhibition, while OMEPRAZOLE provided only 54.6% under identical condition. Also, when acid-output stimulated by histamine and carbachol was measured after 5.5 hr of oral administration, the latter mixture of isomers provided 49.7% inhibition, while OMEPRAZOLE provided only 19.6% inhibition. Under similar condition, (pyridine-3-sulfonyl)OMEPRAZOLE (the compound of Example 25) inhibited 61% and a mixture of 2-{4-[(5-methoxy-2-{[(3,5-dimethyl-4-methoxy-2-pyridyl)methyl]sulfinyl } benzimidazol-1-yl)sulfonyl]phenoxy} acetamide and 2-{4-[(6-methoxy-2-{[(3,5-dimethyl-4-methoxy-2-pyridyl)methyl]sulfinyl} benzimidazol-1-yl)sulfonyl]phenoxy}acetamide inhibited 65%, while OMEPRAZOLE showed relatively rapid decline of inhibition (about 20%) with fast elimination of drug in the plasma level. Similarly, 2-(2-carbamoylmethoxy-4-{2-[4-(3-methoxypropoxy)-3-methyl pyridin-2-yl methylsulfinyl]benzimidazole-1-sulfonyl}phenoxy)acetamide provided 56% inhibition after 5 hr of oral administration, while the parent RABEPRAZOLE showed 32% of inhibition under the same condition. 2-(4-{[2-({[3-Methyl-4-(2,2,2-trifluoroethoxy)-2-pyridyl]methyl}sulfinyl) benzimidazol-1-yl]sulfonyl}phenoxy) acetamide provided 46.9% inhibition and 2-(2-carbamoylmethoxy-4-{2-[3-methyl-4-(2,2,2-trifluoroethoxy)-pyridin-2-yl methanesulfinyl]-benzimidazole-1-sulfonyl}-phenoxy)-acetamide gave 36.8% inhibition, while the parent LANSOPRAZOLE showed only 29% inhibition after 4 hour of oral administration.

It is well known that oral potency of OMEPRAZOLE without enteric-coating is significantly lower than that found after i.v. or i.d. administration in both rat and dog (Larsson et al., Scand. J. Gastroenterology, vol. 20 (suppl. 108), 23–35, 1985). The compounds of this invention do not need enteric-coating for protection from acid-catalyzed decomposition. Furthermore, the compounds of this invention provide continuous inhibition of gastric acid secretion, as described above.

SPECIFIC EMBODIMENTS AND EXPERIMENTAL DESCRIPTION

Preparation of Intermediates

Intermediate Example 1

Preparation of [(morpholin-4-yl)alkoxy]benzene-4-sulfonyl chloride

[(morpholin-4-yl) alkoxy] benzene-4-sulfonyl chloride was prepared by chlorosulfonylation of 4-[(phenoxy) alkoxy]morpholine using chlorosulfonic acid in the presence of dichloromethane or chloroform. In this reaction, chloroform or dichloromethane was important to avoid the cleavage of ether linkage of alkoxybenzene moiety by chlorosulfonic acid.

[3-(Morpholin-4-yl) propoxy] benzene-4-sulfonyl chloride was prepared by chlorosulfonylation of 4-(3-phenoxypropyl)morpholine using chlorosulfonic acid in the presence of dichloromethane or chloroform. For example, to a solution of 2.2 g (10 mmole) of N-(3-phenoxypropyl) morpholine in 20 ml of chloroform, 2 ml of chlorosulfonic acid (30 mmole) was slowly added at −10° C. and stirred for 30 min. The reaction mixture was stirred at room temperature for 5 hr. Chloroform was removed from lower layer. Lower layer was treated with chopped-ice to give solids. To a mixture of ice and solid product, 10 g of sodium phosphate (tribasic) was added and stirred with cooling. Chlorosulfonyl compound was extracted with dichloromethane (300 ml). Dichloromethane extract was dried over anhydrous magnesium sulfate and evaporated under reduced pressure. 1.6 g of [3-(morpholin-4-yl) propoxy]benzene-4-sulfonyl chloride was obtained.

[2-(Morpholin-4-yl)ethoxy]benzene-4-sulfonyl chloride was prepared using N-(2-phenoxyethyl) morpholine by similar reaction described above. For example, 7.2 g of N-(2-phenoxyethyl)morpholine HCl salt was resuspended in 20 ml of dichloromethane and 7 ml of chlorosulfonic acid was slowly introduced with cooling by ice-jacket. The reaction mixture was stirred at 0° C. for 2 hr, then, at room temperature overnight. Dichloromethane (350 ml) was added to the reaction mixture and excess chlorosulfonic acid was destroyed by adding icy water(about 100 g). Aqueous layer was adjusted to pH 8.5 by concentrated sodium carbonate solution with cooling by ice. Dichloromethane was dried over anhydrous magnesium sulfate and evaporated under reduced pressure to give 8.1 g of [2-(morpholin-4-yl) ethoxy]benzene-4-sulfonyl chloride. M.P. 48–50° C.

N-(2-Phenoxyethyl) morpholine was prepared by a modified method of Grail. et al (Journal of American Chemical Society, 1952, 74, 1313–1315). For example, 9.2 g of phenol and 18.6 g of N-(2-chloroethyl)morpholine HCl salt were dissolved in 120 ml of isopropanol and 12 g of potassium hydroxide was added with cooling. The reaction mixture was refluxed for 12 hours. Solid (KCl) was filtered off. The filtrate was distilled off. The residual material was treated with 150 ml of 1N NaOH, then, extracted with dichloromethane (200 ml). Dichloromethane layer was again washed with a solution of 0.1N sodium carbonate in 10% NaCl solution. Dichloromethane layer was dried over anhydrous magnesium chloride, and evaporated under reduced pressure. Residual syrup was dissolved in 100 ml of 1.5N HCl solution, and washed with 100 ml of chloroform. Aqueous layer was treated with 100 ml of toluene and water was removed by Dean-Stark apparatus by distillation. Residual toluene layer was cooled to give crystalline solid, which was collected by filtration. 12 g of N-[(2-phenoxy) ethyl]morpholine HCl salt (50% yield )was obtained.

N-[3-(Phenoxy)propyl] morpholine was prepared by a reaction of 3-(phenoxy)propyl bromide with morpholine. For example, 3-(phenoxy)propyl bromide (7.8 ml, 50 mmole) was added to morpholine (8 ml) in toluene (50 ml) and refluxed overnight. NaOH solution (2 g of NaOH in 20 ml of water) was added and additionally refluxed for 4 hr. Toluene was removed by distillation under reduced pressure. Residue was treated with dichloromethane(200 ml) and water(200 ml). Dichloromethane layer was dried and concentrated. Residue was treated with dichloromethane-heptane to give 7 g of 4-[3-(phenoxy)propyl] morpholine.

[2-{2-(Morpholin-4-yl)ethoxy}ethoxy]benzene-4-sulfonyl chloride was prepared using 4-[2-[2-(phenoxy)ethoxy]ethyl]morpholine by a similar reaction described above. For example, 2-(phenoxy)ethanol (4.0 ml) was added to 5.4 g of N-(2-chloroethyl)morpholine hydrochloride and 6 g of sodium tert-butoxide in 70 ml of toluene. The reaction mixture was refluxed for 16 hr. EtOAc (100 ml) was added and washed with water (200 ml). Organic layer was separated, and again, extracted with 0.5N HCl solution (120 ml). Aqueous layer was washed again with chloroform (30 ml), then, was adjusted to pH 10.5 by adding NaOH solution. The product, [2-[2-(morpholin-4-yl)ethoxy]ethoxy]benzene, was extracted with dichloromethane (200 ml) from water. Organic layer was again washed with water, dried over anhydrous magnesium sulfate, and concentrated under reduced pressure. The product, [2-[2-(morpholin-4-yl)ethoxy]ethoxy]benzene, was obtained as a yellow syrup (5.4 g). TLC analysis showed over 99% purity and the structure was confirmed by NMR. The syrupy product was used in situ for preparing [2-{2-(morpholin-4-yl)ethoxy} ethoxy] benzene-4-sulfonyl chloride. 5.0 g of 2-[2-(morpholin-4-yl)ethoxy]ethoxybenzene was dissolved in 70 ml of dichloromethane. In ice bath, chlorosulfonic acid (7 ml) was slowly added. The reaction mixture was stirred at room temperature overnight. Two layers were separated. Chloroform layer, upper layer, was removed. Pale brown syrup, lower layer, was added to 100 g of chopped ice. Dichloromethane (200 ml) was added, and concentrated sodium carbonate solution was slowly added upto pH 9 under 4° C. with good stirring. Dichloromethane layer was separated, dried over anhydrous magnesium sulfate, and evaporated under reduced pressure. Yellow syrup was obtained, which was dried in vacuo. 3.8 g of [2-{2-(morpholin-4-yl)ethoxy}ethoxy]benzene-4-sulfonyl chloride was obtained.

Intermediate Example 2

Preparation of [2-(dimethylamino)ethoxy]phenyl-4-sulfonyl chloride 2 g of N,N-dimethyl-N-[(2-phenoxy)ethyl]amine was dissolved in 10 ml of dichloromethane and 3 ml of chlorosulfonic acid was slowly added under ice cooling. The mixture was stirred at room temperature for 3 hr and poured into ice. Dichloromethane (100 ml) was added and aqueous layer was neutralized by concentrated sodium carbonate solution with keeping temperature under 4° C. Dichloromethane layer was dried over anhydrous magnesium sulfate and evaporated under reduced pressure. 0.8 g of [2-(dimethylamino)ethoxy]phenyl-4-sulfonyl chloride was obtained.

Intermediate Example 3

Preparation of N-[4-(chlorosulfonyl)phenyl]urea

N-[4-(chlorosulfonyl)phenyl]urea was prepared by a known method (R. J. W. Cremlyn, D. Leonard, and R. Motwani (1973) J. Chem. Soc., Perkin 1500–503).

Chlorosulfonic acid (4.4 ml) was added to phenylurea (2.7 g) in an ice bath, then, warmed to 60° C. for 3 hr. The syrup was poured on chopped ice with good mixing. Solid was separated and dried in vacuo. 2.3 g of product was obtained. M.P. 138–141° C.

Intermediate Example 4

Preparation of N-[(p-chlorosulfonyl)phenyl]morpholine

N-[(p-Chlorosulfonyl)phenyl] morpholine was synthesized by a modified method of Cremlyn, et al. (R. J. Cremlyn, J. P. Bassin, S. Farouk, M. Potterton, and T. Mattu. (1992) Phosphorus, Sulfur, and Silicon, Vol., 73, pp. 107–120).

10 g of 4-phenyl morpholine in 50 ml of chloroform was added to 25 ml of chlorosulfonic acid in a ice-jacket. The reaction mixture was stirred at reflux for 7 hr. Brown syrup was poured into dichloromethane (150 ml) and chopped ice (100 g) with stirring, and neutralized by saturated sodium phosphate, tribasic, with ice-cooling. Collect dichloromethane layer, dried over anhydrous magnesium sulfate. Organic solvent was evaporated under reduced pressure to give yellow solid, which was dried in vacuo. 6.1 g of product was obtained. M. P. 154–156° C.

Intermediate Example 5

Preparation of pyridine-3-sulfony choride

Pyridine-3-sulfonyl chloride was prepared by a method of Alo, et al. (B. I. Alo, O. B. Familoni, F. Marsais, and G. Queguiner, (1992) Journal of Heterocyclic Chemistry, vol. 29, pp 61–64.)

24 g of phosphorus pentachloride was added to a suspension of 15 g of pyridine-3-sulfonic acid in 30 ml of phosphorus oxychloride and heated at 120° C. for 12 hr. The reaction mixture was concentrated by distillation under reduced pressure, and treated with toluene. Solid obtained was collected and dried in vacuo. 16.7 g of product was obtained. M. P. 138–141° C.

Intermediate Example 6

Preparation of m-(chlorosulfonyl)benzo-15-crown-5-ether

To an ice-cold solution of benzo-15-crown-5-ether (536.6 mg, 2 mmole) in 5 ml of chloroform and cooled in ice-bath, 0.3 ml of chlorosulfonic acid (4.5 mmole) was slowly added. The reaction mixture was stirred in ice bath for 2 hr, then, 5 hr at room temperature. The reaction mixture was added to chopped ice and extracted with dichloromethane (50 ml). Combined organic layer was dried over magnesium chloride, and evaporated. 374 mg of product was obtained. M.P. 79–84° C.

m-(Chlorosulfonyl)benzo-18-crown-6-ether was prepared using same method as described above. Yield was about 46%. M. P. 108–110° C.

Intermediate Example 7

Preparation of 2-[p-(chlorosulfonyl)phenoxy]-N-(2-pyridyl)acetamide 1.32 g of 2-(phenoxyacetyl)aminopyridine HCl salt (5 mmole) was resuspended in 10 ml of dichloromethane and 2 ml of chlorosulfonic acid was added in ice-bath to give clear solution. The solution was stirred at room temperature for 3 hr. The reaction mixture was added to ice-water with good stirring to give white solids. The solids were filtered, washed with acetonitrile, and dried in vacuo. 0.65 g of solid was obtained. M. P. 170–175° C. (decomposition)

Intermediate Example 8

Preparation of p-(Dimethylamino)methylbenzenesulfonyl chloride

N,N-Dimethyl benzylamine (7 ml) was dissolved in 40 ml of dichloromethane and chlorosulfonic acid (12 ml) was slowly added at 0° C. The reaction mixture was stirred at room temperature for 4 hours. The reaction mixture was poured into ice to give solids, which was collected by filtration. 2.63 g of the titled compound was obtained. Additional crops (1.34 g) was obtained from the dichloromethane extraction of the filtrate.

1H NMR (CDCl$_3$) δ: 2.96 (s, 6H), 4.60 (s, 2H), 7.38–7.52 (m, 4H)

Intermediate Example 9

Preparation of 2-[p-(chlorosulfonyl)phenoxy] acetamide 3.0 g of 2-(phenoxy)acetamide was dissolved in 10 ml of dichloromethane and 6 ml of chlorosulfonic acid was slowly added at 0 ° C. The reaction mixture was stirred at room temperature for 10 hr. Dichloromethane was evaporated under reduced pressure. Residual material was poured on chopped ice. Solid was collected by filtration and dried in vacuo. 3.9 g of product was obtained. M.P. 166–171° C. (decomposition)

Intermediate Example 10

Preparation of p-(dimethylamino)benzenesulfonyl chloride

N,N-Dimethylaniline (8 ml) was dissolved in 20 ml of chloroform, and chlorosulfonic acid (20 ml) was slowly added with cooling. The reaction mixture was refluxed for 6 hr. The reaction mixture was cooled and poured on ice (100 g). Dichloromethane (120 ml) was added and aqueous layer was neutralized by concentrated sodium carbonate solution with keeping temperature below 4 ° C. Organic layer was again washed with ice-cold 0.1N sodium bicarbonate solution, and dried over anhydrous magnesium sulfate. Organic layer was concentrated under reduced pressure. Residual material was crystallized from ethyl ether-heptane to give yellowish green solid. p-(Dimethylamino) benzenesulfonyl chloride (4.2 g) was obtained. M. P. 108–111° C.

Intermediate Example 11

Preparation of N-(carbamoylmethyl)-2-[4-(chlorosulfonyl)phenoxy]acetamide a) Preparation of N-(carbamoylmethyl)-2-(phenoxy) acetamide Glycinamide HCl salt (5 g) was resuspended in 200 ml of dichloromethane and 14 ml of triethylamine at 4° C. Phenoxyacetyl chloride (6 ml) was slowly added with good stirring. The reaction mixture was stirred at room temperature for 3 hr, then, refluxed for 3 hr. The reaction mixture was cooled to give crystalline solid, which was collected by filtration. Filtered solid was washed with water, and dried in vacuo to give 7.5 g of product, N-(carbamoylmethyl)-2-(phenoxy)acetamide. The filtrate was washed with water, and 0.1N sodium carbonate solution. The filtrate was concentrated, and treated with ether to give additional product, 1.2 g of N-(carbamoylmethyl)-2-(phenoxy)acetamide. M.P. 138–140° C.

b) Preparation of N-(carbamoylmethyl)-2-[4-(chlorosulfonyl)phenoxy]acetamide N-(carbamoylmethyl)-2-(phenoxy)acetamide (2.08 g) was resuspended in 30 ml of dichloromethane and chlorosulfonic acid (6 ml) was slowly added with cooling. The reaction mixture was stirred at room temperature for 2 hr. Two layers separated after standing for 10 min without stirring. Upper layer was decanted. Lower layer was poured to chopped ice (60 g) with good mixing to give white solid, which was collected by filtration and washed with ice-cold water. The solid was dried in vacuo to give 2.78 g of N-(carbamoylmethyl)-2-[4-(chlorosulfonyl)phenoxy]acetamide.

M.P. 97–100° C. (decomposition)

Intermediate Example 12

Preparation of(4-chlorosulfonyl phenoxy)acetic acid methyl ester

Phenoxyacetic acid (1.8 g) was slowly added to chlorosulfonic acid (4 ml) with ice-cooling. The reaction mixture was stirred at room temperature for 2 hours. The reaction mixture was poured into a mixture of dichloromethane(50 ml) and methanol(5 ml) at 0° C., and stirred for 15 min. The organic layer was washed with water, 10% sodium bicarbonate solution, and saturated sodium chloride solution. The dichloromethane layer was dried over anhydrous magnesium sulfate, and evaporated under reduced pressure to give 1.2 g of the titled compound.

1H NMR (CDCl$_3$) δ: 3.81 (s, 3H), 4.73 (s, 2H), 7.02 (d, 2H), 7.96 (d, 2H).

Intermediate Example 13

Preparation of(4-chlorosulfonyl phenoxy)acetic acid methyl ester

Phenoxyacetic acid (1.8 g) was slowly added to chlorosulfonic acid (4 ml) with ice-cooling. The reaction mixture was stirred at room temperature for 2 hours. The reaction mixture was poured into a mixture of dichloromethane(50 ml) and methanol(5 ml) at 0° C., and stirred for 15 min. The organic layer was washed with water, 10% sodium bicarbonate solution, and saturated sodium chloride solution. The dichloromethane layer was dried over anhydrous magnesium sulfate, and evaporated under reduced pressure to give 1.2 g of the titled compound.

1H NMR (CDCl$_3$) δ: 3.81 (s, 3H), 4.73 (s, 2H), 7.02 (d, 2H), 7.96 (d, 2H)

Intermediate Example 14

Preparation of N-(p-(chlorosulfonyl)phenoxyethyl)-N,N,N-trimethylammonium trifluoromethanesulfonate Methyl trifluoromethanesulfonate (1 ml) was added to p-(2-dimethylamino)ethoxybenzenesulfonyl chloride (0.8 g) in a solvent composed of dichloromethane (5 ml) and acetonitrile(5 ml). The reaction mixture was stirred at room temperature for 1 day and concentrated under reduced pressure. The concentrate provided crystalline product, which was washed with hexane, and dried in vacuo. Hygroscopic pale brown solid (1.2 g) was obtained.

1H NMR (CD$_3$CN) δ: 3.17 (s, 9H), 3.75 (t, 2H), 4.53 (t, 2H), 7.21 (d, 2H), 8.05 (d, 2H)

Intermediate Example 15

Preparation of 3,4-bis(carbamoylmethoxy) benzenesulfonyl chloride 1,2-Bis(carbamoylmethoxy)benzene was prepared by a known method (H-S Kim. et al., (1998) J. Heterocyclic Chem., 35, 177–181). 1,2-Bis(carbamoylmethoxy)benzene (4.4 g) was added to chlorosulfonic acid (13 ml) at 0° C. with good stirring. Chloroform (4 ml) was added and warmed to about 60° C. for 2 hours. The reaction mixture was poured into chopped ice. The precipitates were collected, and washed with cold water. The solids were again washed with acetonitrile, and dried in vacuo to yield the title compound (4.9g).

1H NMR (DMSO-d6) δ: 4.45 (s, 4H), 6.88 (s, 1H), 7.15 (d, 2H), 7.47 and 8.95 (br, two -NH$_2$)

EXAMPLE 1

1-Benzenesulfonyl-5-methoxy-2-[(3,5-dimethyl-4-methoxy-2-pyridyl)methylsulfinyl]-1H-benzimidazole and 1-Benzensulfonyl-6-methoxy-2-[(3,5-dimethyl-4-methoxy-2-pyridyl)methylsulfinyl]-1H-benzimidazole Method A: 5-Methoxy-2-[(3,5-dimethyl-4-methoxy-2-pyridyl)methylsulfinyl]-1H-benzimidazole(172 mg, 0.5 mmole) was dissolved in 20 ml of dichloromethane and 0.140 ml of triethylamine. The solution was cooled to 0–4° C. in an ice bucket. Benzenesulfonyl chloride (96 mg, 0.55 mmole) was slowly added and stirred at 0–4° C. with thin layer chromatography monitoring (developing solvent system: chloroform-methanol (10:1) and acetonitrile-chloroform (1:1)). After the reaction was complete, the organic layer was washed with an aqueous solution composed of 0.1M NaCl, and 0.1M sodium phosphate, pH 8.5. The organic layer was dried over anhydrous magnesium sulfate and concentrated under reduced pressure. The residual material was crystallized from dichloromethane-ethyl ether-heptane to provide 127 mg of product. M.p. 87–89° C. (decomposition). Heptane was introduced to the remaining organic layer to provide a second crop of product (104 mg). After combining the solids, 231 mg of the product (yield 95%) was obtained. The product was composed of an mixture of 1-benzensulfonyl-5-methoxy-2-[(3,5-dimethyl-4-methoxy-2-pyridyl)methylsulfinyl]-1H-benzimidazole and 1-benzensulfonyl-6-methoxy-2-[(3,5-dimethyl-4-methoxy-2-pyridyl)methylsulfinyl]-1H-benzimidazole (3:2 ratio by NMR) 1H NMR (CDCl$_3$, δ: 8.10–8.15 (m, 3H), 7.45–7.80(m, 5H), 7.0–7.1(m, 1H), 4.8–5.0(2q, 2AB total 2H), 3.83 and 3.92 (2s, total 3H), 3.75(s, 3H), 2.31(s, 3H), 2.23(s, 3H)

Method B: A mixture of 1-benzenesulfonyl-5-methoxy-2-[(3,5-dimethyl-4-methoxy-2-pyridyl)methylthio]-1H-benzimidazole and 1-benzenesulfonyl-6-methoxy-2-[(3,5-dimethyl-4-methoxy-2-pyridyl)methylthio]-1H-benzimidazole was prepared by reacting 5-methoxy-2-[(3,5-dimethyl-4-methoxy-2-pyridyl)methylthio]-1H-benzimidazole with benzenesulfonyl chloride as in method A. I-Benzenesulfonyl-5-methoxy-2-[(3,5-dimethyl-4-methoxy-2-pyridyl)methylthio]-1H-benzimidazole was isolated by silica gel column chromatography and used in the next step as follows. 1-Benzenesulfonyl-5-methoxy-2-[(3,5-dimethyl-4-methoxy-2-pyridyl)methylthio]-1H-benzimidazole (318 mg, 1 mmole) in 30 ml of dichloromethane was cooled to −20° C. A dichloromethane solution (5 ml) containing m-chloroperbenzoic acid (equivalent to 1 mmole from 60% purity) was slowly added. The reaction was monitored by thin layer chromatography. After 5 hours the organic layer was washed with an aqueous solution of 0.1M sodium bicarbonate and 50 mM sodium thiosulfate. The organic layer was dried over anhydrous magnesium sulfate and concentrated under reduced pressure. Residual material was solidified from dichloromethane-ethyl ether-heptane to provide 397 mg of product (yield 82%), 1-benzenesulfonyl-5-methoxy-2-[(3,5-dimethyl-4-methoxy-2-pyridyl)methylsulfinyl]-1H-benzimidazole and 1-benzenesulfonyl-6-methoxy-2-[(3,5-dimethyl-4-methoxy-2-pyridyl)methylsulfinyl]-1H-benzimidazole.

EXAMPLES 2–19

The compounds listed under Examples 2–19 below were prepared using the method A as described in Example 1. 2-Pyridylmethylsulfinyl benzimidazole compounds were reacted with the corresponding arylsulfonyl chloride to give the corresponding 1-arylsulfonyl-2-pyridylmethylsulfinyl benzimidazoles as shown in Table 1 with reference to Formula 12.

TABLE 1

Formula 12

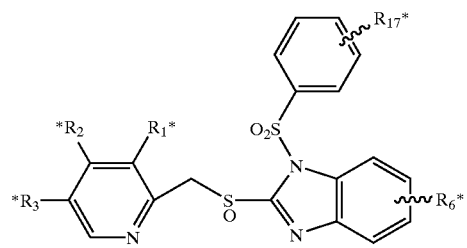

| # | R$_6$* | R$_1$* | R$_2$* | R$_3$* | R$_{17}$* | Yield (%) | m.p. (° C.) |
|---|---|---|---|---|---|---|---|
| 2 | 5- and 6 OCH$_3$[1] | —CH$_3$ | —OCH$_3$ | —CH$_3$ | 4-Cl | 81 | 76–78 |
| 3 | 5- and 6 OCH$_3$[1] | —CH$_3$ | —OCH$_3$ | —CH$_3$ | 4-Br | 73 | 84–86 |
| 4 | 5- and 6 OCH$_3$[1] | —CH$_3$ | —OCH$_3$ | —CH$_3$ | 4-F | 85 | 70–72 |
| 5 | 5- and 6 OCH$_3$[1] | —CH$_3$ | —OCH$_3$ | —CH$_3$ | 4-CH$_3$ | 79 | 64–66 |
| 6 | 5- and 6 OCH$_3$[1] | —CH$_3$ | —OCH$_3$ | —CH$_3$ | 4-OCH$_3$ | 83 | 85–87 |
| 7 | 5- and 6 OCH$_3$[1] | —CH$_3$ | —OCH$_3$ | —CH$_3$ | 3-CF$_3$ | 67 | 65–67 |
| 8 | 5- and 6 OCH$_3$[1] | —CH$_3$ | —OCH$_3$ | —CH$_3$ | 4-OCF$_3$ | 78 | 63–64 |
| 9 | H | —CH$_3$ | OCH$_2$CF$_3$ | H | H | 78 | 80–83 |
| 10 | H | —CH$_3$ | OCH$_2$CF$_3$ | H | 4-Cl | 79 | 90–92 |
| 11 | H | —CH$_3$ | OCH$_2$CF$_3$ | H | 4-Br | 71 | 105–107 |
| 12 | H | —CH$_3$ | OCH$_2$CF$_3$ | H | 4-F | 73 | 85–87 |

TABLE 1-continued

Formula 12

| # | $R_6$* | $R_1$* | $R_2$* | $R_3$* | $R_{17}$* | Yield (%) | m.p. (° C.) |
|---|---|---|---|---|---|---|---|
| 13 | H | —CH$_3$ | OCH$_2$CF$_3$ | H | 4-CH$_3$ | 67 | 125–126 |
| 14 | H | —CH$_3$ | OCH$_2$CF$_3$ | H | 4-OCH$_3$ | 78 | 94–95 |
| 15 | H | —CH$_3$ | OCH$_2$CF$_3$ | H | 3-CF$_3$ | 67 | 123–125 |
| 16 | H | —CH$_3$ | OCH$_2$CF$_3$ | H | 4-OCF$_3$ | 78 | 125–126 |
| 17[2] | 5- and 6 OCHF$_2$ | OCH$_3$ | OCH$_3$ | H | H | 92 | 51–54 |
| 18[2] | 5- and 6 OCHF$_2$ | OCH$_3$ | OCH$_3$ | H | 4-OCH$_3$ | 87 | 67–69 |
| 19[2] | 5- and 6 OCHF$_2$ | OCH$_3$ | OCH$_3$ | H | 4-OCF$_3$ | 87 | 61–63 |

[1]signifies a 3:2 ratio of 5- OCH$_3$ and 6-OCH$_3$
[2]signifies a 5:4 ratio of 5- OCHF$_2$ and 6-OCHF$_2$

EXAMPLE 20

5-Difluoromethoxy-2-[(3,4-dimethoxy-2-pyridyl)methylsulfinyl]-1H-benzimidazole, sodium salt sesquihydrate (432 mg, 1 mmole) was suspended in 30 ml of dichloromethane in the presence of anhydrous sodium carbonate (100 mg). 4-Chlorobenzenesulfonyl chloride (211 mg, 1 mmole) was added to the suspension and stirred at 4° C. overnight. The organic layer was separated by filtration and concentrated under reduced pressure. The residual solid was crystallized from dichloromethane-ethyl ether-heptane. 417 mg of isomer, 1-(4-chlorobenzenesulfonyl)-5-difluoromethoxy-2-[(3,4-dimethoxy-2-pyridyl)methylsulfinyl]-1H-benzimidazole and 1-(4-chlorobenzenesulfonyl)-6-difluoromethoxy-2-[(3,4-dimethoxy-2-pyridyl)methylsulfinyl]-1H-benzimidazole (5:4 ratio by NMR), was obtained. Yield 74.5% M.P. 82–83° C.

1H NMR (CDCl$_3$, δ: 8.05–8.15(m, 2H), 8.0(d, 1H), 7.78–7.81(m, 1H), 7.45–7.6(m, 2H), 7.2–7.3(m, 1H), 6.80–6.81(d, 1H), 6.5–6.6(d, 1H), 4.9–5.0(q, 2H), 3.93(s, 3H).

EXAMPLES 21–24

The compounds listed in Table 2, with reference to Formula 12, were prepared using the method described in Example 20.

TABLE 2

| # | $R_6$* | $R_1$* | $R_2$* | $R_3$* | $R_{17}$* | Yield (%) | m.p. (° C.) |
|---|---|---|---|---|---|---|---|
| 21[1] | 5-and 6 OCHF$_2$ | OCH$_3$ | OCH$_3$ | H | 4-Br | 87 | 80–82 |
| 22[1] | 5-and 6 OCHF$_2$ | OCH$_3$ | OCH$_3$ | H | 4-F | 78 | 67–70 |
| 23[1] | 5-and 6 OCHF$_2$ | OCH$_3$ | OCH$_3$ | H | 4-CH$_3$ | 88 | 73–75 |
| 24[1] | 5-and 6 OCHF$_2$ | OCH$_3$ | OCH$_3$ | H | 3-CF$_3$ | 83 | 62–66 |

[1]signifies a 5:4 ratio of 5-OCHF$_2$ and 6-OCHF$_2$

EXAMPLE 25

1-(Pyridine-3-sulfonyl)-5-methoxy-2-[[(3,5-dimethyl-4-methoxy-2-pyridylmethyl]sulfinyl]-1H-benzimidazole and 1-(pyridine-3-sulfonyl-6-methoxy-2-[[(3,5-dimethyl-4-methoxy-2-pyridyl)methyl]sulfinyl]-1H-benzimidazole 5-Methoxy-2[[(3,5-dimethyl-4-methoxy-2-pyridyl)methyl]sulfinyl]-1H-benzimidazole (344 mg) was dissolved in 20 ml of dichloromethane and 1 ml of triethylamine. Pyridine-3-sulfonyl chloride (195 mg) was added and stirred in ice-bath for 3 hr. Dichloromethane layer was washed with an aqueous solution composed of 0.1M NaCl and 0.1M sodium bicarbonate. Dichloromethane layer was dried over anhydrous magnesium sulfate. Solvent was removed under reduced pressure. Residual material was precipitated by dichloromethane-ethyl ether-heptane to provide 372 mg of product, which were a mixture of 1-(pyridine-3-sulfonyl)-5-methoxy-2-[[(3,5-dimethyl-4-methoxy-2-pyridyl)methyl]sulfinyl]-1H-benzimidazole and 1-(pyridine-3-sulfonyl)-6-methoxy-2-[[(3,5dimethyl-4-methoxy-2-pyridyl)methyl]sulfinyl]-1H-benzimidazole (3:1 ratio by NMR).

M.P. 136–138° C. (decomposition)

NMR (CDCl$_3$, δ): 2.27 (s, 3H), 2.35 (s, 3H), 3.82 (s, 3H), 3.86 & 3.93 (2s, total 3H), 5.04–5.17 (q, AB, 2H), 7.01–7.02 (dd, 1H), 7.47–7.56 (m, 2H), 7.67–7.71 (d, 1H), 8.15 (s, 1H), 8.51–8.55 (dd, 1H), 8.85–8.88 (d, 1H), 9.34 (s, 1H)

EXAMPLE 26

1-(Pyridine-3-sulfonyl)-2-[[[3-methyl-4-(2,2,2-trifluoroethoxy)-2-pyridyl]methyl]sulfinyl]-1H-benzimidazole 2-[[[3-Methyl-4-(2,2,2-trifluoroethoxy)-2-pyridyl]methyl]sulfinyl]-1H-benzimidazole (370 mg) was dissolved in 20 ml of dichloromethane and 1 ml of triethylamine. Pyridine-3-sulfonyl chloride (195 mg) was added and stirred in ice-bath for 5 hr. Dichloromethane layer was washed with an aqueous solution composed of 0.1M NaCl and 0.1M sodium bicarbonate. Dichloromethane layer was dried over anhydrous magnesium sulfate. Solvent was removed under reduced pressure. Residual material was precipitated by dichloromethane-ethyl ether-heptane to provide 348 mg of 1-(pyridine-3-sulfonyl)-2-[(3-methyl-4-(2,2,2-trifluoroethoxy)-2-pyridyl)methylsulfinyl]-1H-benzimidazole.

M.P. 118–120° C. (decomposition)

NMR (CDCl$_3$, δ): 2.35 (s, 3H), 4.38–4.49 (q, 2H), 4.98–5.22 (q, AB, 2H), 6.73 (d, 1H), 7.41–7.56 (m, 3H), 7.80–8.02 (dd, 2H), 8.23 (s, 1H), 8.52 (dd, 1H), 8.87 (dd, 1H), 9.36 (s, 1H)

EXAMPLE 27

1-(Pyridine-3-sulfonyl)-5-(difluoromethoxy)-2-[[(3.4-dimethoxy-2-pyridyl)methyl]sulfinyl]-1H-benzimidazole and 1-(pyridine-3-sulfonyl)-6-(difluoromethoxy)-2-[[(3,4-dimethoxy-2-pyridyl) methyl]sulfinyl]-1H-benzimidazole 5-(difluoromethoxy)-2-[[(3,4-dimethoxy-2-pyridyl) methyl]sulfinyl]-1H-benzimidazole (383 mg) was dissolved in 20 ml of dichloromethane and 1 ml of triethylamine. Pyridine-3-sulfonyl chloride (195 mg) was added and stirred in ice-bath for 5 hr. Dichloromethane layer was washed with an aqueous solution composed of 0.1M NaCl and 0.1M sodium bicarbonate. Dichloromethane layer was dried over anhydrous magnesium sulfate. Solvent was removed under reduced pressure. Residual material was precipitated by dichloromethane-ethyl ether-heptane to provide 397 mg of a mixture of 1-(pyridine-3-sulfonyl)-5-(difluoromethoxy)-2-[[(3,4-dimethoxy-2-pyridyl)methyl]sulfinyl]-1H-benzimidazole and 1-(pyridine-3-sulfonyl)-6-(difluoromethoxy)-2-[[(3,4-dimethoxy-2-pyridyl)methyl] sulfinyl]-1H-benzimidazole (ratio 3:2 by NMR).

M.P. 127–128° C. (decomposition)

EXAMPLE 28

Preparation of 1-(morpholin-4-yl)phenylsulfonyl-5-methoxy-2-[[(3,5-dimethyl-4-methoxy-2-pyridyl) methyl]sulfinyl]-1H-benzimidazole and 1-(morpholin-4-yl)phenylsulfonyl-6-methoxy-2-[f(3,5-dimethyl-4-methoxy-2-17 pyridyl)methyl]sulfinyl-1H-benzimidazole 270.8 mg of 4-(p-chlorosulfonyl)phenyl morpholine was added to 344 mg of 5-Methoxy-2-[[(3,5-dimethyl-4-methoxy-2-pyridyl)methyl]sulfinyl]-1H-benzimidazole in 20 ml of dichloromethane and 0.5 ml of triethylamine. The reaction mixture was stirred at room temperature overnight. Dichloromethane layer was washed with water, and dried over anhydrous magnesium sulfate. Organic layer was evaporated. Residual material was lyophilized in vacuo to give 425 mg of the titled product (1:1 ratio by NMR).

m.p.; 76–79 ° C. (decomposition)

EXAMPLE 29

Preparation of N-[4-[[5-methoxy-2-[[(3,5-dimethyl-4-methoxy-2-pyridyl)methyl]sulfinyl]benzimidazol-1-yl]sulfonyl]phenyl]urea and N-[4-[[6-methoxy-2-[[(3,5-dimethyl-4-methoxy-2-pyridyl)methyl] sulfinyl]benzimidazol-1-yl]sulfonyl]phenyl]urea 128 mg of N-[4-(chlorosulfonyl)phenyl]urea was added to 172 mg of 5-Methoxy-2-[[(3,5-dimethyl-4-methoxy-2-pyridyl)methyl]sulfinyl]-1H-benzimidazole in a mixture of 0.5 ml of triethylamine and 10 ml of dichloromethane-acetonitrile (50/50). The reaction mixture was stirred at room temperature overnight. Dichloromethane (20 ml) was added and washed with water, and 0.1M sodium bicarbonate solution. Organic layer was dried over anhydrous magnesium sulfate and evaporated. Residue was dissolved in 2 ml of dichloromethane and ethyl ether was added for crystallization. Crystals were collected and dried. 190 mg of product was obtained. The product was composed of a mixture of N-[4-[[5-methoxy-2-[[(3,5-dimethyl-4-methoxy-2-pyridyl)methyl]sulfinyl]benzimidazol-1-yl]sulfonyl] phenyl]urea and N-[4-[[6- methoxy-2-[[(3,5-dimethyl-4-methoxy-2-pyridyl)methyl]sulfinyl]benzimidazol-1-yl] sulfonyl]phenyl]urea (4:3 ratio by NMR).

m.p.; 154–158° C. (decomposition)

NMR (CDCl$_3$, δ): 2.19 (s, 3H), 2.20 & 2.21 (2s, total 3H), 3.69 & 3.70 (2s, total 3H), 3.76 & 3.89 (2s, total 3H), 4.75–4.94 (q, AB, 2H), 5.6–5.7 (br, NH$_2$), 6.95–7.08 (d, 1H), 7.05 (s, 1H), 7.43–7.86 (m, 5H), 8.12 (s, 1H), 9.0 (br, NH)

EXAMPLE 30

Preparation of N-(4-{[2-({[3-methyl-4-(2,2,2-trifluoroethoxy)-2-pyridyl]methyl}sulfinyl) benzimidazol-1-yl]sulfonyl}phenyl)urea 2-[[[3-Methyl-4-(2,2,2-trifluoroethoxy)-2-pyridyl] methyl]sulfinyl]-1H-benzimidazole (185 mg) dissolved in 30 ml of dichloromethane and 0.4 ml of triethylamine was added to 128 mg of N-[4-(chlorosulfonyl)phenyl]urea. The reaction mixture was stirred at room temperature overnight. The reaction mixture was washed with water and 0.1N sodium bicarbonate solution.

Organic layer was dried over anhydrous magnesium sulfate, and concentrated under reduced pressure. Residue was dissolved in 2 ml of dichloromethane and ethyl ether was added for precipitation. 125 mg of the titled product was obtained.

M.P. 115° C. (decomposition)

NMR (CDCl$_3$, δ): 2.25 (s, 3H), 4.37–4.42 (q, 2H), 4.6–4.85 (q, AB, 2H), 6.67 (d, 1H), 7.35–7.42 (m, 2H), 7.61–7.75 (m, 3H), 7.89–8.05 (m, 2H), 8.27–8.38 (m, 2H)

EXAMPLE 31

Preparation of 5-methoxy-2-(4-methoxy-3,5-dimethyl-pyridin-2-ylmethanesulfinyl)-1-(6,7,9,10, 12,13,15,16-octahydro-5,8,11,14,17-pentaoxa-benzocyclopentadecene-2-sulfonyl)-1H-benzimidazole and 6-methoxy-2-(4-methoxy-3,5-dimethyl-pyridin-2-ylmethanesulfinyl)-1-(6,7,9,10, 12,13,15,16-octahydro-5,8,11,14,17-pentaoxa-benzocyclopentadecene-2-sulfonyl-1H-benzimidazole 170 mg of 5-methoxy-2-[[(3,5-dimethyl-4-methoxy-2-pyridyl)methyl]sulfinyl]-1H-benzimidazole and 190 mg of m-(chlorosulfonyl) benzo-15-crown-5-ether were dissolved in 0.2 ml of triethylamine and 20 ml of dichloromethane. The reaction mixture was stirred at room temperature overnight. Organic layer was washed with water and dried over anhydrous magnesium sulfate. Solvent was removed to give syrup, which was lyophilized. 210 mg of the titled product, a mixture of 5-methoxy-2-(4-methoxy-3,5-dimethyl-pyridin-2-ylmethanesulfinyl)-1-(6,7,9,10,12,13,15,16-octahydro-5,8,11,14,17-pentaoxa-benzocyclopentadecene-2-sulfonyl)-1H-benzimidazole and 6-methoxy-2-(4-methoxy-3,5-dimethyl-pyridin-2-ylmethanesulfinyl)-1-(6,7, 9,10,12,13,15,16-octahydro-5,8,11,14,17-pentaoxa-benzocyclopentadecene-2-sulfonyl)-1H-benzimidazole (1:1 ratio by NMR), was obtained. Lyophilized product showed M.P. 76–80° C. with decomposition. NMR (CDCl$_3$, δ): 2.21 (s, 3H), 2.31 (s, 3H), 3.68–3.73 (m, 8H), 3.74 (s, 3H), 3.84–3.87 (m, 4H), 3.90 (s, 3H), 4.10–4.13 (m, 4H), 4.81–4.95 (2q, 2AB, 2H), 6.84 (d, 1H), 7.00–7.07 (dd, 1H), 7.25 (d, 1H), 7.42–7.72 (m, 3H), 8.15 (s, 1H)

EXAMPLE 32

Preparation of 2-[3-Methyl-4-(2,2,2-trifluoro-ethoxy)-pyridin-2-ylmethanesulfinyl]-1-(6,7,9,10,12,13,15,16-octahydro-5,8,11,14,17-pentaoxa-benzocyclopentadecene-2-sulfonyl)-1H-benzimidazole 2-[[[3 -Methyl-4-(2,2,2-trifluoroethoxy)-2-pyridyl]methyl]sulfinyl]-1H-benzimidazole (185 mg) dissolved in 20 ml of dichloromethane and 0.2 ml of triethylamine was added to 190 mg of m-(chlorosulfonyl) benzo-15-crown-5-ether. The reaction mixture was stirred at room temperature overnight. Organic layer was washed with water and dried over anhydrous magnesium sulfate. Solvent was removed to give syrup, which was lyophilized. 231 mg of the titled product was obtained. Lyophilized product showed M.P. 76–80° C. with decomposition.

NMR (CDCl$_3$, δ): 2.33 (s, 3H), 3.66–3.73 (m, 8H), 3.83–3.87 (m, 4H), 4.10–4.12 (m, 4H), 4.35–4.41 (q, 2H), 4.84–5.05 (q, AB, 2H), 6.61 (d, 1H), 6.86 (d, 1H), 7.37–7.45 (m, 2H), 7.56 (s, 1H), 7.71–7.74 (dd, 2H), 7.95 (d, 1H), 8.23 (d, 1H)

EXAMPLE 33

Preparation of 2-{4-[(5-methoxy-2-{[(3,5-dimethyl-4-methoxy-2-pyridyl)methyl]sulfinyl}benzimidazol-1-yl)sulfonyl]phenoxy}-N-(2-pyridyl)acetamide and 2-{4-[(6-methoxy-2-{[(3.5-dimethyl-4-methoxy-2-pyridyl)methyl]sulfinyl}benzimidazol-1-yl)sulfonyl]phenoxy}-N-(2-pyridyl)acetamide 170 mg of 2-[p-(chlorosulfonyl)phenoxy]-N-(2-pyridyl)acetamide was added to 172 mg of 5-methoxy-2-[[(3,5-dimethyl-4-methoxy-2-pyridyl)methyl]sulfinyl]-1H-benzimidazole dissolved in dichloromethane (15 ml) and triethylamine (0.4 ml). The reaction mixture was stirred at room temperature overnight. The reaction mixture was washed with water. Organic layer was dried over anhydrous magnesium sulfate, and evaporated. Residual material was lyophilized in vacuo to give 244 mg of the titled product, which was a mixture of 2-{4-[(5-methoxy-2-{[(3,5-dimethyl-4-methoxy-2-pyridyl)methyl]sulfinyl}benzimidazol-1-yl)sulfonyl]phenoxy}-N-(2-pyridyl)acetamide and 2-{4-[(6-methoxy-2-{[(3,5-dimethyl-4-methoxy-2-pyridyl)methyl]sulfinyl}benzimidazol-1-yl)sulfonyl]phenoxy} -N-(2-pyridyl)acetamide (2:1 ratio by NMR).

M.P. 76–80° C.

NMR (CDCl$_3$, δ): 2.21 & 2.23 (2s, total 3H), 2.32 (s, 3H), 3.74 & 3.75 (2s, total 3H), 3.83 & 3.93 (2s, total 3H), 4.65 (s, 2H), 4.83–4.92 (q, AB, 2H), 6.99–7.11 (m, 5H), 7.46 (d, 1H), 7.68–7.88 (m, 2H), 8.75 (br, NH)

EXAMPLE 34

Preparation of 2-(4-{[2-({[3-methyl-4-(2,2,2-trifluoroethoxy)-2-pyridyl]methyl}sulfinyl)benzimidazol-1-yl]sulfonyl}phenoxy)-N-(2-pyridyl)acetamide 2-[[ [3-Methyl-4-(2,2,2-trifluoroethoxy)-2-pyridyl]methyl]sulfinyl]-1H-benzimidazole (185 mg) dissolved in 20 ml of dichloromethane and 0.2 ml of triethylamine was added to 170 mg of 2-[p-(chlorosulfonyl)phenoxy]-N-(2-pyridyl)acetamide. The reaction mixture was washed with water. Organic layer was dried over anhydrous magnesium sulfate, and evaporated. Residual material was lyophilized to give 237 mg of the titled product. M.P. 78–81° C.

NMR (CDCl$_3$, δ): 2.31 (s, 3H), 4.34–4.40 (q, 2H), 4.71 (s, 2H), 4.84–5.05 (q, AB, 2H), 6.62 (d, 1H), 7.09 (d, 2H), 7.29–7.47 (m, 2H), 7.62–7.80 (m, 2H), 7.98 (d, 1H), 8.11 (d, 2H), 8.20–8.29 (m, 4H), 8.92 (br, NH)

EXAMPLE 35

Preparation of 2-{4-[(5-(difluoromethoxy)-2-{[(3,4-dimethoxy-2-pyridyl)methyl]sulfinyl}benzimidazol-1-yl)sulfonyl]phenoxy}-N-(2-pyridyl)acetamide and 2-{4-[(6-(difluoromethoxy)-2-{[(3,4-dimethoxy-2-pyridyl)methyl]sulfinyl}benzimidazol-1-yl)sulfonyl]phenoxy}-N-(2-pyridyl)acetamide 5-(difluoromethoxy)-2-[[(3,4-dimethoxy-2-pyridyl)methyl]sulfinyl]-1H-benzimidazole (192 mg) dissolved in 20 ml of dichloromethane and 0.2 ml of triethylamine was added to 170 mg of 2-[(p-chlorosulfonyl)phenoxyacetyl]aminopyridine. The reaction mixture was washed with water. Organic layer was dried over anhydrous magnesium sulfate, and evaporated. Residual material was lyophilized to give 187 mg of the titled product, which was a mixture of 2-{4-[(5-(difluoromethoxy)-2-{[(3,4-dimethoxy-2-pyridyl)methyl]sulfinyl} benzimidazol-1-yl)sulfonyl]phenoxy}-N-(2-pyridyl)acetamide and 2-{4-[(6-(difluoromethoxy)-2-{[(3,4-dimethoxy-2-pyridyl)methyl]sulfinyl}benzimidazol-1-yl)sulfonyl]phenoxy}-N-(2-pyridyl)acetamide (2:1 ratio by NMR).

M.P. 95–101 ° C.

NMR (CDCl$_3$, δ): 3.90 (s, 3H), 3.93 (s, 3H), 4.67 (s, 2H), 4.85–5.00 (2q, 2AB, 2H; s like, 1H), 6.52–6.80 (m, 2H), 7.08 (m, 3H), 7.29–7.40 (d, 1H), 7.58–7.80 (m, 2H), 7.97–8.16 (m, 3H), 8.22 (d, 1H), 8.30 (d, 1H), 8.82 (br, NH)

EXAMPLE 36

Preparation of 1-[4-(3-(morpholin-4-yl) propoxy) benzenesulfonyl]-5-(difluoromethoxy)-2-[[(3,4-dimethoxy-2-pyridyl)methyl]sulfinyl]-1H-benzimidazole and 1-[4-(3-(morpholin-4-yl) propoxy) benzenesulfonyl]-6-(difluoromethoxy)-2-[[(3,4-dimethoxy-2-pyridyl)methyl]sulfinyl]-1H-benzimidazole 180 mg of 4-(3-(morpholin-4-yl) propoxy) benzenesulfonyl chloride was added to a solution of 190 mg of 5-(difluoromethoxy)-2-[[(3,4-dimethoxy-2-pyridyl)methyl]sulfinyl]-1H-benzimidazole in 10 ml of dichloromethane and 0.5 ml of triethylamine. The reaction mixture was stirred overnight, and washed with water. Organic layer was concentrated and lyophilized in vacuo. 210 mg of the titled mixture was obtained (1:1 ratio by NMR).

EXAMPLE 37

Preparation of 1-[4-[3-(morpholin-4-yl) propoxy]benzenesulfonyl]-5-methoxy-2-[[(3,5-dimethyl-4-methoxy-2-pyridyl)methyl]sulfinyl]-1H-benzimidazole and 1-[4-[3-(morpholin-4-yl) propoxy]benzenesulfonyl]-6-methoxy-2-[[(3.5-dimethyl-4-methoxy-2-pyridyl)methyl]sulfinyl]-1H-benzimidazole 200 mg of 4-[3-(morpholin-4-yl) propoxy] benzenesulfonyl chloride was added to a solution of 200 mg of 5-methoxy-2-[[(3,5-dimethyl-4-methoxy-2-pyridyl) methyl]sulfinyl]-1H-benzimidazole in 10 ml of dichloromethane and 0.5 ml of triethylamine. The reaction mixture was stirred overnight, and washed with water. Organic layer was concentrated and treated with ethyl ether to give solids. Solids were crystallized from dichloromethane and ether. 210 mg of the titled product, 1:1 ratio of 5-methoxy and 6-methoxy compound, was obtained.

M.P. 98–102° C. (decomposition)

NMR (CDCl$_3$, δ): 1.97–2.05 (m, 2H), 2.09 (s, 3H), 2.20 (s, 3H) 3.05–3.15 (m, 6H), 3.58 (s, 3H), 3.65–3.80 (m, 4H), 3.81 & 3.92 (2s, total 3H), 3.82–3.95 (t, 2H), 4.73–4.94 (q, AB, 2H), 6.89–6.91 (d, 2H), 7.4–7.6 (m, 3H), 7.79–8.0 (m, 2H), 8.17 (s, 1H)

EXAMPLE 38

Preparation of a mixture of 1-[(4-dimethylaminomethyl)benzenesulfonyl]-5-methoxy-2-[(3,5-dimethyl-4-methoxy-2-pyridyl) methylsulfinyl]-1H-benzimidazole and 1-[(4-dimethylaminomethyl)benzenesulfonyl]-6-methoxy-2-[(3,5-dimethyl-4-methoxy-2-pyridyl) methylsulfinyl]-1H-benzimidazole 5-Methoxy-2-[(3,5-dimethyl-4-methoxy-2-pyridyl) methylsulfinyl]-1H-benzimidazole (344 mg) was dissolved in 35 ml of dichloromethane and 0.5 ml of triethylamine. To this solution, 4-(dimethylaminomethyl)benzenesulfonyl chloride (233 mg) was added and stirred overnight at room temperature. Dichloromethane layer was washed with water and dried over anhydrous magnesium sulfate. After removing dichloromethane under reduced pressure, the residual material was lyophilized in vacuo to give 403 mg of the titled compounds (1:1 of 5-methoxy /6-methoxy isomer).

1H NMR (CDCl$_3$) δ: 2.22 (s, 3H), 2.26 (s, 3H), 3.00 (s, 6H), 3.73 (s, 3H), 3.80 and 3.91 (s, s; 5-methoxy and 6-methoxy), 4.77–4.99 (q, 2H), 6.54–6.60 (m, 2H), 6.93–8.21 (m, 6H)

EXAMPLE 39

Preparation of 1-[2-acetamido-4-methyl-5-thiazolylsulfonyl]-5-methoxy-2-[[(3,5-dimethyl-4-methoxy-2-pyridyl)methyl]sulfinyl]-1H-benzimidazole 172 mg of 5-methoxy-2-[[(3,5-dimethyl-4-methoxy-2-pyridyl)methyl]sulfinyl]-1H-benzimidazole was dissolved in 10 ml of dichloromethane and 0.4 ml of triethylamine, and 128 mg of 2-acetamido-4-methyl-5-thiazolyl sulfonyl chloride was added. The reaction mixture was stirred at room temperature for 15 hr. Product spot was shown at slightly higher position than 5-methoxy-2-[[(3,5-dimethyl-4-methoxy-2-pyridyl)methyl]sulfinyl]-1H-benzimidazole in thin layer chromatography (developing solvent: dichloromethane-acetonitrile-methanol=100: 10: 5). Product was separated by silica gel column chromatography. 145 mg of the titled product was isolated.

EXAMPLE 40

Preparation of 1-(thiophene-2-sulfonyl)-5-methoxy-2-[[(3,5-dimethyl-4-methoxy-2-pyridyl)methyl] sulfinyl]-1H-benzimidazole and 1-(thiophene-2-sulfonyl)-6-methoxy-2-[[(3.5-dimethyl-4-methoxy-2-pyridyl)methyl]sulfinyl]-1H-benzimidazole 172 mg of 5-methoxy-2-[[(3,5-dimethyl-4-methoxy-2-pyridyl)methyl]sulfinyl]-1H-benzimidazole was dissolved in 10 ml of dichloromethane and 0.2 ml of triethylamine. 95 mg of thiophene-2-sulfonyl chloride was added. The reaction mixture was stirred at room temperature for 16 hr. Dichloromethane layer was washed with water and concentrated under reduced pressure. Residual material was crystallized from acetonitrile-ethyl ether-hexane. 225 mg of the titled product, a mixture of 1-(thiophene-2-sulfonyl)-5-methoxy-2-[[(3,5-dimethyl-4-methoxy-2-pyridyl)methyl] sulfinyl]-1H-benzimidazole and 1-(thiophene-2-sulfonyl)-6-methoxy-2-[[(3,5-dimethyl-4-methoxy-2-pyridyl)methyl] sulfinyl]-1H-benzimidazole (7:1 ratio by NMR), was obtained.

M.P. 86–90° C.

NMR (CDCl$_3$, δ): 2.20 (s, 3H), 2.30 (s, 3H), 3.73 (s, 3H), 3.83 & 3.91 (2s, total 3H), 4.80–4.92 (q, AB, 2H), 7.00–7.10 (m, 2H), 7.47 (s, 1H), 7.67–7.69 (m, 2H), 7.97–7.99 (d, 1H), 8.13 (s, 1H)

EXAMPLE 41

Preparation of 1-(phenylmethylsulfonyl)-5-methoxy-2-[[(3,5-dimethyl-4-methoxy-2-pyridyl) methyl]sulfinyl]-1H-benzimidazole and 1-(phenylmethylsulfonyl)-6-methoxy-2-[[(3,5-dimethyl-4-methoxy-2-pyridyl)methyl]sulfinyl]-1H-benzimidazole 172 mg of 5-methoxy-2-[[(3,5-dimethyl-4-methoxy-2-pyridyl)methyl]sulfinyl]-1H-benzimidazole was dissolved in 10 ml of dichloromethane and 0.2 ml of triethylamine. 95 mg of phenylmethylsulfonyl chloride was added. The reaction mixture was stirred at room temperature for 36 hr. Dichloromethane layer was washed with water and concentrated under reduced pressure. Residual material was lyophilized in vacuo to give 205 mg of the titled product, a mixture of 1-(phenylmethylsulfonyl)-5-methoxy-2-[[(3,5-dimethyl-4-methoxy-2-pyridyl)methyl]sulfinyl]-1H-benzimidazole and 1-(phenylmethylsulfonyl)-6-methoxy-2-[[(3,5-dimethyl-4-methoxy-2-pyridyl)methyl]sulfinyl]-1H-benzimidazole (2:1 ratio by NMR)

M.P. 130° C. (decomposition)

EXAMPLE 42

Preparation of 1-(n-propanesulfonyl)-5-methoxy-2-[[(3,5-dimethyl-4-methoxy-2-pyridyl)methyl] sulfinyl]-1H-benzimidazole and 1-(n-propanesulfonyl)-6-methoxy-2-[[(3,5-dimethyl-4-methoxy-2-pyridyl)methyl]sulfinyl]-1H-benzimidazole 103 mg of 5-methoxy-2-[[(3,5-dimethyl-4-methoxy-2-pyridyl)methyl]sulfinyl]-1H-benzimidazole was dissolved in 2 ml of chloroform and 0.1 ml of triethylamine. 1-Propanesulfonyl chloride (0.042 ml) was slowly added in ice bath. The reaction mixture was stirred at room temperature for 3 hr. Organic layer was washed with cold 0.1N sodium bicarbonate solution. Chloroform layer was dried over anhydrous magnesium sulfate, and concentrated under reduced pressure. Residual material was solidified from chloroform-ethyl ether-hexane to give 128 mg (95%) of the titled product (3:2 ratio).

M.P. 96–100° C.

EXAMPLE 43

Preparation of 1-(n-butanesulfonyl)-5-methoxy-2-[[(3,5-dimethyl-4-methoxy-2-pyridyl)methyl] sulfinyl]-1H-benzimidazole and 1-(n-butanesulfonyl)-6-methoxy-2-[[(3,5-dimethyl-4-methoxy-2-pyridyl)methyl]sulfinyl]-1H-benzimidazole 103 mg of 5-methoxy-2-[[(3,5-dimethyl-4-methoxy-2-pyridyl)methyl]sulfinyl]-1H-benzimidazole was dissolved in 2 ml of chloroform and 0.1 ml of triethylamine. 1-Butanesulfonyl chloride (0.042 ml) was slowly added in ice bath. The reaction mixture was stirred at room temperature for 3 hr. Organic layer was washed with cold 0.1N sodium bicarbonate solution. Chloroform layer was dried over anhydrous magnesium sulfate, and concentrated under reduced pressure. Residual material was solidified from chloroform-ethyl ether-hexane to give 130 mg (93%) of the titled product (3:2 ratio).

M.P. 54–56° C.

EXAMPLE 44

Preparation of 1-(isopropylsulfonyl)-5-methoxy-2-[[(3,5-dimethyl-4-methoxy-2-pyridyl)methyl]sulfinyl]-1H-benzimidazole and -(isopropylsulfonyl)-6-methoxy-2-[[(3.5-dimethyl-4-methoxy-2-pyridyl)methyl]sulfinyl]-1H-benzimidazole 103 mg of 5-methoxy-2-[[(3,5-dimethyl-4-methoxy-2-pyridyl)methyl]sulfinyl]-1H-benzimidazole was dissolved in 2 ml of chloroform and 0.1 ml of triethylamine. Isopropylsulfonyl chloride (0.042 ml) was slowly added in ice bath. The reaction mixture was stirred at room temperature for 24 hr. Organic layer was concentrated under reduced pressure and applied to silica gel column chromatography. 78 mg of the titled product was isolated (1:1 ratio).

M.P. 105–108° C. (decomposition)

EXAMPLE 45

1-[(N,N-dimethylamino)benzene-4-sulfonyl]-5-methoxy-2-[[(3,5-dimethyl-4-methoxy-2-pyridyl)methyl]sulfinyl]-1H-benzimidazole and 1-[(N,N-dimethylamino)benzene-4-sulfonyl]-6-methoxy-2-[[(3.5-dimethyl-4-methoxy-2-pyridyl)methyl]sulfinyl]-1H-benzimidazole 120 mg of p-(N,N-dimethylamino)benzenesulfonyl chloride was added to 172 mg of 5-methoxy-2-[[(3,5-dimethyl-4-methoxy-2-pyridyl)methyl]sulfinyl]-1H-benzimidazole dissolved in 20 ml of dichloromethane and 0.5 ml of triethylamine. The reaction mixture was stirred at room temperature for 16 hr. Dichloromethane layer was washed with water and 0.1N sodium carbonate solution. Organic layer was dried over anhydrous magnesium sulfate and was concentrated under reduced pressure. Residual material was lyophilized in vacuo to give 215 mg of the titled product (1:1 ratio).

M.P. 92–96° C.

NMR (CDCl$_3$, δ): 2.24 (s, 3H), 2.30 (s, 3H), 3.02 (s, 3H), 3.03 (s, 3H), 3.75 (s, 3H), 3.83 & 3.92 (2s, total 3H), 4.77–4.94 (2q, AB & A'B', total 2H), 6.57–6.61 (m, 2H), 6.96–7.07 (m, 1H), 7.48 & 7.68 (2d, total 1H), 7.85–7.90 (m, 3H), 8.22 (s, 1H)

EXAMPLE 46

Preparation of N-(4-1-{[2-({[4-(3-methoxypropoxy)-3-methyl-2-pyridyl]methyl}sulfinyl)benzimidazol-1-yl]sulfonyl}phenyl)urea 128 mg of N-[4-(chlorosulfonyl)phenyl]urea was added to 191 mg of 2-[(3-methyl-4-methoxypropoxy-2-pyridyl)methylsulfinyl]-1H-benzimidazole sodium salt in a mixture of 0.1 ml of triethylamine and 10 ml of dichloromethane-acetonitrile (50/50). The reaction mixture was stirred at room temperature overnight. Dichloromethane (20 ml) was added and washed with water, and 0.1M sodium bicarbonate solution. Organic layer was dried over anhydrous magnesium sulfate and evaporated. Residue was dissolved in minimum amounts of acetonitrile and ethyl ether was added for crystallization. Crystals were collected and dried. 190 mg of the titled product was obtained.

NMR (CDCl$_3$, δ): 2.03–2.07 (m, 2H), 2.18 (s, 3H), 3.34 (s, 3H), 3.52–3.54 (t, 2H), 4.05–4.08 (t, 2H), 4.76–5.00 (q, AB, 2H), 5.50–5.61 (br, —NH2), 6.69 (d, 1H), 7.33–7.37 (m, 3H), 7.51 (d, 1H), 7.65 (d, 1H), 7.81 (d, 2H), 7.98 (d, 1H), 8.17 (d, 1H), 8.97 (s, —NH—)

EXAMPLE 47

Preparation of 1-(pyridine-3-sulfonyl)-2-[[[3-methyl-4-(3-methoxypropoxy)-2-pyridyl]methyl]sulfinyl]-1H-benzimidazole 100 mg of pyridine-3-sulfonyl chloride was added to 191 mg of 2-[[[3-methyl-4-(3-methoxypropoxy)-2-pyridyl]methyl]sulfinyl]-1H-benzimidazole sodium salt in a mixture of 0.15 ml of triethylamine and 10 ml of dichloromethane. The reaction mixture was stirred at room temperature overnight. Dichloromethane (20 ml) was added and washed with water, and 0.1M sodium bicarbonate solution. Organic layer was dried over anhydrous magnesium sulfate and evaporated. Residue was dissolved in minimum amounts of acetonitrile and ethyl ether was added for precipitation. Solids was collected and dried to give 127 mg of the titled product.

NMR (CDCl$_3$, δ): 1.97–2.10 (m, 2H), 2.21 (s, 3H), 3.35 (s, 3H), 3.51–3.57 (t, 2H), 4.04–4.07 (t, 2H), 4.82–5.14 (q, AB, 2H), 6.73 (d, 1H), 7.41–7.56 (m, 3H), 7.80–8.02 (dd, 2H), 8.23–8.87 (m, 3H), 9.34 (s, 1H)

EXAMPLE 48

Preparation of 2-(4-{[2-({[4-(3-methoxypropoxy)-3-methyl-2-pyridyl]methyl}sulfinyl)benzimidazol-1-yl]sulfonyl}phenoxy)-N-(2-pyridyl)acetamide 170 mg of 2-[p-(chlorosulfonyl)phenoxy]-N-(2-pyridyl)acetamide was added to 191 mg of 2-[[[4-(3-methoxypropoxy)-3-methyl-2-pyridyl]methyl]sulfinyl]-1H-benzimidazole sodium salt in dichloromethane (15 ml) and triethylamine (0.1 ml). The reaction mixture was stirred at room temperature overnight. The reaction mixture was washed with water. Organic layer was dried over anhydrous magnesium sulfate, and evaporated. Residual material was lyophilized in vacuo to give 244 mg of the titled product.

M.P. 78–81° C. (decomposition)

NMR (CDCl$_3$, δ): 2.00–2.10 (m, 2H), 2.27 (s, 3H), 3.35 (s, 3H), 3.52–3.57 (t, 2H), 4.06–4.10 (t, 2H), 4.64 (s, 2H), 4.83–5.02 (q, AB, 2H), 6.67 (d, 1H), 7.07–7.10 (m, 3H), 7.32–7.49 (m, 3H), 7.70–7.82 (m, 2H), 7.99 (d, 1H), 8.14–8.30 (m, 4H), 8.77 (br, NH)

EXAMPLE 49

Preparation of 1-[4-(morpholin-4-yl)phenylsulfonyl]-2-[[4-(3-methoxypropoxy)-3-methyl-2-pyridyl]methyl]sulfinyl]-1H-benzimidazole 136 mg of 4-[(p-chlorosulfonyl)phenyl]morpholine was added to 191 mg of 2-[[[4-(3-methoxypropoxy)-3-methyl-2-pyridyl]methyl]sulfinyl]-1H-benzimidazole sodium salt in dichloromethane (15 ml) and triethylamine (0.1 ml). The reaction mixture was stirred at room temperature overnight. The reaction mixture was washed with water. Organic layer was dried over anhydrous magnesium sulfate, and evaporated. Residual material was lyophilized in vacuo to give 224 mg of the titled product.

M.P. 93–96° C. (decomposition)

NMR (CDCl$_3$, δ): 2.02–2.06 (m, 2H), 2.26 (s, 3H), 3.2–3.3 (m, 4H), 3.35 (s, 3H), 3.50–3.53 (t, 2H), 3.75–3.80 (m, 4H), 4.04–4.08 (t, 2H), 4.71–4.79 (q, AB, 2H), 6.71 (d, 1H), 7.26–7.5 (m, 4H), 7.8–8.1 (m, 2H), 8.27 (d, 1H)

EXAMPLE 50

Preparation of 1-[{2-(morpholin-4-yl)ethoxy}phenyl-4-sulfonyl]-2-[[[(4-(3-methoxypropoxy)-3-methyl-2-pridyl]methyl]sulfinyl]-1H-benzimidazole 136 mg of 4-[2-[(p-chlorosulfonyl)phenoxy]ethyl]morpholine was added to 191 mg of 2-[[[4-(3-methoxypropoxy)-3-methyl-2-pyridyl]methyl]sulfinyl]-1H-benzimidazole sodium salt in dichloromethane (15 ml) and triethylamine (0.1 ml). The reaction mixture was stirred at room temperature overnight. The reaction mixture was washed with water. Organic layer was dried over anhydrous magnesium sulfate, and evaporated. Residual material was lyophilized in vacuo to give 234 mg of the titled product.

NMR (CDCl$_3$, δ): 2.05–2.10 (m, 2H), 2.27 (s, 3H), 2.56 (m, 4H), 2.79–2.82 (t, 2H), 3.35 (s, 3H), 3.53–3.56 (t, 2H), 3.69–3.72 (m, 4H), 4.07–4.10 (t, 2H), 4.12–4.15 (t, 2H), 4.81–4.99 (q, AB, 2H), 6.68 (d, 1H), 6.95 (d, 2H), 7.36–7.46 (m, 2H), 7.81 (d, 1H), 7.99 (d, 1H), 8.06 (d, 2H), 8.21 (d, 1H)

EXAMPLE 51

Preparation of 1-(thiophene-2-sulfonyl)-2-[[[(4-(3-methoxypropoxy)-3-methyl-2-pyridyl]methyl]sulfinyl]-1H-benzimidazole 92 mg of thiophene-2-sulfonyl chloride was added to 191 mg of 2-[[[4-(3-methoxypropoxy)-3-methyl-2-pyridyl]methyl]sulfinyl]-1H-benzimidazole sodium salt in dichloromethane (15 ml) and triethylamine (0.1 ml). The reaction mixture was stirred at room temperature overnight. The reaction mixture was washed with water. Organic layer was dried over anhydrous magnesium sulfate, and evaporated. Residual material was lyophilized in vacuo to give 215 mg of the titled product.

M.P. 147–150° C.

NMR (CDCl$_3$, δ): 2.00–2.08 (m, 2H), 2.27 (s, 3H), 3.35 (s, 3H), 3.53–3.56 (s, 3H), 4.07–4.10 (t, 2H), 4.83–5.00 (q, AB, 2H), 6.67 (d, 1H), 7.08–7.10 (t, 1H), 7.42–7.49 (m, 2H), 7.68–7.70 (d, 1H), 7.82–7.84 (d, 1H), 8.00–8.03 (m, 2H), 8.18 (d, 1H)

EXAMPLE 52

Preparation of 1-benzenesulfonyl-2-[[[(4-(3-methoxypropoxy)-3-methyl-2-pyridyl]methyl]sulfinyl]-1H-benzimidazole 94 mg of benzenesulfonyl chloride was added to 191 mg of 2-[[[4-(3-methoxypropoxy)-3-methyl-2-pyridyl]methyl]sulfinyl]-1H-benzimidazole sodium salt in dichloromethane (15 ml) and triethylamine (0.1 ml). The reaction mixture was stirred at room temperature overnight. The reaction mixture was washed with water. Organic layer was dried over anhydrous magnesium sulfate, and evaporated. Residual material was crystallized from acetonitrile-ethyl ether. 210 mg of the titled product was obtained.

M.P. 126–128° C.

NMR (CDCl$_3$, δ): 1.97–2.09 (m, 2H), 2.27 (s, 3H), 3.34 (s, 3H), 3.52–3.57 (t, 3H), 4.05–4.10 (t, 3H), 4.81–5.03 (q, AB, 2H), 6.66 (d, 1H), 7.38–7.53 (m, 4H), 7.61–7.65 (t, 1H), 7.80 (d, 1H), 8.00 (d, 1H), 8.11–8.16 (m, 3H)

EXAMPLE 53

Preparation of 2-{4-[(5-methoxy-2-{[(3.5-dimethyl-4-methoxy-2-pyridyl)methyl]sulfinyl}benzimidazol-1-yl)sulfonyl]phenoxy}acetamide and 2-{4-[(6-methoxy-2-{[(3,5-dimethyl-4-methoxy-2-pyridyl)methyl]sulfinyl}benzimidazol-1-yl)sulfonyl]phenoxy}acetamide 5-Methoxy-2-[[(3,5-dimethyl-4-methoxy-2-pyridyl)methyl]sulfinyl]-1H-benzimidazole (344 mg) was dissolved in 40 ml of dichloromethane and 1 ml of triethylamine. 2-[p-(chlorosulfonyl)phenoxy]acetamide(250 mg) was added. The reaction mixture was stirred at room temperature overnight. The reaction was monitored by thin layer chromatography (developing solvent: chloroform-acetonitrile-methanol (100:10:7)). Solid was collected by filtration, washed with small amounts of dichloromethane, and dried in vacuo to give 415 mg of the titled product (3:2 ratio of 5-methoxy/6-methoxy compound).

M.P. 159–161° C. (decomposition)

NMR (DMSO-d6, δ): 2.13 (s, 3H), 2.25 (s, 3H), 3.69 (s, 3H), 3.78 & 3.88 (2s, total 3H), 4.56 (s, 2H), 4.82–5.04 (2q, AB, 2H), 7.05–7.18 (m, 3H), 7.34–7.40 (m, 1H), 7.60–7.90 (m, 2H), 8.12–8.18 (m, 2H)

EXAMPLE 54

Preparation of 2-(4-{[2-([3-methyl-4-(2,2,2-trifluoroethoxy)-2-pyridyl]methyl]sulfinyl)benzimidazol-1-yl]sulfonyl}phenoxy)acetamide 2-[[[3-Methyl-4-(2,2,2-trifluoroethoxy)-2-pyridyl]methyl]sulfinyl]-1H-benzimidazole (370 mg) was dissolved in 20 ml of dichloromethane and 1 ml of triethylamine. 2-[p-(chlorosulfonyl)phenoxy]acetamide(250 mg) was added. The reaction mixture was stirred at room temperature for 24 hr. Solid was collected, washed with dichloromethane, and dried in vacuo. 378 mg of the titled product was obtained.

M.P. 162–166° C. (decomposition)

NMR (DMSO-d6, δ): 2.21 (s, 3H), 4.55 (s, 2H), 4.86–5.15 (q, 2H and q, 2H) 6.99 (d, 1H), 7.16 (d, 2H), 7.39–7.58 (m, 2H), 7.79 (d, 1H), 7.97–8.03 (m, 2H), 8.17 (d, 2H)

EXAMPLE 55

Preparation of 2-{4-[(5-(difluoromethoxy)-2-{[(3,4-dimethoxy-2-pyridyl)methyl]sulfinyl} benzimidazol-1-yl)sulfonyl]phenoxy}acetamide and 2-{4-[(6-(difluoromethoxy)-2-{[(3,4-dimethoxy-2-pyridyl)methyl]sulfinyl}benzimidazol-1-yl)sulfonyl]phenoxy}acetamide 5-(difluoromethoxy)-2-[[(3,4-dimethoxy-2-pyridyl)methyl]sulfinyl]-1H-benzimidazole (383 mg) was dissolved in 20 ml of dichloromethane and 1 ml of triethylamine. 2-[p-(chlorosulfonyl)phenoxy]acetamide(250 mg) was added. The reaction mixture was stirred at room temperature for 24 hr. Solid was collected, washed with dichloromethane, and dried in vacuo. 413 mg of the titled product (1:1 ratio) was obtained.

M.P. 125–128° C. (decomposition)

EXAMPLE 56

Preparation of 2-(4-{[2-({[4-(3-methoxypropoxyy-3-methyl-2-pyridyl]methyl}sulfinyl)benzimidazol-1-yl]sulfonyl}phenoxy)acetamide 2-[[[4-(3-methoxypropoxy)-3-methyl-2-pyridyl]methyl]sulfinyl]-1H-benzimidazole sodium salt (382 mg) was added in dichloromethane (45 ml) and triethylamine (0.1 ml). 2-[p-(chlorosulfonyl)phenoxy]acetamide(250 mg) was added. The reaction mixture was stirred at room temperature overnight. The reaction mixture was washed with water. Organic layer was dried over anhydrous magnesium sulfate, and evaporated. Residual material was crystallized from acetonitrile-ethyl ether. 437 mg of the titled product was obtained.

M.P. 148–153° C. (decomposition)

NMR (DMSO-d6, δ): 1.93–1.97 (m, 2H), 2.18 (s, 3H), 3.35 (s, 3H), 3.46 (t, 2H), 4.06 (t, 2H), 4.56 (s, 2H), 4.83–5.13 (q, AB, 2H), 6.85 (d, 1H), 7.16 (d, 2H), 7.41–7.60 (m, 2H), 7.79 (d, 1H), 7.89 (d, 1H), 8.00–8.02 (d, 1H), 8.16–8.18 (d, 2H)

EXAMPLE 57

Preparation of 1-[{2-(morpholin-4-yl)ethoxy}phenyl-4-sulfonyl]-2-[(3-methyl-4-(2,2,2-trifluoroethoxy)-2-pyridyl)methylsulfinyl]-1H-benzimidazole 2-[[[3-Methyl-4-(2,2,2-trifluoroethoxy)-2-pyridyl]methyl]sulfinyl]-1H-benzimidazole (370 mg) was dissolved in 20 ml of dichloromethane and 1 ml of triethylamine. [2-(Morpholin-4-yl)ethoxy]phenyl-4-sulfonyl chloride (273 mg) was added and stirred at room temperature overnight. Dichloromethane layer was washed with an aqueous solution composed of 0.1M NaCl and ice-cooled 0.1N sodium bicarbonate solution. Dichloromethane layer was dried over anhydrous magnesium sulfate. Solvent was removed under reduced pressure. Residual material was lyophilized to provide 515 mg of the titled product.

NMR (CDCl$_3$, δ): 2.33 (s, 3H), 2.50–2.52 (m, 4H), 2.78–2.81 (t, 2H), 3.70–3.74 (m, 4H), 4.12–4.15 (t, 2H), 4.84–5.02 (q, AB, 2H), 6.63 (d, 1H), 6.96 (d, 2H), 7.38–7.49 (m, 2H), 7.81 (d, 1H), 7.99 (d, 1H), 8.04 (d, 2H), 8.26 (d, 1H)

EXAMPLE 58

Preparation of 1-[{2-(morpholin-4-yl)ethoxy}phenyl-4-sulfonyl]-5-methoxy-2-[[(3,5-dimethyl-4-methoxy-2-pyridyl)methyl]sulfinyl]-1H-benzimidazole and 1-[{2-(morpholin-4-yl)ethoxy}phenyl-4-sulfonyl]-6-methoxy-2-[[(3,5-dimethyl-4-methoxy-2-pyridyl)methyl]sulfinyl]-1H-benzimidazole 137 mg of [2-(Morpholin-4-yl)ethoxy]phenyl-4-sulfonyl chloride was added to 172 mg of 5-methoxy-2-[[(3,5-dimethyl-4-methoxy-2-pyridyl)methyl]sulfinyl]-1H-benzimidazole in dichloromethane (15 ml) and triethylamine (0.4 ml). The reaction mixture was stirred at room temperature overnight. The reaction mixture was washed with an aqueous solution composed of 0.1M NaCl and 0.1M sodium bicarbonate. Organic layer was dried over anhydrous magnesium sulfate, and evaporated. Residual material was lyophilized in vacuo to give 224 mg of the titled product (1:1 ratio).

NMR (CDCl$_3$, δ): 2.22 (s, 3H), 2.30 (s, 3H), 2.50–2.51 (m, 4H), 2.79 (t, 2H), 3.69–3.74 (m, 4H; s, 3H), 3.82 & 3.91 (2s, total 3H), 4.12 (t, 2H), 4.78–4.94 (q, AB, 2H), 6.93–7.08 (m, 3H), 7.46 (s, 1H), 7.68–7.86 (dd, 1H), 8.00–8.04 (m, 2 H), 8.17 (s, 1H)

EXAMPLE 59

Preparation of 1-[[2-{2-(morpholin-4-yl)ethoxy}ethoxy]phenyl-4-sulfonyl]-2-[(3-methyl-4-(2,2,2-trifluoroethoxy)-2-pyridyl)methylsulfinyl]-1H-benzimidazole 2-[[[3-Methyl-4-(2,2,2-trifluoroethoxy)-2-pyridyl]methyl]sulfinyl]-1H-benzimidazole (185 mg) was dissolved in 20 ml of dichloromethane and 0.5 ml of triethylamine. 2-[2-(Morpholin-4-yl)ethoxy]ethoxyphenyl-4-sulfonyl chloride (163 mg) was added and stirred at room temperature overnight. Dichloromethane layer was washed with an aqueous solution composed of 1M NaCl and 0.1N NaHCO$_3$. Dichloromethane layer was dried over anhydrous magnesium sulfate. Solvent was removed under reduced pressure. Residual material was separated by preparative TLC. 198 mg of the titled product was obtained.

NMR (CDCl$_3$, δ): 2.30 (s, 3H), 2.48 (m, 4H), 2.58 (t, 2H), 3.64–3.77 (m, 8H), 4.10 (t, 2H), 4.34–4.40 (q, 2H), 4.81–5.01 (q, AB, 2H), 6.62 (d, 1H), 6.94 (d, 2H), 7.35–7.47 (m, 2H), 7.78 (d, 1H), 7.96 (d, 1H), 8.02 (d, 2H), 8.22 (d, 1H)

EXAMPLE 60

Preparation of 1-[[2-{2-(morpholin-4-yl)ethoxy}ethoxy]phenyl-4-sulfonyl]-5-methoxy-2-[[(3.5-dimethyl-4-methoxy-2-pyridyl)methyl]sulfinyl]-1H-benzimidazole and 1-[[2-{2-(morpholin-4-yl)ethoxy}ethoxy]phenyl-4-sulfonyl]-6-methoxy-2-[[(3 5-dimethyl-4-methoxy-2-pyridyl)methyl]sulfinyl]-1H-benzimidazole 162 mg of [2-{2-(morpholin-4-yl)ethoxy}ethoxy]benzene-4-sulfonyl chloride was added to 172 mg of 5-Methoxy-2-[[(3,5-dimethyl-4-methoxy-2-pyridyl)methyl]sulfinyl]-1H-benzimidazole in dichloromethane (15 ml) and triethylamine (0.5 ml). The reaction mixture was stirred at room temperature overnight. The reaction mixture was washed with an aqueous solution composed of 1M NaCl and 0.1M sodium bicarbonate. Organic layer was dried over anhydrous magnesium sulfate, and evaporated. Residual material was dried in vacuo to give 254 mg of the titled product (1:1 ratio).

NMR (CDCl$_3$; δ): 2.21 (s, 3H), 2.29 (s, 3H), 2.49–2.53 (m, 2H), 2.69–2.78 (m, 4H), 3.67–3.89 (m, 8H; s, 3H; s, 3H), 4.07–4.13 (m, 2H), 4.76–4.93 (q, AB, 2H), 6.92–7.00 (m, 2H), 7.23 (d, 1H), 7.44 (d, 1H), 7.65–7.85 (dd, 1H), 7.98–8.03 (m, 2H), 8.15 (s, 1H)

EXAMPLE 61

Preparation of 1-[[2-{2-(morpholin-4-yl)ethoxy}ethoxy]phenyl-4-sulfonyl]-2-[[[(4-(3-methoxypropoxy)-3-methyl-2-pyridyl]methyl]sulfinyl]-1H-benzimidazole 2-[(3-Methyl-4-methoxypropoxy-2-pyridyl)methylsulfinyl]-1H-benzimidazole sodium salt (191 mg)

was dissolved in 20 ml of dichloromethane and 0.1 ml of triethylamine. 2-[2-(Morpholin-4-yl)ethoxy]ethoxyphenyl-4-sulfonyl chloride (163 mg) was added and stirred at room temperature overnight. Dichloromethane layer was washed with an aqueous solution composed of 1M NaCl and 0.1N NaHCO$_3$. Dichloromethane layer was dried over anhydrous magnesium sulfate. Solvent was removed under reduced pressure. Residual material was lyophilized to give 253 mg of the titled product.

NMR (CDCl$_3$, δ): 1.99–2.03 (m, 2H), 2.21 (s, 3H), 2.46 (t, 2H), 2.55 (t, 2H), 2.67 (t, 2H), 3.29 (s, 3H), 3.48–3.53 (m, 2H), 3.64–3.68 (m, 6H), 3.73–3.74 (m, 2H), 4.02–4.07 (m, 4H), 4.74–4,97 (q, AB, 2H), 6.62 (d, 1H), 6.89–6.92 (d, 2H), 7.31–7.42 (in, 2H), 7.75 (d, 1H), 7.93 (d, 1H), 8.02 (d, 2H), 8.13 (d, 1H)

EXAMPLE 62

Preparation of N-(carbamoylmethyl)-2-{4-[(5-methoxy-2-{[(3,5-dimethyl-4-methoxy-2-pyridyl)methyl]sulfinyl}benzimidazol-1-yl)sulfonyl]phenoxy}acetamide and N-(carbamoylmethyl)-2-{4-[(6-methoxy-2-{[(3.5-dimethyl-4-methoxy-2-pyridyl)methyl]sulfinyl}benzimidazol-1-yl)sulfonyl]phenoxy}acetamide Method 1) 5-Methoxy-2-[[(3,5-dimethyl-4-methoxy-2-pyridyl)methyl]sulfinyl]-1H-benzimidazole (172 mg) was dissolved in 20 ml of dichloromethane. Sodium tert-butoxide (55 mg) and N-(carbamoylmethyl)-2-[4-(chlorosulfonyl)phenoxy]acetamide (160 mg) was added. The reaction mixture was stirred at 30° C. for 36 hr. The reaction mixture was filtered. The filtrate was concentrated and treated with ethyl ether to give precipitates. Solid was collected, and dried in vacuo. 253 mg of the titled product (1:1 ratio) was obtained.

Method 2) 5-Methoxy-2-[[(3,5-dimethyl-4-methoxy-2-pyridyl)methyl]sulfinyl]-1H-benzimidazole (172 mg) was dissolved in 20 ml of dichloromethane and 0.4 ml of triethylamine. N-(carbamoylmethyl)-2-[4-(chlorosulfonyl)phenoxy]acetamide (160 mg) was added. The reaction mixture was stirred at 30° C. for 36 hr. The reaction mixture was treated with additional 80 ml of dichloromethane, and washed with 7% NaCl solution and 0.1N sodium bicarbonate solution. Dichloromethane layer was dried over anhydrous magnesium sulfate and evaporated under reduced pressure. The residual material was lyophilized to give 213 mg of the titled product (1:1 ratio).

NMR (DMSO-d6, δ): 2.14 (s, 3H), 2.25 (s, 3H), 3.66 (d, 2H), 3.70 (s, 3H), 3.88 (s, 3H), 4.67 (s, 2H), 4.81–5.08 (q, AB, 2H), 7.05–7.22 (m, 3H), 7.35 (s, 1H), 7.89 (dd, 1H), 8.14–8.18 (m, 2H), 8.32 (s, 1H)

EXAMPLE 63

Preparation of N-(carbamoylmethyl)-2-(4-{[2-({[3-methyl-4-(2,2,2-trifluoroethoxy)-2-pyridyl]methyl}sulfinyl)benzimidazol-1-yl]sulfonyl}phenoxy)acetamide 2-[[[3-Methyl-4-(2,2,2-trifluoroethoxy)-2-pyridyl]methyl]sulfinyl]-1H-benzimidazole (185 mg) was dissolved in 20 ml of dichloromethane and 0.5 ml of triethylamine, and N-(carbamoylmethyl)-2-[4-(chlorosulfonyl)phenoxy]acetamide (158 mg) was added. The reaction mixture was stirred at room temperature for 24 hr. Dichloromethane (100 ml) was added to the reaction mixture. The reaction mixture was washed with saturated NaCl solution, and 0.1N sodium bicarbonate solution. Dichloromethane layer was separated and dried over anhydrous magnesium sulfate. Dichloromethane was evaporated under reduced pressure to give syrupy material, which was lyophilized in vacuo. 237 mg of the titled product was obtained.

NMR (DMSO-d6, δ): 2.23 (s, 3H), 3.36 (br, -NH2, -NH), 3.66 (d, 2H), 4.67 (s, 2H), 4.84–5.17 (m, 2H and q, AB, 2H), 6.99–8.35 (m, 10H, aromatic H)

EXAMPLE 64

Preparation of N-(carbamoylmethyl)-2-(4-{[2-({[4-(3-methoxypropoxy)-3-methyl-2-pyridyl]methyl}sulfinyl)benzimidazol-1-yl]sulfonyl}phenoxy)acetamide 2-[[[4-(3-methoxypropoxy)-3-methyl-2-pyridyl]methyl]sulfinyl]-1H-benzimidazole sodium salt (190 mg) was dissolved in 20 ml of dichloromethane and 0.5 ml of triethylamine, and N-(carbamoylmethyl)-2-[4-(chlorosulfonyl)phenoxy]acetamide (160 mg) was added. The reaction mixture was stirred at room temperature for 24 hr. Dichloromethane (100 ml) was added to the reaction mixture. The reaction mixture was washed with saturated NaCl solution, and 0.1N sodium bicarbonate solution. Dichloromethane layer was separated and dried over anhydrous magnesium sulfate. Dichloromethane was evaporated under reduced pressure to give syrupy material, which was lyophilized in vacuo. 215 mg of the titled product was obtained.

NMR (DMSO-d6, δ): 1.94–1.97 (m, 2H), 2.19 (s, 3H), 3.22 (s, 3H), 3.46 (t, 2H), 3.67 (d, 2H), 4.06 (t, 2H), 4.68 (s, 2H), 4.84–5.14 (q, AB, 2H), 6.85 (d, 1H), 7.21 (d, 2H), 7.42–7.55 (m, 2H), 7.80 (d, 1H), 7.91 (d, 1H), 8.02(d, 1H), 8.18(d, 2H)

EXAMPLE 65

Preparation of 1-[(benzotriazol-1-yl)methyl]-5-methoxy-2-[[(3,5-dimethyl-4-methoxy-2-pyridyl)methyl]sulfinyl]-1H-benzimidazole and 1-[(benzotriazol-1-yl)methyl]-6-methoxy-2-[[(3.5-dimethyl-4-methoxy-2-pyridyl)methyl]sulfinyl]-1H-benzimidazole 5-Methoxy-2-[[(3,5-dimethyl-4-methoxy-2-pyridyl)methyl]sulfinyl]-1H-benzimidazole (172 mg) was dissolved in 20 ml of dichloromethane. Sodium tert-butoxide (55 mg) and 1-(chloromethyl)-1H-benzotriazole (85 mg) was added. The reaction mixture was stirred at 30° C. for 3 days. TLC analysis (developing solvent; chloroform-methanol 15:1) showed major one spot of 1-[(benzotriazol-1-yl)methyl]-5-methoxy-2-[[(3,5-dimethyl-4-methoxy-2-pyridyl)methyl]sulfinyl]-1H-benzimidazole above 5-methoxy-2-[[(3,5-dimethyl-4-methoxy-2-pyridyl)methyl]sulfinyl]-1H-benzimidazole. The titled product was purified by preparative thin layer chromatography. 195 mg of product, a mixture of 1-[(benzotriazol-1-yl)methyl]-5-methoxy-2-[[(3,5-dimethyl-4-methoxy-2-pyridyl)methyl]sulfinyl]-1H-benzimidazole and 1-[(benzotriazol-1-yl)methyl]-6-methoxy-2-[[(3,5-dimethyl-4-methoxy-2-pyridyl)methyl]sulfinyl]-1H-benzimidazole was obtained (3:2 ratio).

NMR (CDCl$_3$, δ): 2.21 (s, 3H), 2.24 (s, 3H), 3.70 (s, 3H), 3.79 & 3.86 (2s, total 3H), 4.85–5.08 (q, AB, 2H), 6.65 (d, 2H, N-CH$_2$-N), 6.89–8.12 (m, 8H)

EXAMPLE 66

Preparation of 1-[(benzotriazol-1-yl)methyl-2-[[[(4-(3-methoxypropoxy)-3-methyl-2-pyridyl]methyl]sulfinyl]-1H-benzimidazole 2-[[[4-(3-methoxypropoxy)-3-methyl-2-pyridyl]methyl]sulfinyl]-1H-benzimidazole sodium salt (190 mg) was dissolved in 20 ml of dichloromethane. 1-(Chloromethyl)-1H-benzotriazole (85 mg) was added. The reaction mixture was stirred at 30° C. for 3 days. TLC analysis showed one spot of product. The reaction mixture was filtered. The filtrate was concentrated under reduced pressure, and treated with ethyl ether-heptane for precipitation. Precipitated solids were collected and dried to give pure 1-[(benzotriazol-1-yl) methyl-2-[[[(4-(3-methoxypropoxy)-3-methyl-2-pyridyl] methyl]sulfinyl]-1H-benzimidazole (212 mg).

NMR (CDCl$_3$, δ): 2.05–2.08 (m, 2H), 2.21 (s, 3H), 3.34 (s, 3H), 3.54 (t, 2H), 4.08 (t, 2H), 4.86–5.16 (q, AB, 2H), 6.69–6.70 (d, 2H, N-CH$_2$-N), 7.00–8.15 (m, 10H)

EXAMPLE 67

Preparation of diethyl [5-methoxy-2-[(3.5-dimethyl-4-methoxy-2-pyridyl)methylsulfinyl]benzimidazol-1-yl]phosphate 5-Methoxy-2-[[(3,5-dimethyl-4-methoxy-2-pyridyl) methyl]sulfinyl]-1H-benzimidazole (172 mg) was dissolved in 50 ml of dichloromethane and 0.5 ml of triethylamine. Diethyl chlorophosphate (87 mg) was added. The reaction mixture was stirred at room temperature for 18 hr. The reaction mixture was washed with saturated NaCl solution, and 0.1N sodium bicarbonate solution twice times. Dichloromethane layer was separated and dried over anhydrous magnesium sulfate. Dichloromethane was evaporated under reduced pressure to give syrupy material, 215 mg of product. Syrupy product was slowly decomposed.

NMR (CDCl$_3$, δ): 1.28–1.38 (m, 6H), 2.10 (s, 3H), 2.19(s, 3H), 3.60 (s, 3H), 3.83 (s, 3H), 4.20–4.28 (m, 4H), 4.72–4.87 (q, AB, 2H), 6.91 (d, 1H), 7.7 (d, 1H), 7.92 (s, 1H), 8.18 (s, 1H)

EXAMPLE 68

Preparation of a mixture of 1-[(2-dimethylcarbamoyl-vinyl)benzene-4-sulfonyl]-5-methoxy-2-[(3,5-dimethyl-4-methoxy-2-pyridyl) methylsulfinyl]-1H-benzimidazole and 1-[(2-dimethylcarbamoyl-vinyl)benzene-4-sulfonyl]-6-methoxy-2-[(3,5-dimethyl-4-methoxy-2-pyridyl) methylsulfinyl]-1H-benzimidazole Substituted cinnamide-4-sulfonyl chloride derivatives such as N-morpholino cinnamide-4-sulfonyl chloride and 4-(2-dimethylcarbamoyl-vinyl)benzenesulfonyl chloride were prepared by a known method Cremlyn et al. Indian Journal of Chemistry, (1986) vol. 25B, 559–561).

5-Methoxy-2-[(3,5-dimethyl-4-methoxy-2-pyridyl) methylsulfinyl]-1H-benzimidazole (172 mg) was dissolved in 35 ml of dichloromethane and 0.5 ml of triethylamine. To this solution, 4-(2-dimethylcarbamoyl-vinyl) benzenesulfonyl chloride (140 mg) was added and stirred overnight at room temperature. The dichloromethane layer was washed with water and dried over anhydrous magnesium sulfate. After removing dichloromethane under reduced pressure, the residual material was lyophilized in vacuo to give 247 mg of the titled compounds (mixture of 5-methoxy/6-methoxy isomers in a ration of 1:1).

1H NMR (CDCl$_3$) δ: 2.28 (d, 6H), 3.03 (s, 3H), 3.13 (s, 3H), 3.80 (s, 3H), 3.81 and 3.91 (s, s; 5-methoxy and 6-methoxy), 4.86–5.07 (m, 2H), 6.90–8.21 (m, 10H)

EXAMPLE 69

Preparation of a mixture of 1-[(2-carbamoyl-vinyl) benzene-4-sulfonyl]-5-methoxy-2-[(3 5-dimethyl-4-methoxy-2-pyridyl)methylsulfinyl]-1H-benzimidazole and 1-[(2-carbamoyl-vinyl)benzene-4-sulfonyl]-6-methoxy-2-[(3,5-dimethyl-4-methoxy-2-pyridyl)methylsulfinyl]-1H-benzimidazole Cinnamide-4-sulfonyl chloride was prepared by a known method (Cremlyn et al. Indian Journal of Chemistry, (1984) vol. 23B, 94–96). The title compounds (5-methoxy/6-methoxy isomers in a ratio of 3:2) were prepared using a process similar to that of Example 68.

1H NMR (CDCl$_3$+CD$_3$CN) δ: 2.19 (s, 3H), 2.25 (s, 3H), 3.74 (s, 3H), 3.79 and 3.90 (s, s; 5-methoxy and 6-methoxy), 4.75–5.07 (q, 2H), 5.7–5.85 and 6.35–6.48 (br, —NH$_2$), 6.34 (d, 1H), 6.98–8.15 (m, 9H)

EXAMPLE 70

Preparation of a mixture of sodium 2-[5-methoxy-2-(4-methoxy-3,5-dimethyl pyridin-2-yl methanesulfinyl)benzimidazole-1-sulfonyl]benzene sulfonate and sodium 2-[6-methoxy-2-(4-methoxy-3,5-dimethyl pyridin-2-yl methanesulfinyl) benzimidazole-1-sulfonyl]benzene sulfonate Benzene-1,2-disulfonic anhydride was prepared by known method Hurtley et al. (1926) J. Chem. Soc., 1821–1828).

5-Methoxy-2-[(4-methoxy-3,5-dimethyl pyridin-2-yl) methylsulfinyl]benzimidazole (344 mg) was suspended in 20 ml of acetonitrile and sodium hydride (24 mg) was added. The suspension was stirred at room temperature for 2 hours to give sodium salt of 5-methoxy-2-[(4-methoxy-3,5-dimethyl pyridin-2-yl) methylsulfinyl]benzimidazole. To this suspension, benzene-1,2-disulfonic anhydride (221 mg) was added and stirred at room temperature for 3 hours. The precipitated product was collected by filtration and was washed with acetonitrile. 510 mg of title compounds (1:1 of 5-methoxy/6-methoxy isomers) were obtained.

1H NMR (D$_2$)) δ: 1.96 (s, 3H), 2.00 (s, 3H), 3.50 (d, 3H), 3.54 and 3.67 (s, s; 5-methoxy and 6-methoxy), 4.43–4.85 (m, 2H), 6.65–8.05 (m, 8H)

EXAMPLE 71

Preparation of a mixture of (4-[5-methoxy-2-(4-methoxy-3,5-dimethyl-2-pyridinyl)methylsulfinyl benzimidazole-1-sulfonyl]phenoxy}acetic acid methyl ester and {4-[6-methoxy-2-(4-methoxy-3,5-dimethyl-2-pyridinyl)methylsulfinyl benzimidazole-1-sulfonyl]phenoxy}acetic acid methyl ester 5-Methoxy-2-[(4-methoxy-3,5-dimethyl pyridin-2-yl) methylsulfinyl]benzimidazole (344 mg) was dissolved in 50 ml of dichloromethane and 0.5 ml of triethylamine, and (4-chlorosulfonyl phenoxy)acetic acid methyl ester (265 mg) was added and stirred at room temperature for 12 hours. Organic layer was washed with water, and evaporated under reduced pressure to give 390 mg of the title product (1:1 of 5-methoxy/6-methoxy isomer).

1H NMR (CDCl$_3$) δ: 2.24 (s, 3H), 2.27 (s, 3H), 3.77 (s, 6H), 3.81 and 3.90 (s, s; 5-methoxy and 6-methoxy), 4.63–4.65 (d, 2H), 4.86–5.05 (m, 2H), 6.92–8.18 (m, 8H)

EXAMPLE 72

Preparation of a mixture of 1-[(4-(2-dimethylaminoethoxy))benzenesulfonyl]-5-methoxy-2-[(3.5-dimethyl-4-methoxy-2-pyridyl) methylsulfinyl]-1H-benzimidazole and 1-[(4-(2-dimethylamino ethoxy))benzenesulfonyl]-6-methoxy-2-[(3.5-dimethyl-4-methoxy-2-pyridyl) methylsulfinyl]-1H-benzimidazole 5-Methoxy-2-[(3,5-dimethyl-4-methoxy-2-pyridyl) methylsulfinyl]-1H-benzimidazole (344 mg) was dissolved in 35 ml of dichloromethane and 0.5 ml of triethylamine. To this solution, 4-(dimethylaminomethyl)benzenesulfonyl chloride (233 mg) was added and stirred overnight at room temperature. Dichloromethane layer was washed with water and dried over anhydrous magnesium sulfate. After removing dichloromethane under reduced pressure, the residual material was lyophilized in vacuo to give 403 mg of the title compounds(1:1 of 5-methoxy/6-methoxy isomer).

1H NMR (CDCl$_3$) δ: 2.22 (s, 3H), 2.26 (s, 3H), 3.00 (s, 6H), 3.73 (s, 3H), 3.80 and 3.91 (s, s; 5-methoxy and 6-methoxy), 4.77–4.99 (q, 2H), 6.54–6.60 (m, 2H), 6.93–8.21 (m, 6H)

EXAMPLE 73

Preparation of a mixture of N-(2-{4-[5-methoxy-2-(4-methoxy-3,5-dimethyl pyridin-2-yl methylsulfinyl)benzimidazole-1-sulfonyl]-phenoxy}ethyl)-N,N,N-trimethyl ammonium trifluoromethanesulfonate and N-(2-{4-[6-methoxy-2-(4-methoxy-3,5-dimethyl pyridin-2-yl methylsulfinyl)benzimidazole-1-sulfonyl]-phenoxy}ethyl)-N,N,N-trimethyl ammonium trifluoromethanesulfonate.

5-Methoxy-2-[(3,5-dimethyl-4-methoxy-2-pyridyl) methylsulfinyl]-1H-benzimidazole sodium salt (108 mg) was dissolved in 35 ml of dichloromethane and N-(p-(chlorosulfonyl)phenoxyethyl)-N,N,N-trimethylammonium trifluoromethanesulfonate (128 mg) was added and stirred for 1 hour. The reaction mixture was filtered and washed with 10 ml of dichloromethane. Dichloromethane layer was dried over anhydrous magnesium sulfate. After removing dichloromethane under reduced pressure, the residual material was lyophilized in vacuo to give 200 mg of the title compounds (1:1 mixture of 5-methoxy/6-methoxy isomer).

1H NMR (CD$_3$CN) δ: 1.91 (s, 3H), 2.28 (s, 3H), 3.10 (s, 9H), 3.17 (m, 2H), 3.70 (s, 3H), 3.81 and 3.91 (s, s; 5-methoxy and 6-methoxy), 4.42 (m, 2H), 4.61–5.03 (q, 2H), 7.01–8.08 (m, 8H)

EXAMPLE 74

Preparation of a mixture of 2-{2-carbamoylmethoxy-4-[5-methoxy-2-((4-methoxy-3,5-dimethyl pyridin-2-yl)methylsulfinyl) benzimidazole-1-sulfonyl]phenoxy}acetamide and 2-{2-carbamoylmethoxy-4-[6-methoxy-2-((4-methoxy-3,5-dimethyl pyridin-2-yl)methylsulfinyl) benzimidazole-1-sulfonyl]phenoxy}acetamide 5-Methoxy-2-[(3,5-dimethyl-4-methoxy-2-pyridyl) methylsulfinyl]-1H-benzimidazole (344 mg) was dissolved in 35 ml of dichloromethane and 0.5 ml of triethylamine. To this solution, 3,4-bis(carbamoylmethoxy)benzenesulfonyl chloride (325 mg) was added and stirred overnight at room temperature. Solid was precipitated, which was collected and washed with 2 ml of dichloromethane. The solid was dried in vacuo to give 420 mg of the title compounds (1:1 of 5-methoxy/6-methoxy isomer). To the filtrate, dichloromethane (70 ml) was added, and washed with saturated sodium chloride solution, and dried over anhydrous magnesium sulfate. After concentrating the dichloromethane layer under reduced pressure, the residual material was treated with ethyl ether and hexane to give additional product, 58 mg (1:1 of 5-methoxy/6-methoxy isomer).

1H NMR (DMSO-d6) δ: 2.13 (s, 3H), 2.25 (s, 3H), 3.69–3.70 (d, 3H), 3.77 and 3.88 (s, s; 5-methoxy and 6-methoxy), 4.51 (d, 2H), 4.60 (d, 2H), 4.81–4.99 (m, 2H), 7.03 (d, 1H), 7.39–7.45 (br, two -NH$_2$), 7.10–7.89 (m, 6H)

EXAMPLE 75

Preparation of a mixture of 1,3-bis[5- or 6-methoxy-2-[((4-methoxy-3,5-dimethyl) pyridin-2-yl) methanesulfinyl]benzimidazole-1-sulfonyl]-benzene and 1-[5- or 6-methoxy-2-[((4-methoxy-3,5-dimethyl) pyridin-2-yl) methanesulfinyl] benzimidazole-1-sulfonyl]-3-[5- or 6-methoxy-2-[((4-methoxy-3 5-dimethyl) pyridin-2-yl) methanesulfinyl]benzimidazole-1-sulfonyl]-benzene.

5-Methoxy-2-[(3,5-dimethyl-4-methoxy-2-pyridyl) methylsulfinyl]-1H-benzimidazole (344 mg) was dissolved in 35 ml of dichloromethane and 1 ml of triethylamine. 1,3-Bis(chlorosulfonyl)benzene (138 mg) was added and stirred overnight. The reaction mixture was washed with water. Dichloromethane layer was dried over anhydrous magnesium sulfate. After removing dichloromethane under reduced pressure, the residual material was lyophilized in vacuo to give 380 mg of the title compounds (1:1 of 5-methoxy/6-methoxy isomer).

1H NMR (CDCl$_3$) δ: 2.13–2.15 (d, 6H), 2.26–2.29 (d, 6H), 3.71 (s, 6H), 3.78–3.80 (d, 5-OMe), 3.88–3.91 (d, 6-OMe), 4.69–5.05 (m, 4H), 6.95–8.60 (m, 12 H)

EXAMPLE 76

Preparation of sodium 2-[2-[[(4-methoxypropoxy-3-methyl) pyridin-2-yl]methanesulfinyl] benzimidazole-1-sulfonyl]benzenesulfonate The title compound was prepared in 92% yield by a method similar to that of Example 70, using [[(4-methoxypropoxy-3-methyl) pyridin-2-yl]methanesulfinyl] benzimidazole.

1H NMR (D$_2$O+CD$_3$CN) δ: 1.89 (s, 3H), 1.92–1.95 (m, 2H), 3.21 (s, 3H), 3.44–3.50 (t, 2H), 4.02–4.08 (t, 2H), 4.44–4.85 (m, 2H), 6.81 (d, 2H), 7.31–8.23 (m, 8H)

EXAMPLE 77

Preparation of 2-(2-carbamoylmethoxy-4-{2-[4-(3-methoxypropoxy)-3-methyl pyridin-2-yl methylsulfinyl]benzimidazole-1-sulfonyl}phenoxy) acetamide

[[(4-Methoxypropoxy-3-methyl) pyridin-2-yl] methanesulfinyl]benzimidazole (360 mg) was dissolved in 35 ml of dichloromethane and 1 ml of triethylamine. To this solution, 3,4-Bis(carbamoylmethoxy)benzenesulfonyl chloride (335 mg) was added and stirred overnight at room temperature. Solid was precipitated, which was collected and washed with 2 ml of dichloromethane. The solid was dried in vacuo to give 442 mg of the title compounds.

1H NMR (DMSO-d6) δ1.93–1.99 (m, 2H), 2.19 (s, 3H), 3.23 (s, 3H), 3.47 (t, 2H), 4.07 (t, 2H), 4.55 (s, 2H), 4.61 (s, 2H), 4.85–5.14 (q, 2H), 6.85–8.03 (m, 9H), 7.5 (br, -NH$_2$, 4H)

EXAMPLE 78

Preparation of 2-{2-carbamoylmethoxy-4-[6-difluoromethoxy-2-(3,4-dimethoxy-pyridin-2-ylmethanesulfinyl)-benzimidazole-1-sulfonyl]-phenoxy}-acetamide and 2-{2-carbamoylmethoxy-4-[5-difluoromethoxy-2-(3,4-dimethoxy-pyridin-2-ylmethanesulfinyl)-benzimidazole-1-sulfonyl]-phenoxy}-acetamide Using 5-difluoromethoxy-2-(3,4-dimethoxy-pyridin-2-ylmethanesulfinyl)-1H-benzimidazole, the title compounds were prepared (72% yield) by a method similar to that of Example 77.

1H NMR (DMSO-d6) δ3.78 (s, 3H), 3.85 (s, 3H), 4.52 (d, 2H), 4.59 (s, 2H), 4.89 (d, 2H), 4.9–5.3 (q, 2H), 7.01 (t, 1H), 7.09–7.95 (m, 8H), 7.45 (br, 4H, NH2)

EXAMPLE 79

Preparation of 2-(2-Carbamoylmethoxy-4-{2-[3-methyl-4-(2,2,2-trifluoro-ethoxy)-pyridin-2-ylmethanesulfinyl]-benzimidazole-1-sulfonyl}-phenoxy)-acetamide 2-[3-Methyl-4-(2,2,2-trifluoro-ethoxy)-pyridin-2-ylmethanesulfinyl]-1H-benzimidazole (369.3 mg) was suspended in acetonitrile (10 ml)-triethylamine (2 ml) and 3,4-bis(carbamoylmethoxy)benzenesulfonyl chloride (340 mg) was added. The reaction mixture was stirred at room temperature overnight. Solids were filtered and washed with acetonitrile (10 ml) followed with acetone (5 ml). The solids were again resuspended in methanol (3 ml), filtered and dried in vacuo to give 2-(2-carbamoylmethoxy-4-{2-[3-methyl-4-(2,2,2-trifluoro-ethoxy)-pyridin-2-ylmethanesulfinyl]-benzimidazole-1-sulfonyl}-phenoxy)acetamide (527 mg).

1H NMR (DMSO-d6) δ2.23 (s, 3H), 4.55 (s, 2H), 4.61 (s, 2H), 4.88 (q, 2H), 4.90–5.15 (q, AB, 2H), 6.99 (d, 1H), 7.12 (d, 1H), 7.42–7.56 (m, 2H), 7.46 (s, NH2), 7.50 (s, NH2), 7.74 (s, 1H), 7.78–7.88 (m, 2H), 7.99–8.02 (m, 2H)

CHEMICAL STABILITY

The chemical stability of the compounds of the invention has been followed kinetically at low concentration at 37° C. in a buffer solution composed of 0.2M NaCl, 50 mM sodium phosphate, pH 7.4, 2% bovine albumin serum, 5–10% methanol. The compounds of Example 1 and Example 19 were measured to have a half-life ($t_{1/2}$) 3 hr±0.5 hr and 3.5 hr±0.3 hr, respectively. The compound of Example 1 has slightly higher solubility in aqueous buffer than the compound of Example 19. The solubility of these compounds was found to affect their rate of hydrolysis.

Acid stability of the compounds was assayed in 95% methanol containing 0.1N HCl. Approximately 90% of the compound of Example 1 was still present intact (without decomposition) after 2.25 hour in this solution.

The hydrolysis of 2-(2-carbamoylmethoxy-4-{2-[4-(3-methoxy-propoxy)-3-methyl-pyridin-2-ylmethanesulfinyl]-benzimidazole-1-sulfonyl}-phenoxy)-acetamide was measured at various pH. When 2 mg of this compound was dissolved in 1 ml of 5% bovine serum albumin in 0.15M NaCl, 50 mM sodium phosphate at pH 7.4, at 37° C. a half life of 3.73 hr was measured. However, the half-life of the compound in the absence of bovine serum albumin at pH 7.4 was about 22.2 hr. This shows bovine serum albumin accelerates (catalyzes) the hydrolysis. At pH 2 the half-life of this compound was 1.8 hr, and at pH 8 it was 10.7 hr.

BIOLOGICAL ASSAY

Inhibition of ATPase activity was measured using isolated hog gastric vesicles. The gastric H,K-ATPase (10 μg) was incubated at 37° C. in a solution (1 ml) composed of 0.25M sucrose, 20 mM Pipes/Tris, pH 7.4, 0.15M KCl, 2 mM MgCl$_2$, valinomycin 2 μg/ml, and various concentration of compounds of the invention. At timed intervals, ATP was added (up to 2 mM) and incubated for 15 minutes and amount of released phosphate ion was measured. As a control experiment the prior art drug without a labile group on the benzimidazole nitrogen (e. g. OMEPRAZOLE or LANSOPRAZOLE) was used for measuring inhibition of enzyme activity. Initially (before it underwent hydrolysis), the samples having 10, 20, 50, and 100 μM of the compound of Example 1 failed to inhibit enzyme activity. After 80 minutes however, the sample having 10 μM of the compound of Example 1 inhibited 10% and the sample having 50 μM inhibited 50%. In samples having 10 μM of OMEPRAZOLE (control) and 10 μM of the compound of Example 1, the same level of inhibition was obtained after 5.75 hours of hydrolysis.

RELATIVE PLASMA CONCENTRATION OF OMEPRAZOLE IN MALE RAT

Male adult rats of the Sprague-Dawley strain were used for determining the concentration of OMEPRAZOLE in the plasma. All rats were derived of food but not of water for one day. Examples of compounds of the invention (2 mg/kg of rat weight) were orally administered to male rats (weighing 250 g to 270 g) and blood samples (0.3 ml) were taken at timed intervals. Blood samples were centrifuged and plasma was taken out. Plasma was extracted with 0.5 ml of dichloromethane. Dichloromethane layer was evaporated by nitrogen/air blowing. The residual materials were dissolved in 0.5 ml of 40% acetonitrile in 10 mM phosphate buffer (pH 7.4). Amounts of OMEPRAZOLE were determined by HPLC analysis. As a control, OMEPRAZOLE (4 mg/kg of rat weight) was orally administrated.

TABLE 3

Relative concentration of OMEPRAZOLE released in the plasma (arbitrary unit)

| min | EXAMPLE 29 | EXAMPLE 33 | EXAMPLE 37 | OMEPRAZOLE |
|-----|------------|------------|------------|------------|
| 20  | 4.5        | 2.5        | 1.67       | 28         |
| 40  | 14         | 34         | 14.36      | 4          |
| 60  | 8.5        | 13         | 3.5        | 2          |
| 80  | 3.5        | 4          | 1.88       | 1          |
| 100 | 2.5        | 2          | 1.88       | N/D*       |
| 120 | 1.875      | 2          | 1.5        | N/D*       |
| 140 | 0.625      | 1.5        | 1.5        |            |
| 160 | 0.6        | 1          | 1          |            |
| 180 | 0.6        | 1          | 1          |            |
| 210 | 1.5        | 1          | 0.7        |            |
| 240 | 0.5        | 1          | 0.7        |            |
| 270 | 0.5        | 0.5        | 0.7        |            |
| 300 | 0.2        | 0.5        | 0.4        |            |
| 330 | 0.1        | 0.3        | 0.2        |            |
| 360 | 0.05       | 0.3        | 0.1        |            |
| 390 | N/D        | 0.2        | 0.1        |            |
| 430 |            | 0.1        | N/D        |            |

*N/D: non-detectable.

INHIBITORY EFFECT ON GASTRIC ACID SECRETION OF THE CONSCIOUS MALE RAT AT TIMED INTERVALS

Male rats of the Sprague-Dawley strain were used in this experiment. OMEPRAZOLE (20 mg) was dissolved in 10 ml of 0.1N NaHCO$_3$, and 40 mg of the compound of Example 25, of Example 53, of Example 62, of Example 73 and of Example 74, respectively was dissolved in 10 ml of 40% solution of 2-hydroxypropyl-P-cyclodextrin in 50 mM sodium phosphate buffer of pH 7.4. From the solutions or suspensions as prepared above the following doses were orally administered to the rats: OMEPRAZOLE (10 μmole/kg), compound of Example 25 (10 μmole/kg), compound of Example 53 (10 μmole/kg), compound of Example 62 (10 μmole/kg), compound of Example 73 (10 μmole/kg) and compound of Example 74 compound (10 μmole/kg). 5 or 5.5 hours after oral administration the abdomen of the rat was incised and the pylorus was ligated under light ether anethesia. Histamine (30 mg/kg) and carbachol (30 ug/kg) were subcutaneously injected to stimulate acid production. The abdomen was surgically closed immediately. Three hour later the esophagus was ligated and the stomach was removed. The gastric juice was collected and acid output was quantified by titration using 0.1N NaOH solution. As a control experiment, 1 ml of 40% 2-hydroxypropyl-β-cyclodextrin in 50 mM phosphate buffer (pH 7.4) solution was orally administered without OMEPRAZOLE and without any compounds of the invention, that is without inhibitors of acid production. Acid output was quantified by same method as described above, showing maximum histamine and carbachol-stimulated gastric acid secretion. Percentage inhibition was calculated from the fractional responses elicited by the respective test compound and the control experiment.

TABLE 4

Inhibition of gastric acid secretion between 5–8 hours after oral administration

| compound | OMEPRAZOLE | Example 25 | Example 53 | Example 73 |
|---|---|---|---|---|
| % inhibition | 18.6 ± 8.9 | 61.3 ± 16.1 | 65.2 ± 11.3 | 21.8 ± 11.7 |

TABLE 5

Inhibition of gastric acid secretion between 5.5–8.5 hours after oral administration

| compound | OMEPRAZOLE | Example 62 | Example 74 |
|---|---|---|---|
| % inhibition | 19.6 ± 3.9 | 14.1 ± 7.5 | 49.7 ± 3.7 |

TABLE 6

Inhibition of gastric acid secretion between 4–7 hr after oral administration

| compound | LANOPRAZOLE | RABEPRAZOLE | Example 77 | Example 54 |
|---|---|---|---|---|
| % inhibition | 29% | 32% | 56% | 46.9% |

In a typical run of experiment showing the initial inhibition of gastric acid secretion, the compound of Example 74 (10 μmole/kg) was intraduodenally administered to rats after pylorus ligation. Histamine (30 mg/kg) was subcutaneously injected to stimulate acid production. The abdomen was surgically closed immediately. Four hours later the esophagus was ligated and the stomach was removed. Acid output was measured as described above. Compound of Example 74 inhibited acid production by 64.2% while OMEPRAZOLE provided 54.6% inhibition.

What is claimed is:
1. A compound of the formula

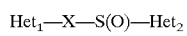

Wherein Het$_1$ is the group shown by the formula below:

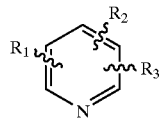

X is the group shown by the formula below:

and Het$_2$ is the group shown by the formula below:

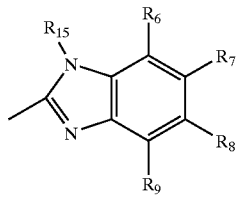

where R$_1$, R$_2$ and R$_3$ are independently selected from hydrogen, alkyl of 1 to 10 carbons, fluoro substituted alkyl of 1 to 10 carbons, alkoxy of 1 to 10 carbons, fluoro substituted alkoxy of 1 to 10 carbons, alkylthio of 1 to 10 carbons, fluoro substituted alkylthio of 1 to 10 carbons, alkoxyalkoxy of 2 to 10 carbons, amino, alkylamino and dialkylamino each of the alkyl groups in said alkylamino and dialkyl amino groups having 1 to 10 carbons, halogen, phenyl, alkyl substituted phenyl, alkoxy substituted phenyl, phenylalkoxy, each of the alkyl groups in said alkyl substituted phenyl, alkoxy substituted phenyl and phenylalkoxy having 1 to 10 carbons, piperidino, morpholino or two of the R$_1$, R$_2$ and R$_3$ groups jointly forming a 5 or 6 membered ring having 0 or 1 heteroatom selected from N, S and O;

R$_6$ through R$_9$ are independently selected from hydrogen, alkyl of 1 to 10 carbons, halogen substituted alkyl of 1 to 10 carbons, alkoxy of 1 to 10 carbons, halogen substituted alkoxy of 1 to 10 carbons, alkylcarbonyl, alkoxycarbonyl the alkyl group in said alkylcarbonyl and alkoxycarbonyl having 1 to 10 carbons, oxazolyl, imidazolyl, thiazolyl, pyrazolyl, or any two adjacent ones of the R$_6$ through R$_9$ groups may form a ring that may optionally include a heteroatom selected from N, O and S;

R$_{10}$ is hydrogen, alkyl of 1 to 10 carbons;
R$_{15}$ has the formula below

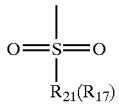

where R$_{17}$ is alkyl of 1 to 10 carbons, halogen substituted alkyl of 1 to 10 carbons, alkoxy having 1 to 10 carbons, halogen substituted alkoxy of 1 to 10 carbons, alkylthio having 1 to 10 carbons, halogen substituted alkylthio of 1 to 10 carbons, alkoxy carbonyl having 1 to 10 carbons, halogen substituted alkoxy carbonyl having 1 to 10 carbons, F, Cl, Br, I, NO$_2$, CN, OCOalkyl, NH$_2$, alkylamino and dialkylamino where in said OCOalkyl, alkylamino and dialkylamino groups each of said alkyl group has 1 to 10 carbons, further $R_{17}$ is carbamoyl, N- lower alkyl carbamoyl having 1 to 6 carbons, alkylcarbonyl having 1 to 10 carbons, (alkoxycarbonyl)alkoxy groups of each of said alkoxy group has 1 to 10 carbons, (alkoxycarbonyl)alkyl groups of each of said alkoxy or alkyl group has 1 to 10 carbons, (carbamoyl) alkoxy having 1 to 10 carbons, (N-alkylcarbamoyl)alkoxy where each of said alkoxy or alkyl groups has 1 to 6 carbons, (N,N-dialkylcarbamoyl)alkoxy where each of said alkoxy or alkyl groups has 1 to 6 carbons, (N-alkyl substituted or unsubstituted carbamoyl)poly(alkoxy)$_n$ where each of said alkoxy or alkyl groups has 1 to 6 carbons and where n represents an integer selected from 2 to 5, (N- alkyl substituted or unsubstituted carbamoyl)alkyl where each of said alkyl groups has 1 to 5 carbons, (carbamoyl)alkenyl having 2 to 5 carbons, (dialkylcarbamoyl)alkenyl where each of said alkyl groups has 1to 5 carbons and where the alkenyl group has 2 to 5 carbons, [N-(heteroaryl)carbamoyl]alkyl having 1 to 10 carbons wherein heteroaryl has 1 to 3 heteroatoms independently selected from N, O, and S, [N-(heteroaryl)carbamoyl]alkoxy having 1 to 10 carbons wherein heteroaryl has 1 to 3 heteroatoms independently selected from N, O, and S, poly(alkoxy)$_n$ where each of said alkoxy groups has 2 to 10 carbons and wherein n represents an integer selected from 2 to 5, 2-[(2-oxy-ethoxy)-ethoxy]-(ethoxy)$_n$-ethanoxy wherein n represents an integer selected from 1 to 3, guanidinyl group, (dialkylamino)alkyl where each of said alkyl groups has 1 to 5 carbons, (dialkylamino) alkoxy where each of said alkyl or alkoxy groups has 1 to 5 carbons, dialkylamino-poly(alkoxy), where each of said alkyl or alkoxy groups has 1 to 5 carbons and wherein n represents an integer selected from 2 to 5, [N-(carbamoylalkyl)carbamoyl]alkoxy where each of said alkoxy or alkyl groups has 1 to 5 carbons, (N-peptidyl carbamoyl)alkoxy where the alkoxy group has 1 to 5 carbons and wherein said peptidyl consists of two or three amino acids, N-peptidyl amido wherein said peptidyl consists of two or three amino acids, [N-(carbamoylalkyl)carbamoyl]alkyl where each of said alkyl groups has 1 to 5 carbons, [N-[(dicarbamoyl)alkyl]carbamoyl] alkoxy where each of said alkoxy or alkyl groups has 1 to 5 carbons, [N-[di(alkoxycarbonyl)alkyl]carbamoyl]alkoxy where each of said alkoxy or alkyl groups has 1 to 5 carbons, [N-[(dicarbamoyl)alkyl]amido where alkyl groups has 1 to 5 carbons, [N-[di(alkoxycarbonyl)alkyl]amido where each of said alkoxy or alkyl groups has 1 to 5 carbons, [N-[(carbamoyl)alkyl]amido where alkyl groups has 1 to 5 carbons, [N-[(alkoxycarbonyl)alkyl]amido where each of said alkoxy or alkyl groups has 1 to 5 carbons, [N-[[N-(heteroaryl) carbamoyl]alkyl]carbamoyl]alkoxy where each of said alkoxy or alkyl groups has 1 to 5 carbons and wherein said heteroaryl has 1 to 3 heteroatoms independently selected from N, O, and S, [(tri-alkyl)ammonium]-alkoxy where each of said alkoxy or alkyl groups has 1 to 5 carbons, aminosulfonyl, (sulfonato)alkyl having 2 to 5 carbons, (sulfonato)alkoxy having 2 to 5 carbons, N-[(sulfonato) alkyl]amido having 2 to 5 carbons, maleimido- and succinimido, and $R_{21}$ is (aryl)alkyl, (heteroaryl)alkyl where alkyl has 1 to 10 carbons, phenyl, naphthyl or heteroaryl having 1 to 3 heteroatoms independently selected from N, O and S, said phenyl, naphthyl or heteroaryl groups being unsubstituted or substituted with 1 to 5 $R_{17}$groups, or to a pharmaceutically acceptable salt of said compound, with the proviso that when $R_{21}$ is phenyl, then $R_{17}$ is not alkyl of 1 to 10 carbons, halogen substituted alkyl of 1 to 10 carbons, alkoxy having 1 to 10 carbons, halogen substituted alkoxy of 1 to 10 carbons, alkylthio having 1 to 10 carbons, halogen substituted alkylthio of 1 to 10 carbons, alkoxy carbonyl having 1 to 10 carbons, halogen substituted alkoxy carbonyl having 1 to 10 carbons, F, Cl, Br, I, $NO_2$, CN, OCOalkyl, $NH_2$, alkylamino and dialkylamino where in said OCOalkyl, alkylamino and dialkylamino groups each of said alkyl group has 1 to 10 carbons.

2. A compound in accordance with claim 1 where X represents a $CH_2$ group.

3. A compound in accordance with claim 1 where $R_{21}$ is phenyl, pyridyl, thiophenyl, thiazolyl, or imidazolyl.

4. A compound of the formula

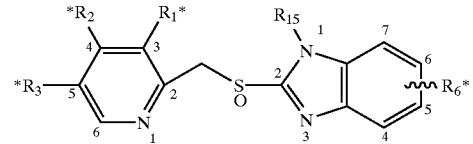

wherein $R_1^*$ is methyl, methoxy or chloro;

$R_2^*$ is methoxy, 2,2,2-trifluoroethoxy, 4-morpholino, ethylthio, (2,2,3,3,4,4,4-heptafluoroctyl)oxy; or $CH_3O(CH_2)_3O$;

$R_3^*$ is H or methyl;

$R_6^*$ is H, methoxy or difluoromethoxy group in the 5 or in the 6 position of the benzimidazole moiety; and $R_{15}$ has the formula below:

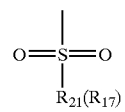

where $R_{17}$ is alkyl of 1 to 10 carbons, halogen substituted alkyl of 1 to 10 carbons, alkoxy having 1 to 10 carbons, halogen substituted alkoxy of 1 to 10 carbons, alkylthio having 1 to 10 carbons, halogen substituted alkylthio of 1 to 10 carbons, alkoxy carbonyl having 1 to 10 carbons, halogen substituted alkoxy carbonyl having 1 to 10 carbons, F, Cl, Br, I, $NO_2$, CN, OCOalkyl, $NH_2$, alkylamino and dialkylamino where in said OCOalkyl, alkylamino and dialkylamino groups each of said alkyl group has 1 to 10 carbons, further $R_{17}$ is carbamoyl, N- lower alkyl carbamoyl having 1 to 6 carbons, alkylcarbonyl having 1 to 10 carbons, (alkoxycarbonyl)alkoxy groups of each of said alkoxy group has 1 to 10 carbons, (alkoxycarbonyl)alkyl groups of each of said alkoxy or alkyl group has 1 to 10 carbons, (carbamoyl) alkoxy having 1 to I0 carbons, (N-alkylcarbamoyl) alkoxy where each of said alkoxy or alkyl groups has 1 to 6 carbons, (N,N-dialkylcarbamoyl)alkoxy where each of said alkoxy or alkyl groups has 1 to 6 carbons, (N-alkyl substituted or unsubstituted carbamoyl)poly (alkoxy)$_n$ where each of said alkoxy or alkyl groups has 1 to 6 carbons and where n represents an integer selected from 2 to 5, (N- alkyl substituted or unsubstituted carbamoyl)alkyl where each of said alkyl groups has 1 to 5 carbons, (carbamoyl)alkenyl having 2 to 5 carbons, (dialkylcarbamoyl)alkenyl where each of said alkyl groups has 1 to 5 carbons and where the alkenyl group has 2 to 5 carbons, [N-(heteroaryl)carbamoyl] alkyl having 1 to 10 carbons wherein heteroaryl has 1 to 3 heteroatoms independently selected from N, O, and S, [N-(heteroaryl)carbamoyl]alkoxy having 1 to 10 carbons wherein heteroaryl has 1 to 3 heteroatoms independently selected from N, O, and S, poly(alkoxy)$_n$ where each of said alkoxy groups has 2 to 10 carbons and wherein n represents an integer selected from 2 to 5, 2-[(2-oxy-ethoxy)-ethoxy]-(ethoxy)$_n$-ethanoxy wherein n represents an integer selected from 1 to 3, guanidinyl group, (dialkylamino)alkyl where each of said alkyl groups has 1 to 5 carbons, (dialkylamino) alkoxy where each of said alkyl or alkoxy groups has 1 to 5 carbons, dialkylamino-poly(alkoxy), where each of said alkyl or alkoxy groups has 1 to 5 carbons and wherein n represents an integer selected from 2 to 5, [N-(carbamoylalkyl)carbamoyl]alkoxy where each of said alkoxy or alkyl groups has 1 to 5 carbons, (N-peptidyl carbamoyl)alkoxy where the alkoxy group has 1 to 5 carbons and wherein said peptidyl consists of two or three amino acids, N-peptidyl amido wherein said peptidyl consists of two or three amino acids, [N-(carbamoylalkyl)carbamoyl]alkyl where each of said alkyl groups has 1 to 5 carbons, [N-[(dicarbamoyl) alkyl]carbamoyl] alkoxy where each of said alkoxy or alkyl groups has 1 to 5 carbons, [N-[di(alkoxycarbonyl) alkyl]carbamoyl]alkoxy where each of said alkoxy or alkyl groups has 1 to 5 carbons, [N-[(dicarbamoyl) alkyl]amido where alkyl groups has 1 to 5 carbons, [N-[di(alkoxycarbonyl)alkyl]amido where each of said alkoxy or alkyl groups has 1 to 5 carbons, [N-[(carbamoyl)alkyl]amido where alkyl groups has 1 to 5 carbons, [N-[(alkoxycarbonyl)alkyl]amido where each of said alkoxy or alkyl groups has 1 to 5 carbons, [N-[[N-(heteroaryl) carbamoyl]alkyl]carbamoyl] alkoxy where each of said alkoxy or alkyl groups has 1 to 5 carbons and wherein said heteroaryl has 1 to 3 heteroatoms independently selected from N, O, and S, [(tri-alkyl)ammonium]-alkoxy where each of said alkoxy or alkyl groups has 1 to 5 carbons, aminosulfonyl, (sulfonato)alkyl having 2 to 5 carbons, (sulfonato)alkoxy having 2 to 5 carbons, N-[(sulfonato) alkyl]amido having 2 to 5 carbons, maleimido- and succinimido, and R$_{21}$ is (aryl)alkyl, (heteroaryl)alkyl where alkyl has 1 to 10 carbons, phenyl, naphthyl or heteroaryl having 1 to 3 heteroatoms independently selected from N, O and S, said phenyl, naphthyl or heteroaryl groups being unsubstituted or substituted with 1 to 5 R$_{17}$ groups, or to a pharmaceutically acceptable salt of said compound, with the proviso that when R$_{21}$ is phenyl, then R$_{17}$ is not alkyl of 1 to 10 carbons, halogen substituted alkyl of 1 to 10 carbons, alkoxy having 1 to 10 carbons, halogen substituted alkoxy of 1 to 10 carbons, alkylthio having 1 to 10 carbons, halogen substituted alkylthio of 1 to 10 carbons, alkoxy carbonyl having 1 to 10 carbons, halogen substituted alkoxy carbonyl having 1 to 10 carbons, F, Cl, Br, I, NO$_2$, CN, OCOalkyl, NH$_2$, alkylamino and dialkylamino where in said OCOalkyl, alkylamino and dialkylamino groups each of said alkyl group has 1 to 10 carbons.

5. A compound in accordance with claim 4 where R$_{21}$ (R$_{17}$) is phenyl, thienyl or pyridyl, substituted or unsubstituted with the R$_{17}$ groups.

6. A compound in accordance with claim 5 where R$_{17}$ is selected from Cl, Br, F, alkyl, alkoxy, trifluoromethyl, trifluoromethoxy, di-(alkyl)amino, alkoxycarbonyl, (alkoxycarbonyl)alkoxy, guanidinyl, carbamoyl, N-alkyl carbamoyl, carbamoylalkyl, (N-alkyl carbamoyl)alkyl, (carbamoyl)alkenyl, (dialkylcarbamoyl) alkenyl, di-(alkylamino)alkoxy, morpholinyl, (morpholin-4-yl)alkoxy, (morpholin-4-yl)poly(alkoxy)$_n$ where n is an integer having the value of 2 to 5, di-(alkylamino)alkyl, poly(alkoxy)$_n$ alkoxy where n is an integer having the value of 1 to 5, 2-[(2-oxy-ethoxy)-ethoxy]-(ethoxy)$_n$-ethanoxy wherein n represents an integer selected from 1 to 3, (carbamoyl) alkoxy, [(N-(alkyl)carbamoyl]alkoxy, [N,N-(dialkyl) carbamoyl)alkoxy, (N,N-dialkylcarbamoyl)alkyl, [N-(heteroaryl)carbamoyl]alkyl, [N-(heteroaryl) carbamoyl] alkoxy, [N-(aryl)carbamoyl]alkoxy, [N-[(dicarbamoyl) alkyl]carbamoyl]alkoxy, [N-[(carbamoyl)alkyl]carbamoyl] alkoxy, [N-[(N-alkyl carbamoyl)alkyl]carbamoyl]alkoxy, [N-[di(alkoxycarbonyl)alkyl]carbamoyl]alkoxy, [N-[(dicarbamoyl)alkyl]amido, [N-[di(alkoxycarbonyl)alkyl] amido, [N-[(carbamoyl)alkyl]amido, [N-[(alkoxycarbonyl) alkyl]amido, aminosulfonyl, (sulfonato)alkyl, (sulfonato) alkoxy, N-[(sulfonato)alkyl]amido, maleimido-, succinimido and [(tri-alkyl)ammonium]-alkoxy groups, wherein the terms alkyl and alkoxy define groups having 1 to 6 carbons, and alkenyl defines groups having 2 to 5 carbons, and heteroaryl has 1 to 3 heteroatoms independently selected from N, O, and S, with the proviso that when R$_{21}$ is phenyl, then R$_{17}$ is not alkyl, halogen substituted alkyl, alkoxy, halogen substituted alkoxy, alkoxy carbonyl, F, Cl, Br or dialkylamino.

7. A compound in accordance with claim 5 where R$_{17}$ is selected from Cl, Br, F, methyl, methoxy, trifluoromethyl, trifluoromethoxy, dimethylamino, ethoxycarbonyl, (methoxycarbonyl) methoxy, carbamoyl, guanidinyl, 2-carbamoyl vinyl, 2-(N,N-dimethylcarbamoyl)vinyl, (carbamoyl)methoxy, [N-(pyridyl)carbamoyl]methoxy, morpholinyl, (morpholin-4-yl)alkoxy, [(morpholin-4-yl) alkoxy]alkoxy, 2-(dimethylamino)ethoxy, [N-[(carbamoyl) methyl]carbamoyl]methoxy, (N-(1,3-dicarbamoyl-propyl) carbamoyl)methoxy, (dimethylamino)methyl, aminosulfonyl, sodium(sufonato)alkoxy having 2 to 4 carbons, (trimethylammonium) alkoxy having 2 to 4 carbons, poly(alkoxy) n wherein the alkoxy groups have 1 to 3 carbons and n is an integer having the values of 2 to 5, and —(OCH$_2$CH$_2$)$_{n'}$—O— where n' is 4 or 5, with the proviso that when R$_{21}$ is phenyl, then R$_{17}$ is not alkyl, halogen substituted alkyl, alkoxy, halogen substituted alkoxy, alkoxy carbonyl, F, Cl, Br or dialkylamino.

8. A compound in accordance with claim 5 where R$_{21}$ is a phenyl or pyridyl group substituted in the 4 (para) or in the 3 (meta) position or in both the 3 and 4 positions with the R$_{17}$ group that is independently selected from Cl, Br, F, CH$_3$, CH$_3$O, CF$_3$, CF$_3$O—, (CH$_3$)$_2$N, NH$_2$CO, NH$_2$C(=NH)NH, 4-morpholino, 2-(4-morpholinyl) ethoxy, 2-[2-(4-morpholinyl)ethoxy]ethoxy, 3-(4-morpholinyl)propoxy, poly(alkoxy)$_n$-alkoxy where n is an integer having the value of 1 to 3, $^-$O$_3$S—CH$_2$CH$_2$CH$_2$—O, X$^-$ (CH$_3$)$_3$N$^+$ CH$_2$CH$_2$O—, NH$_2$COCH$_2$O, (pyridyl)NHCOCH$_2$O, NH$_2$COCH$_2$NHCOCH$_2$O, (CH$_3$)$_2$NCH$_2$, MeOCOCH$_2$CH (COOMe)NHCO or EtOCO group, where X is an anion, with the proviso that when R$_{21}$ is phenyl, then R$_{17}$ is not Cl, Br, F, CH$_3$, CH$_3$O, CF$_3$, CF$_3$O, or (CH$_3$)$_2$N.

9. A compound in accordance with claim 4, selected from the group consisting of:

1-[[2-{2-(morpholin-4-yl)ethoxy}ethoxy]phenyl-4-sulfonyl]-5-(difluoromethoxy)-2-[[(3,4-dimethoxy-2-pyridyl)methyl]sulfinyl]-1H-benzimidazole, 1-[[2-{2-(morpholin-4-yl)ethoxy}ethoxy]phenyl-4-sulfonyl]-6-(difluoromethoxy)-2-[[(3,4-dimethoxy-2-pyridyl)methyl]sulfinyl]-1H-benzimidazole, 1-[[2-{2-(morpholin-4-yl)ethoxy}ethoxy]phenyl-4-sulfonyl]-2-[[[3-methyl-4-(2,2,2-trifluoroethoxy)-2-pyridyl]methyl]sulfinyl]-1H-benzimidazole, 1-(4acetaminobenzenesulfonyl)-5-methoxy-2-[[(3,5-dimethyl-4-methoxy-2-pyridyl)methyl]sulfinyl]-1H-benzimidazole, 1-(4-acetaminobenzenesulfonyl)-6-methoxy-2-[[(3,5-dimethyl-4methoxy-2-pyridyl)methyl]sulfinyl]-1H-benzimidazole, 1-[(2-dimethylcarbamoyl-vinyl)benzene-4-sulfonyl]-5-methoxy-2-[(3,5-dimethyl-4-methoxy-2-pyridyl)methylsulfinyl]-1H-benzimidazole, -[(2-dimethylcarbamoyl-vinyl)benzene4-sulfonyl]-6-methoxy-2-[(3,5-dimethyl-4-methoxy-2-pyridyl)methylsulfinyl]-1H-benzimidazole, 1-[(2-carbamoyl-vinyl)benzene-4-sulfonyl]-5-methoxy-2-[(3,5-dimethyl-4-methoxy-2-pyridyl)methylsulfinyl]-1H-benzimidazole, 1-[(2-carbamoyl-vinyl)benzene-4-sulfonyl]-6-methoxy-2-[(3,5-dimethyl-4-methoxy-2-pyridyl)methylsulfinyl]-1H-benzimidazole, {4-[5-methoxy-2-(4-methoxy-3,5-dimethyl-2-pyridinyl)methanesulfinyl benzimidazole-1-sulfonyl]phenoxy}acetic acid methyl ester, {4-[6-methoxy-2-(4-methoxy-3,5-dimethyl-2-pyridinyl)methanesulfinyl benzimidazole-1-sulfonyl]phenoxy}acetic acid methyl ester, 1-[(4-(2-dimethylaminoethoxy))benzenesulfonyl]-5-methoxy-2-[(3,5-dimethyl-4-methoxy-2-pyridyl)methylsulfinyl]-1H-benzimidazole, 1-[(4-(2-dimethylamino ethoxy))benzenesulfonyl]-6-methoxy-2-[(3,5-dimethyl-4-methoxy-2-pyridyl)methylsulfinyl]-1H-benzimidazole, N-(2-{4-[5-methoxy-2-(4-methoxy-3,5-dimethyl pyridin-2-yl methanesulfinyl)benzimidazole-1-sulfonyl]-phenoxy}ethyl)N,N,N-trimethyl ammonium trifluoromethanesulfonate, N-(2-{4-[6-methoxy-2-(4-methoxy-3,5-dimethyl pyridin-2-yl methanesulfinyl)benzimidazole-1-sulfonyl]-phenoxy}ethyl)N,N,N-trimethyl ammonium trifluoromethanesulfonate, 2-{2-carbamoylmethoxy-4-[5-methoxy-2-((4-methoxy-3,5-dimethyl pyridin-2-yl)methanesulfinyl)benzimidazole-1-sulfonyl]phenoxy}acetamide, 2-{2-carbamoylmethoxy4-[6-methoxy-2-((4-methoxy-3,5-dimethyl pyridin-2-yl)methanesulfinyl)benzimidazole-1-sulfonyl]phenoxy}acetamide, 1,3-bis[5-methoxy-2-[((4-methoxy-3,5-dimethyl) pyridin-2-yl) methanesulfinyl]benzimidazole-1-sulfonyl]-benzene, 1,3-bis[6-methoxy-2-[((4-methoxy-3,5-dimethyl) pyridin-2-yl) methanesulfinyl]benzimidazole-1-sulfonyl]-benzene, 1-[5- methoxy-2-[((4-methoxy-3,5-dimethyl) pyridin-2-yl) methanesulfinyl]benzimidazole-1-sulfonyl]-3-[6-methoxy-2-[((4-methoxy-3,5-dimethyl) pyridin-2-yl) methanesulfinyl]benzimidazole-1-sulfonyl]-benzene, 1-[6-methoxy-2-[((4-methoxy-3,5-dimethyl) pyridin-2-yl) methanesulfinyl]benzimidazole-1-sulfonyl]-3-[5-methoxy-2-[((4-methoxy-3,5-dimethyl) pyridin-2-yl) methanesulfinyl]benzimidazole-1-sulfonyl]-benzene, 2-(2-carbamoylmethoxy-4-{2-[4-(3-methoxypropoxy)-3-methyl pyridin-2-yl methylsulfinyl]benzimidazole-1-sulfonyl}phenoxy)acetamide, 2-{2-carbamoylmethoxy-4-[6-difluoromethoxy-2-(3,4-dimethoxy-pyridin-2-ylmethanesulfinyl)-benzimidazole-1-sulfonyl]-phenoxy}-acetamide, 2-{2-carbamoylmethoxy-4-[5-difluoromethoxy-2-(3,4-dimethoxy-pyridin-2-ylmethanesulfinyl)-benzimidazole-1-sulfonyl]-phenoxy}-acetamide, 2-(2-carbamoylmethoxy-4-{2-[3-methyl-4-(2,2,2-trifluoro-ethoxy)-pyridin-2-ylmethanesulfinyl]-benzimidazole-1-sulfonyl}-phenoxy)-acetamide,

[2-{2-[3-methyl-4-(2,2,2-trifluoro-ethoxy)-pyridin-2-ylmethanesulfinyl]-benzoimidazole-1-sulfonyl}-benzenesulfonic acid sodium salt, 1-(pyridine-3-sulfonyl)-5-methoxy-2-[[(3,5-dimethyl-4-methoxy-2-pyridyl)methyl]sulfinyl]-1H-benzimidazole, 1-(pyridine-3-sulfonyl)-6-methoxy-2-[[(3,5-dimethyl-4-methoxy-2-pyridyl)methyl]sulfinyl]-1H-benzimidazole, 1-pyridine-3-sulfonyl)-2-[[[3-methyl-4-(2,2,2-trifluoroethoxy)-2-pyridyl]methyl]sulfinyl]-1H-benzimidazole, 1-(pyridine-3-sulfonyl)-5-(difluoromethoxy)-2-[[(3,4-dimethoxy-2-pyridyl)methyl]sulfinyl]-1H-benzimidazole, 1-(pyridine-3-sulfonyl)-6-(difluoromethoxy)-2-[[(3,4-dimethoxy-2-pyridyl)methyl]sulfinyl]-1H-benzimidazole, 1-[4-[(morpholin-4-yl)phenyl]sulfonyl]-5-methoxy-2-[[(3,5-dimethyl-4-methoxy-2-pyridyl)methyl]sulfinyl]-1H-benzimidazole, 1-[4-[(morpholin-4-yl)phenyl]sulfonyl]-6-methoxy-2-[[(3,5-dimethyl--methoxy-2-pyridyl)methyl]sulfinyl]-1H-benzimidazole, 2-[4-(3-Methoxy-propoxy)-3-methyl-pyridin-2-ylmethanesulfinyl]-1-(6,7,9,10,12,13,15,16-octahydro-5,8,11,14,17-pentaoxa-benzocyclopentadecene-2-sulfonyl)-1H-benzimidazole, 2-[3-Methyl-4-(2,2,2-trifluoro-ethoxy)-pyridin-2-ylmethanesulfinyl]-1-(6,7,9,10,12,13,15,16-octahydro-5,8,11,14,17-pentaoxa-benzocyclopentadecene-2-sulfonyl)-1H-benzimidazole, 5-Methoxy-2-(4-methoxy-3,5-dimethyl-pyridin-2-ylmethanesulfinyl)-1-(6,7,9,10,12,13,15,16-octahydro-5,8,11,14,17-pentaoxa-benzocyclopentadecene-2-sulfonyl)-1H-benzimidazole, 6-Methoxy-2-(4-methoxy-3,5-dimethyl-pyridin-2-ylmethanesulfinyl)-1-(6,7,9,10,12,13,15,16-octahydro-5,8,11,14,17-pentaoxa-benzocyclopentadecene-2-sulfonyl)-1H-benzimidazole, 5-Difluoromethoxy-2-(3,4-dimethoxy-pyridin-2-ylmethanesulfinyl)-1-(6,7,9,10,12,13,15,16-octahydro-5,8,11,14,17-pentaoxa-benzocyclopentadecene-2-sulfonyl)-1H-benzimidazole, 6-Difluoromethoxy-2-(3,4-dimethoxy-pyridin-2-ylmethanesulfinyl)-1-(6,7,9,10,12,13,15,16-octahydro-5,8,11,14,17-pentaoxa-benzocyclopentadecene-2-sulfonyl)-1H-benzimidazole, 2-{4-[(5-methoxy-2-{[(3,5-dimethyl-4-methoxy-2-pyridyl)methyl]sulfinyl}benzimidazol-1-yl)sulfonyl]phenoxy}acetamide, 2-{4-[(5-methoxy-2-{[(3,5-dimethyl-4-methoxy-2-pyridyl)methyl]sulfinyl}benzimidazol-1-yl)sulfonyl]phenoxy}-N-(2-pyridyl)acetamide, N-(carbamoylmethyl)-2-{4-[(5-methoxy-2-{[(3,5-dimethyl-1- methoxy-2-pyridyl)methyl]sulfinyl}benzimidazol-1-yl)sulfonyl]phenoxy}acetamide, 2-{4-[(6-methoxy-2-{[(3,5-dimethyl-4-methoxy-2-pyridyl)methyl]sulfinyl}benzimidazol-1-yl)sulfonyl]phenoxy}acetamide, 2-{4-[(6-methoxy-2-{[(3,5-dimethyl-4-methoxy-2-pyridyl)methyl]sulfinyl}benzimidazol-1-yl)sulfonyl]phenoxy}-N-(2-pyridyl)acetamide, N-(carbamoylmethyl)-2-{4-[(6-methoxy-2-{[(3,5-dimethyl-4-methoxy-2-pyridyl)methyl]sulfinyl}benzimidazol-1-yl)sulfonyl]phenoxy}acetamide, 2-(4-{[2-({[3-methyl(2,2,2-trifluoroethoxy)-2-pyridyl]methyl}sulfinyl)benzimidazol-1-yl]sulfonyl}phenoxy)acetamide, 2-(4-{[2-({[3-methyl-4(2,2,2-trifluoroethoxy)-2-pyridyl]methyl}sulfinyl)benzimidazol-1-yl]sulfonyl}phenoxy)-N-(2-pyridyl)acetamide, N-(carbamoylmethyl)-2-(4-{[2-({[3-methyl-4-(2,2,2-trifluoroethoxy)-2-pyridyl]methyl}sulfinyl)benzimidazol-1-yl]sulfonyl}phenoxy)acetamide, 2-{4-[(5-(difluoromethoxy)-2-{[(3,4-dimethoxy-2-pyridyl)methyl]sulfinyl}benzimidazol-1-yl)sulfonyl]phenoxy}acetamide, 2-{4-[(5-(difluoromethoxy)-2-{[(3,4-dimethoxy-2-pyridyl)methyl]sulfinyl}benzimidazol-1-yl)sulfonyl]phenoxy}-N-(2-pyridyl)acetamide, N-(carbamoylmethyl)-2-{4-[(5-(difluoromethoxy)-2-{[(3,4-dimethoxy-2-pyridyl)methyl]sulfinyl}benzimidazol-1-yl)sulfonyl]phenoxy}acetamide, 2-{4-[(6-(difluoromethoxy)-2-{[(3,4-dimethoxy-2-pyridyl)methyl]sulfinyl}benzimidazol-1-yl)sulfonyl]phenoxy}acetamide, 2-{4-[(6-(difluoromethoxy)-2-{[(3,4-dimethoxy-2-pyridyl)methyl]sulfinyl}benzimidazol-1-yl)sulfonyl]phenoxy}-N-(2-pyridyl)acetamide, N-(carbamoylmethyl)-2-{4-[(6-(difluoromethoxy)-2-{[(3,4-dimethoxy-2-pyridyl)methyl]sulfinyl}benzimidazol-1-yl)sulfonyl]phenoxy}acetamide, 2-(4-{[2-({[4-(3-methoxypropoxy)-3-methyl-2-pyridyl]methyl}sulfinyl)benzimidazol-1-yl]sulfonyl}phenoxy)acetamide, 2-(4-{[2-({[4-(3-methoxypropoxy)-3-methyl-2-pyridyl]methyl}sulfinyl)benzimidazol-1-yl]sulfonyl}phenoxy)-N-(2-pyridyl)acetamide, N-(carbamoylmethyl)-2-(4-{[2-({[4-(3-methoxypropoxy)-3-methyl-2-pyridyl]methyl}sulfinyl)benzimidazol-1-yl]sulfonyl}phenoxy)acetamide, 1-[[4-(3-(morpholin-4-yl) propoxy}phenyl]sulfonyl]-5-(difluoromethoxy)-2-[[(3,4-dimethoxy-2-pyridyl)methyl]sulfinyl]-1H-benzimidazole, 1-[[4-{3-(morpholin-4-yl) propoxy}phenyl]sulfonyl]-6-(difluoromethoxy)-2-[[(3,4-dimethoxy-2-pyridyl)methyl]sulfinyl]-1H-benzimidazole, 1-[[4-{3-(morpholin-4-yl) propoxy}phenyl]sulfonyl]-5-methoxy-2-[[(3,5-dimethyl-4-methoxy-2-pyridyl)methyl]sulfinyl]-1H-benzimidazole, 1-[[4-{3-(morpholin-4-yl)propoxy}phenyl]sulfonyl]-6-methoxy-2-[[(3,5-dimethyl-4-methoxy-2-pyridyl)methyl]sulfinyl]-1H-benzimidazole, 1-[[4-{3-(morpholin-4-yl) propoxy}phenyl]sulfonyl]-2-[(3-methyl-4-methoxypropoxy-2-pyridyl)methylsulfinyl]-1H-benzimidazole, 1-[[4-{3-(morpholin-4-yl)propoxy}phenyl]sulfonyl]-2-[(3-methyl-4-(2,2,2-trifluoroethoxy)-2-pyridyl)methylsulfinyl]-1H-benzimidazole, 1-[4-[2-(morpholin-4-yl)ethoxy]phenylsulfonyl]-2-[[[(4-(3-methoxypropoxy)-3-methyl-2-pyridyl]methyl]sulfinyl]-1H-benzimidazole, 1-[4-[2-(morpholin-4yl)ethoxy]phenylsulfonyl]-5-(difluoromethoxy)-2-[[(3,4-dimethoxy-2-pyridyl)methyl]sulfinyl]-1H-benzimidazole, 1-[4-[2-(morpholin-4-yl)ethoxy]phenylsulfonyl]-5-methoxy-2-[[(3,5-dimethyl-4-methoxy-2-pyridyl)methylsulfinyl]]-1H-benzimidazole, 1-[4-[2-(morpholin-4-yl)ethoxy]phenylsulfonyl]-6-(difluoromethoxy)-2-[[(3,4dimethoxy-2-pyridyl)methyl]sulfinyl]-1H-benzimidazole, 1-[4-[2-(morpholin-4-yl)ethoxy]phenylsulfonyl]-6-methoxy-2-[[(3,5-dimethyl-4-methoxy-2-pyridyl)methylsulfinyl]]-1H-benzimidazole, 1-[4-[2-(morpholin-4-yl)ethoxy]phenylsulfonyl]-2-[[[3-methyl-4-(2,2,2-trifluoroethoxy)-2-pyridyl]methyl]sulfinyl]-1H-benzimidazole, 1-[{(N,N-dimethylamino)methyl}benzene-4-sulfonyl]-5-methoxy-2-[[(3,5-dimethyl-4-methoxy-2-pyridyl)methyl]sulfinyl]-1H-benzimidazole, 1-[2-acetamido-4-methyl-5-thiazolylsulfonyl]-5-methoxy-2-[[(3,5-dimethyl-4-methoxy-2-pyridyl)methyl]sulfinyl]-1H-benzimidazole, 1-(thiophene-2-sulfonyl)-5-methoxy-2-[[(3,5-dimethyl-4-methoxy-2-pyridyl)methyl]sulfinyl]-1H-benzimidazole, 1-[{(N,N-dimethylamino)methyl}benzene-4-sulfonyl]-6-methoxy-2-[[(3,5-dimethyl-4-methoxy-2-pyridyl)methyl]sulfinyl]-1H-benzimidazole, 1-[2-acetamido-4-methyl-5-thiazolylsulfonyl]-6-methoxy-2-[[(3,5-dimethyl-4-methoxy-2-pyridyl)methyl]sulfinyl]-1H-benzimidazole, 1-(thiophene-2-sulfonyl)-6-methoxy-2-[[(3,5-dimethyl4-methoxy-2-pyridyl)methyl]sulfinyl]-1H-benzimidazole, 1-(thiophene-2-sulfonyl)-2-[[[(4-(3-methoxypropoxy)-3-methyl-2-pyridyl]methyl]sulfinyl]-1H-benzimidazole, 1-(thiophene-2-sulfonyl)-5-(difluoromethoxy)-2-[[(3,4-dimethoxy-2-pyridyl)methyl]sulfinyl]-1H-benzimidazole, 1-(thiophene-2-sulfonyl)-6-(difluoromethoxy)-2-[[(3,4-dimethoxy-2-pyridyl)methyl]sulfinyl]-1H-benzimidazole, 1-(thiophene-2-sulfonyl)-]-2-[[[3-methyl-4-(2,2,2-trifluoroethoxy)-2-pyridyl]methyl]sulfinyl]-1H-benzimidazole, 1-(phenylmethylsulfonyl)-5-methoxy-2-[[(3,5-dimethyl-4-methoxy-2-pyridyl)methyl]sulfinyl]-1H-benzimidazole, 1-[(N,N-dimethylamino)benzene-4-sulfonyl]-5-methoxy-2-[[(3,5-dimethyl-4-methoxy-2-pyridyl)methyl]sulfinyl]-1H-benzimidazole, 1-(phenylmethylsulfonyl)-6-methoxy-2-[[(3,5-dimethyl-4-methoxy-2-pyridyl)methyl]sulfinyl]-1H-benzimidazole, 1-[(N,N-dimethylamino)benzene-4-sulfonyl]-6-methoxy-2-[[(3,5-dimethyl-4-methoxy-2-pyridyl)methyl]sulfinyl]-1H-benzimidazole, 1-(pyridine-3-sulfony)-2-[[(3-methyl-4-methoxypropoxy-2-pyridyl)methyl]sulfinyl]-1H-benzimidazole, 1-[4-(morpholin-4-yl)phenylsulfonyl]-2-[[[(4-(3-methoxypropoxy)-3-methyl-2-pyridyl]methyl]sulfinyl]-1H-benzimidazole, 1-[4-[2-(morpholin-4-yl)ethoxy]phenylsulfonyl]-2-[(3-methoxyphenyl)methylsulfinyl]imidazolo{5,4c}pyridine, 1-[4-[2-(morpholin-4-yl)ethoxy]phenylsulfonyl]-2-[{2-(dimethylamino)phenyl}methylsulfinyl]-1H-benzimidazole, 1-[[2-{2-(morpholin-4-yl)ethoxy}ethoxy]phenyl-4-sulfonyl]-5-methoxy-2-[[(3,5-dimethyl-4-methoxy-2-pyridyl)methyl]sulfinyl]-1H-benzimidazole, 1-[[2-{2-(morpholin-4-yl)ethoxy}ethoxy]phenyl-4-sulfonyl]-6-methoxy-2-[[(3,5-dimethyl-4-methoxy-2-pyridyl)methyl]sulfinyl]-1H-benzimidazole, 1-[[2-{2-(morpholin-4-yl)ethoxy}ethoxy]phenyl-4sulfonyl]-2-[[[(4-(3-methoxypropoxy)-3-methyl-2-pyridyl]methyl]sulfinyl]-1H-benzimidazole.

10. A compound of the formula

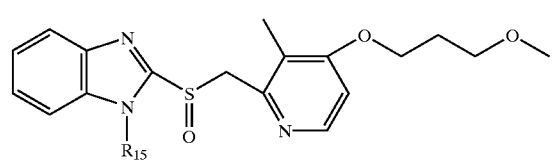

where $R_{15}$ is selected from the groups (1) through (11) shown below:

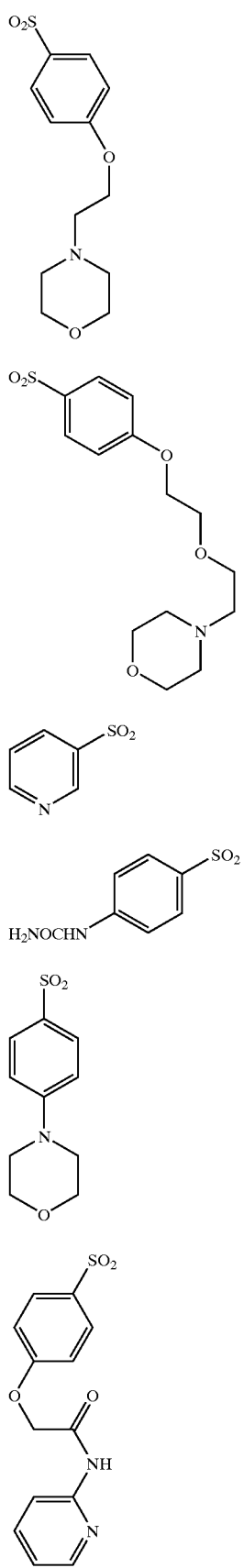
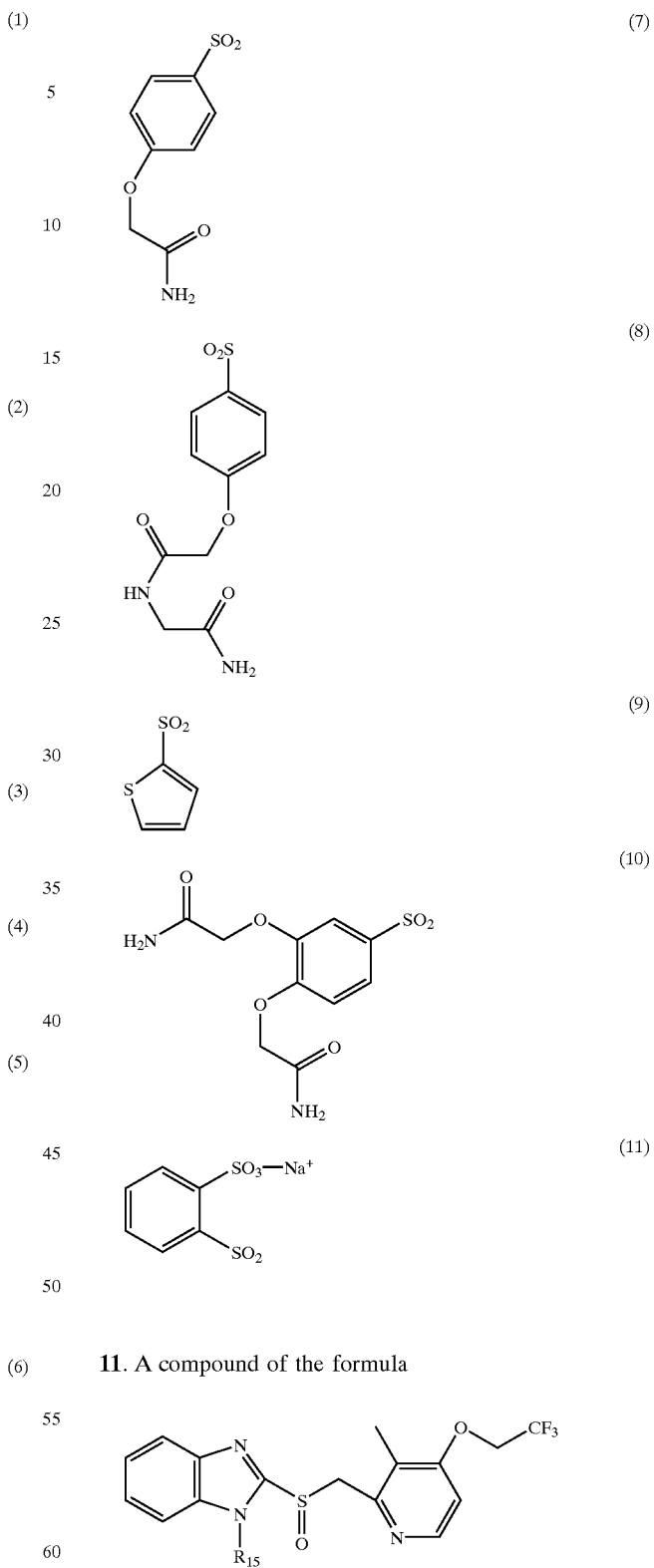
11. A compound of the formula
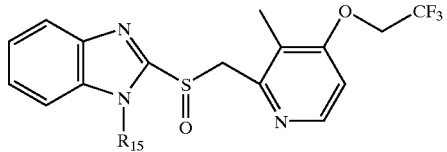
where $R_{15}$ is selected from the groups (1) through (9) shown below:

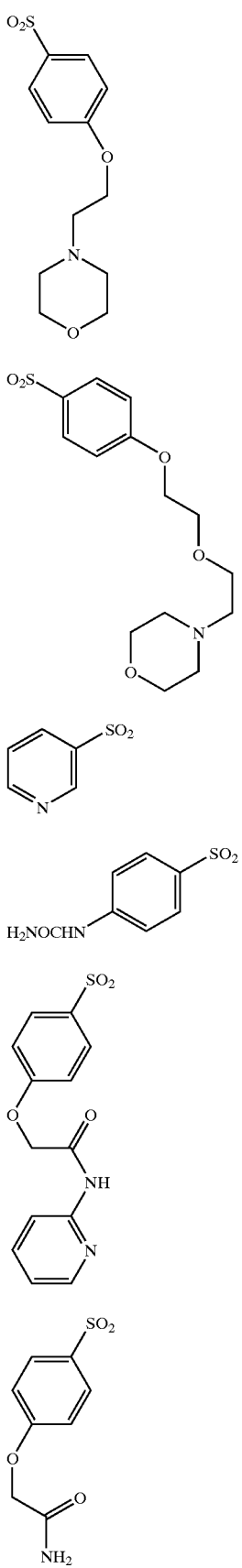
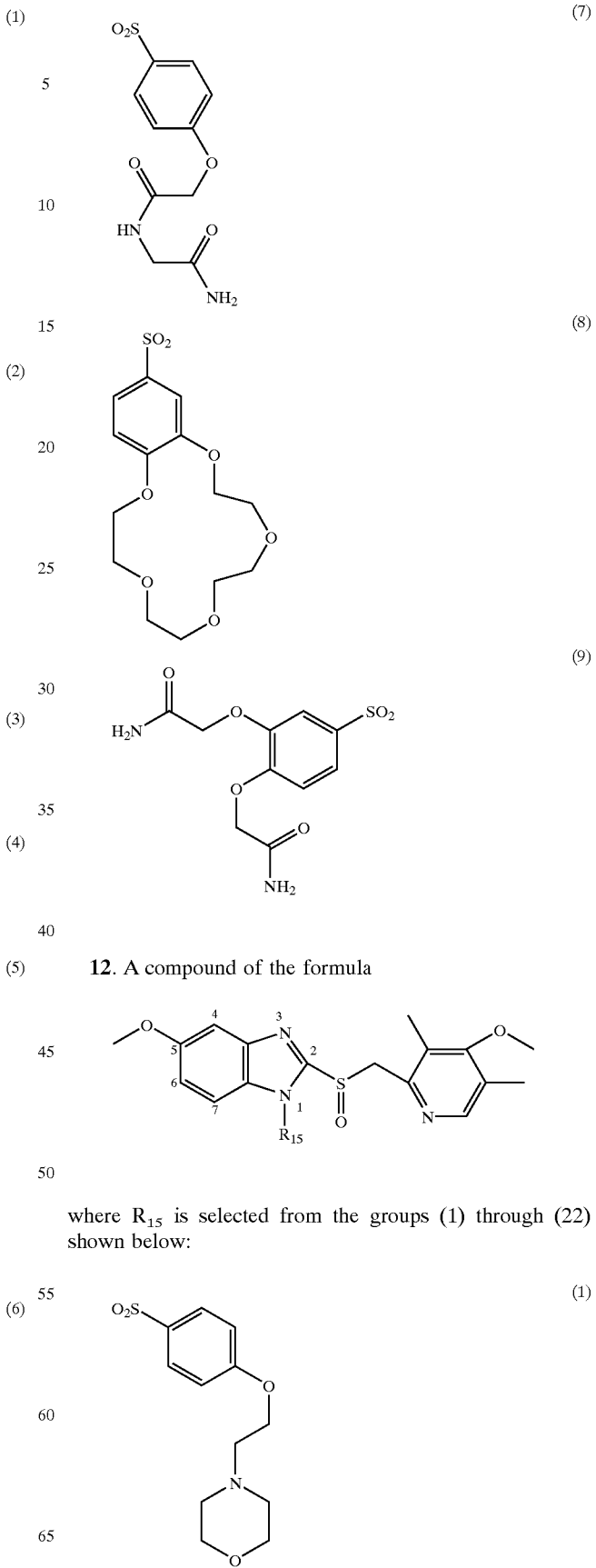
12. A compound of the formula
where $R_{15}$ is selected from the groups (1) through (22) shown below:

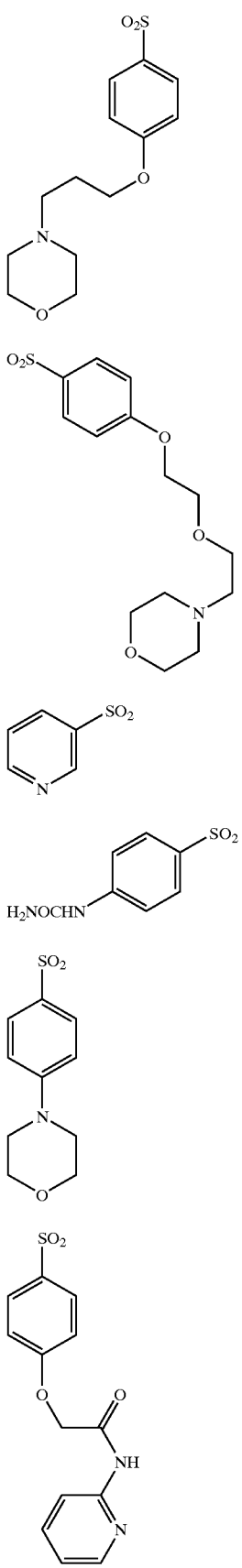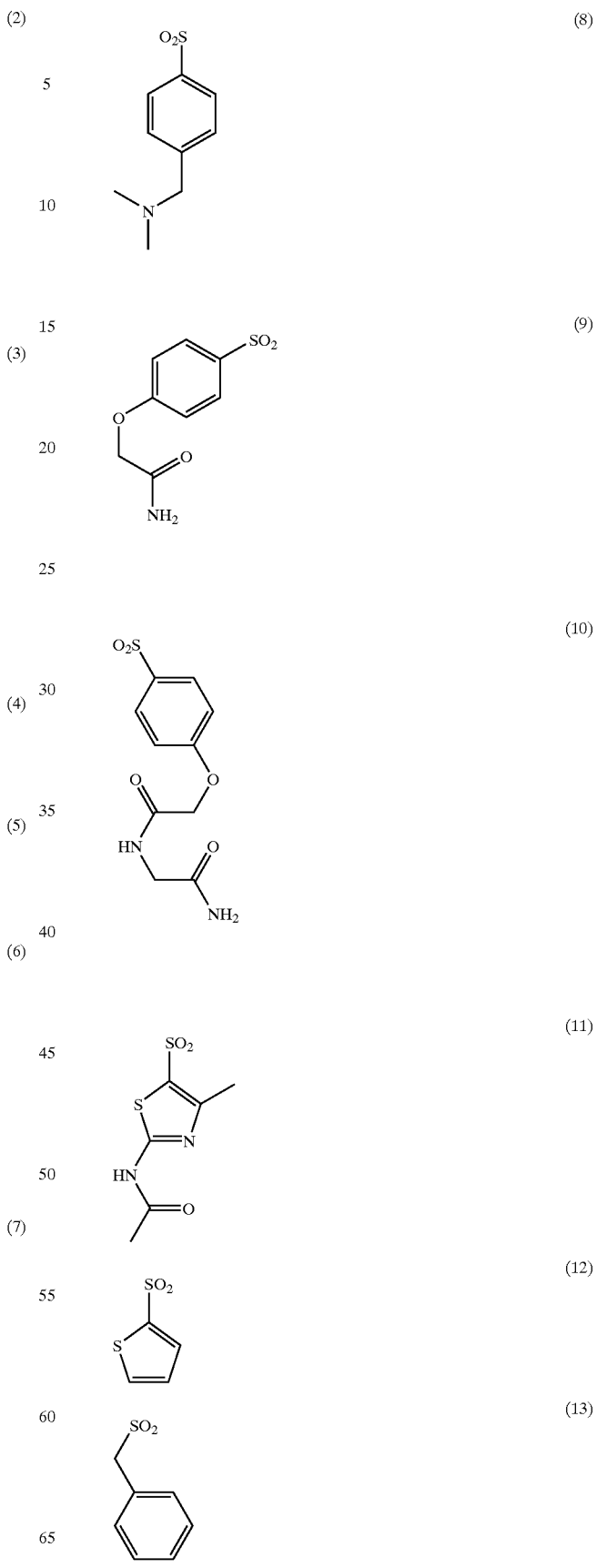

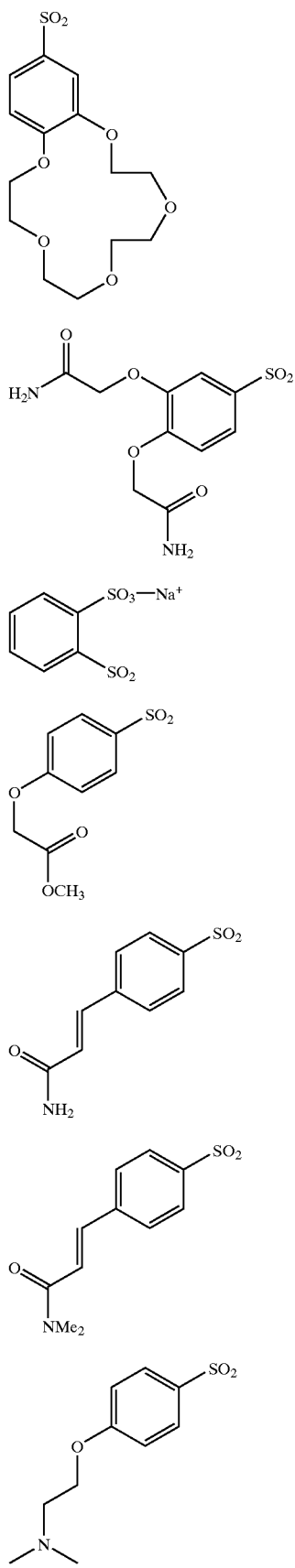
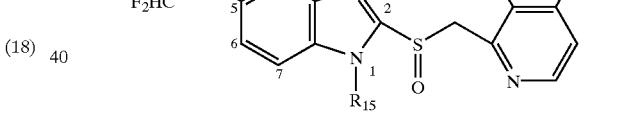
and isomers of the compounds of the formula where the $CH_3$ group is linked to the 6-position of the benzimidazole ring.
13. A compound of the formula
where $R_{15}$ is selected from the groups (1) through (5) shown below:

-continued (3)

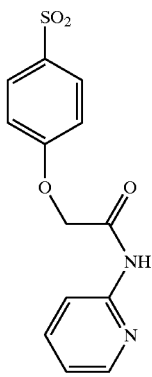

(4)

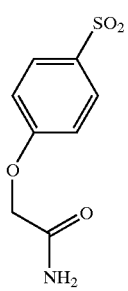

(5)

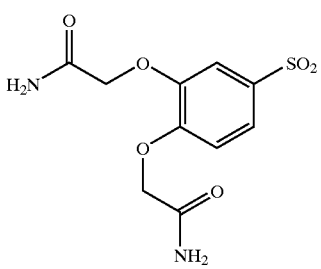

isomers of the compounds of the formula where the F₂HCO group is linked to the 6-position of the benzimidazole ring.

14. A pharmaceutical composition comprising a pharmaceutically acceptable excipient and a prodrug of a proton pump inhibitor in accordance with claim 1.

15. A pharmaceutical composition comprising a pharmaceutically acceptable excipient and a prodrug of a proton pump inhibitor in accordance with claim 4.

16. A pharmaceutical composition comprising a pharmaceutically acceptable excipient and a prodrug of a proton pump inhibitor in accordance with claim 9.

17. A pharmaceutical composition in accordance with claims 1, said composition comprising a liquid adapted for injection to a mammal, said liquid having a pH not exceeding 8.5 pH units.

18. A pharmaceutical composition comprising a pharmaceutically acceptable excipient, a prodrug of a proton pump inhibitor in accordance with claim 1, and a drug of the formula Het₁—X—S(O)—Het₂ where Het₂ is the group shown by the formula below

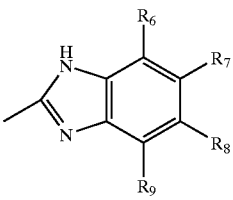

and where all other variables are defined as in claim 1.

19. A pharmaceutical composition comprising a pharmaceutically acceptable excipient, a prodrug of a proton pump inhibitor in accordance with claim 1, and a drug which has the formula selected from the formulas (a), (b), (c) and (d)

formula (a)

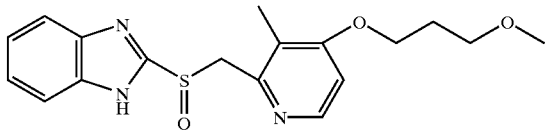

formula (b)

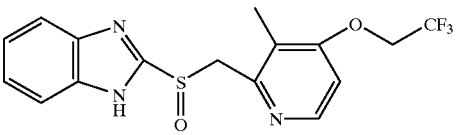

formula (c)

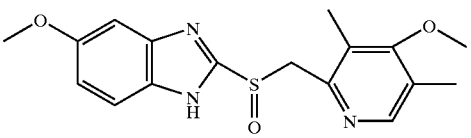

formula (d)

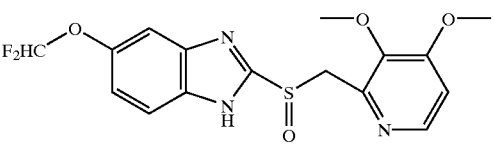

20. A compound of the formula

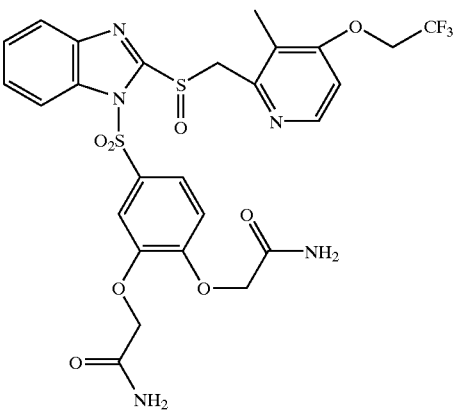

* * * * *

UNITED STATES PATENT AND TRADEMARK OFFICE
CERTIFICATE OF CORRECTION

PATENT NO.     : 6,559,167 B1
DATED          : May 6, 2003
INVENTOR(S)    : Garst et al.

It is certified that error appears in the above-identified patent and that said Letters Patent is hereby corrected as shown below:

<u>Title page,</u>
Item [56], References Cited, OTHER PUBLICATIONS, "Böhme" should be -- Böehme -- (both occurrences).

<u>Column 4,</u>
Line 53, "$R_6$" should be -- $R_{6'}$ --.

<u>Column 5,</u>
Line 44, "ethoxyl" should be -- ethoxy] --.

<u>Column 8,</u>
Line 21, "$Na^{+-O}{}_3S$" should be -- $Na^+{}^-O_3S$ --.
Line 22 "$(CH_3)_3NCH_2CH_2O$" should be -- $(CH_3)_3N^+CH_2CH_2O$ --.
Line 34, "$Na^{+-O}{}_3S$" should be -- $Na^+{}^-O_3S$ --.

<u>Column 9,</u>
Line 44, "$Na^{+-O}{}_3S$" should be -- $Na^+{}^-O_3S$ --.

<u>Column 12,</u>
Line 50, "6N" should be -- N --.

<u>Column 22,</u>
Line 20, "-H-" should be -- -1H- --.
Line 63, "of2" should be -- of 2 --.

<u>Column 25,</u>
Line 55, "1500" should be -- I 500 --.

<u>Column 28,</u>
Lines 9 and 26, "of(4" should be -- of (4 --.

<u>Column 30,</u>
Line 9, "I-" should be -- 1- --.
Line 20, "of0.1" should be -- of 0.1 --.

<u>Column 32,</u>
Line 29, "pyridylmethyl" should be -- pyridyl)methyl --.
Line 30, "sulfonyl-" should be -- sulfonyl]- --.

UNITED STATES PATENT AND TRADEMARK OFFICE
CERTIFICATE OF CORRECTION

PATENT NO. : 6,559,167 B1
DATED : May 6, 2003
INVENTOR(S) : Garst et al.

It is certified that error appears in the above-identified patent and that said Letters Patent is hereby corrected as shown below:

Column 33,
Line 43, "2[f(3,5" should be -- 2[[(3,5 --.
Line 44, "-2-17" should be -- -2- --.
Line 44, "sulfinyl-" should be -- sulfinyl]- --.

Column 39,
Line 37, "3.5" should be -- 3,5 --.
Line 59, "(4-1-{[2" should be -- (4-{[2 --.

Column 40,
Line 61, "2-[[4" should be -- 2-[[[4 --.

Column 42,
Line 12, "3.5" should be -- 3,5 --.
Line 38, "([3-" should be -- ({[3- --.

Column 44,
Line 38, "3.5" should be -- 3,5 --.

Column 45,
Line 14, "(in," should be -- (m, --.
Line 23, "3.5" should be -- 3,5 --.

Column 46,
Line 38, "3.5" should be -- 3,5 --.

Column 47,
Line 14, "3.5" should be -- 3,5 --.
Line 61, "3 5" should be -- 3,5 --.

Column 48,
Line 32, "($D_2$))" should be -- ($D_2O$) --.
Line 38, "(4-[5" should be -- {4-[5 - --.
Lines 60 and 63, "3.5" should be -- 3,5 --.

Column 50,
Line 10, "3 5" should be -- 3,5 --.

UNITED STATES PATENT AND TRADEMARK OFFICE
CERTIFICATE OF CORRECTION

PATENT NO.     : 6,559,167 B1
DATED          : May 6, 2003
INVENTOR(S)    : Garst et al.

It is certified that error appears in the above-identified patent and that said Letters Patent is hereby corrected as shown below:

Column 52,
Line 61, "P-cyclodextrin" should be -- β-cyclodextrin --.

Column 55,
Line 17, "1to 5" should be -- 1 to 5 --.

Column 57,
Line 11, "(alkoxy)," should be -- $(alkoxy)_n$ --.

Column 58,
Line 37, "poly(alkoxy) n" should be -- $poly(alkoxy)_n$ --.
Line 39, "$-(OCH_2CH_2)_n$'-" should be -- $-(OCH_2CH_2)_{n'}-$ --.

Column 59,
Line 1, "4acetaminobenzenesulfonyl" should be -- 4-acetaminobenzenesulfonyl --.
Line 5, "4methoxy" should be -- 4-methoxy --.
Line 10, "benzene4" should be -- benzene-4 --.
Line 41, "carbamoylmethoxy4" should be -- carbamoylmethoxy-4 --.

Column 60,
Line 21, "--methoxy" should be -- -4-methoxy --.
Line 54, "1- methoxy" should be -- 4-methoxy --.

Column 61,
Line 60, "3,4dimethoxy" should be -- 3,4-dimethoxy --.

Column 62,
Line 44, "5,4c" should be -- 5,4-c --.
Line 55, "4sulfonyl" should be -- 4-sulfonyl --.

UNITED STATES PATENT AND TRADEMARK OFFICE
CERTIFICATE OF CORRECTION

PATENT NO.   : 6,559,167 B1                                                     Page 4 of 4
DATED        : May 6, 2003
INVENTOR(S)  : Garst et al.

It is certified that error appears in the above-identified patent and that said Letters Patent is hereby corrected as shown below:

<u>Column 70,</u>
Line 15, group (22),

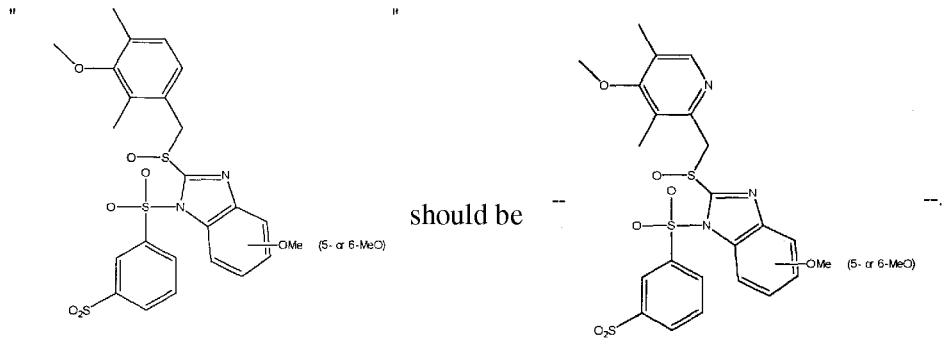

JAMES E. ROGAN
*Director of the United States Patent and Trademark Office*